(12) United States Patent
Veiseh et al.

(10) Patent No.: US 10,730,983 B2
(45) Date of Patent: Aug. 4, 2020

(54) BIOCOMPATIBLE COATINGS AND HYDROGELS FOR REDUCING FOREIGN BODY RESPONSE AND FIBROSIS

(71) Applicants: Massachusetts Institute of Technology, Cambridge, MA (US); The Children's Medical Center Corporation, Boston, MA (US)

(72) Inventors: Omid Veiseh, Cambridge, MA (US); Volkan Yesilyurt, Watertown, MA (US); Arturo Vegas, Belmont, MA (US); Joshua Doloff, Quincy, MA (US); Daniel G. Anderson, Framingham, MA (US); Robert S. Langer, Newton, MA (US)

(73) Assignees: MASSACHUSETTS INSTITUTE OF TECHNOLOGY, Cambridge, MA (US); THE CHILDREN'S MEDICAL CENTER CORPORATION, Boston, MA (US)

( * ) Notice: Subject to any disclaimer, the term of this patent is extended or adjusted under 35 U.S.C. 154(b) by 0 days.

(21) Appl. No.: 15/621,391

(22) Filed: Jun. 13, 2017

(65) Prior Publication Data

US 2017/0355799 A1    Dec. 14, 2017

Related U.S. Application Data

(60) Provisional application No. 62/349,408, filed on Jun. 13, 2016.

(51) Int. Cl.

| | |
|---|---|
| *C08F 230/02* | (2006.01) |
| *A61L 29/08* | (2006.01) |
| *A61L 27/26* | (2006.01) |
| *A61L 27/52* | (2006.01) |
| *A61L 27/34* | (2006.01) |
| *A61L 27/38* | (2006.01) |
| *A61L 27/54* | (2006.01) |
| *A61K 35/12* | (2015.01) |
| *A61K 9/50* | (2006.01) |
| *A61L 29/04* | (2006.01) |
| *A61L 31/10* | (2006.01) |
| *A61L 31/04* | (2006.01) |
| *A61L 27/56* | (2006.01) |
| *A61L 29/16* | (2006.01) |
| *A61L 31/16* | (2006.01) |
| *C08F 220/38* | (2006.01) |
| *C08F 30/02* | (2006.01) |
| *C08F 20/38* | (2006.01) |
| *A61B 5/145* | (2006.01) |

(52) U.S. Cl.
CPC ........ *C08F 230/02* (2013.01); *A61B 5/14532* (2013.01); *A61K 9/5026* (2013.01); *A61K 9/5036* (2013.01); *A61K 35/12* (2013.01); *A61L 27/34* (2013.01); *A61L 27/38* (2013.01); *A61L 27/52* (2013.01); *A61L 27/54* (2013.01); *A61L 27/56* (2013.01); *A61L 29/041* (2013.01); *A61L 29/085* (2013.01); *A61L 29/16* (2013.01); *A61L 31/048* (2013.01); *A61L 31/10* (2013.01); *A61L 31/16* (2013.01); *C08F 20/38* (2013.01); *C08F 30/02* (2013.01); *C08F 220/38* (2013.01); *A61B 2560/0223* (2013.01); *A61L 2300/404* (2013.01); *A61L 2400/18* (2013.01); *A61L 2420/02* (2013.01); *A61L 2420/06* (2013.01); *C08F 220/387* (2020.02); *C08F 2438/03* (2013.01); *C08F 2800/20* (2013.01)

(58) Field of Classification Search
CPC .............................. C08F 230/02; A61L 27/52
See application file for complete search history.

(56) References Cited

U.S. PATENT DOCUMENTS

| | | | |
|---|---|---|---|
| 2,881,161 | A | 4/1959 | Rudolf |
| 2,860,130 | A | 11/1985 | McNeely |
| 4,868,121 | A | 9/1989 | Scharp |
| 5,273,904 | A | 12/1993 | Langley |
| 5,322,790 | A | 6/1994 | Scharp |
| 5,336,668 | A | 8/1994 | Francesco |
| 5,443,505 | A | 8/1995 | Wong |
| 5,447,863 | A | 9/1995 | Langley |
| 5,662,718 | A | 4/1997 | Al-Shamkhani |
| 5,658,561 | A | 8/1997 | Nakabayashi |

(Continued)

FOREIGN PATENT DOCUMENTS

| | | |
|---|---|---|
| CN | 101565469 | 10/2009 |
| DE | 102005049833 | 4/2007 |

(Continued)

OTHER PUBLICATIONS

Chen et al., Macromolecules, 2013, 45, 119-127.*

(Continued)

*Primary Examiner* — Kyle A Purdy
(74) *Attorney, Agent, or Firm* — Pabst Patent Group LLP

(57) ABSTRACT

Zwitterionic polymers or biocompatible polymers with improved properties for cell encapsulation, coating of devices, or a combination thereof are described. The biocompatible polymer contains a zwitterionic monomer, a monomer with a reactive side chain, and optionally another hydrophobic monomer or a neutral hydrophilic monomer. The zwitterionic polymers are cross-linked with a cross-linker via covalent bond to form a zwitterionic hydrogel in the presence of cells. Also provided, are methods of making and using the zwitterionic polymers.

44 Claims, 10 Drawing Sheets

(56) References Cited

U.S. PATENT DOCUMENTS

| | | | |
|---|---|---|---|
| 5,821,121 | A | 10/1998 | Brothers |
| 5,876,452 | A | 3/1999 | Athanasiou |
| 6,159,531 | A | 12/2000 | Dang |
| 6,746,686 | B2 | 6/2004 | Hughes |
| 8,288,472 | B2 | 10/2012 | Chang |
| 9,006,359 | B2 | 4/2015 | Zhang |
| 9,139,684 | B2 | 9/2015 | Coneski |
| 2005/0208093 | A1 | 9/2005 | Glauser |
| 2008/0003250 | A1 | 1/2008 | Margulies |
| 2008/0044900 | A1 | 2/2008 | Mooney |
| 2008/0199914 | A1 | 8/2008 | Skjak-Braek |
| 2008/0242738 | A1 | 10/2008 | Marks |
| 2008/0268189 | A1 | 10/2008 | Sun |
| 2009/0148591 | A1 | 6/2009 | Wang |
| 2009/0197791 | A1* | 8/2009 | Balastre ............. A61K 8/8158 510/407 |
| 2010/0145286 | A1 | 6/2010 | Zhang |
| 2010/0247614 | A1 | 9/2010 | Jiang |
| 2011/0105712 | A1 | 5/2011 | Jiang |
| 2011/0319569 | A1* | 12/2011 | Emrick ............ A61K 47/48176 525/326.6 |
| 2012/0009159 | A1 | 1/2012 | Humayun |
| 2012/0083767 | A1 | 4/2012 | Gerstenblith |
| 2012/0282299 | A1 | 11/2012 | Delamarre |
| 2013/0149351 | A1 | 6/2013 | Woo |
| 2013/0211212 | A1 | 8/2013 | Stumber |
| 2013/0224276 | A1 | 8/2013 | Hunter |
| 2014/0235803 | A1 | 8/2014 | Jiang |
| 2014/0370567 | A1 | 12/2014 | Jiang |
| 2015/0037598 | A1 | 2/2015 | Jiang |
| 2015/0045515 | A1 | 2/2015 | Li |
| 2015/0157732 | A1 | 6/2015 | Jiang |
| 2015/0183939 | A1* | 7/2015 | Lequeux ............. C09K 11/565 436/501 |
| 2015/0197644 | A1 | 7/2015 | Chang |
| 2015/0368713 | A1 | 12/2015 | Bharti |
| 2016/0030360 | A1 | 2/2016 | Vegas |
| 2017/0014776 | A1* | 1/2017 | Li ..................... B01D 67/0088 |
| 2017/0226232 | A1 | 8/2017 | Vegas |
| 2017/0239397 | A1 | 8/2017 | Vegas |
| 2017/0246347 | A1 | 8/2017 | Vegas |

FOREIGN PATENT DOCUMENTS

| | | |
|---|---|---|
| DE | 102005049833 | 4/2017 |
| EP | 1614696 | 1/2006 |
| FR | 2699545 | 6/1994 |
| FR | 2699545 | 6/2009 |
| GB | 676618 A | 7/1952 |
| GB | 768309 A | 2/1957 |
| WO | 99/00070 | 1/1999 |
| WO | 9900070 | 1/1999 |
| WO | 2003/010354 | 2/2003 |
| WO | 2003010354 | 2/2003 |
| WO | 2003/085372 | 10/2003 |
| WO | 2003085372 | 10/2003 |
| WO | 2005/058382 | 6/2005 |
| WO | 2005058382 | 6/2005 |
| WO | 2005/063147 | 7/2005 |
| WO | 2005063147 | 7/2005 |
| WO | 2009/032158 | 3/2009 |
| WO | 2009032158 | 3/2009 |
| WO | 2010090767 | 8/2010 |
| WO | 2012/167223 | 12/2012 |
| WO | 2012167223 | 12/2012 |
| WO | 2016/019391 | 2/2013 |
| WO | 2013/121983 | 8/2013 |
| WO | 2013121983 | 8/2013 |
| WO | 2014/052080 | 4/2014 |
| WO | 2014052080 | 4/2014 |
| WO | 2014194268 | 12/2014 |
| WO | WO 2014/194268 | 12/2014 |
| WO | 2015054484 | 4/2015 |
| WO | 2015055656 | 4/2015 |
| WO | WO 2015/054484 | 4/2015 |
| WO | WO 2015/055656 | 4/2015 |
| WO | 2015/187204 | 12/2015 |
| WO | 2015187204 | 12/2015 |
| WO | 2016019391 | 3/2017 |
| WO | 2017/075630 | 5/2017 |
| WO | 2017075630 | 5/2017 |
| WO | 2017/218507 | 12/2017 |
| WO | 2017218507 | 12/2017 |

OTHER PUBLICATIONS

Zhang, et al., "Synthesis and characterization of phosphoryl-chlorine-capped poly(epsilon-caprolactone)-poly(ethylene oxide) di-block co-polymers and its surface modification on polyurethanes", *J Biomat Sci Polym Ed.*, 19(4):509-24 (2008).

Chu, et al., "A soft and flexible biosensor using phospholipid polymer for continuous glucose monitoring", Biomedical Microdevices, 11(4): 837-842 (2009).

Devos, et al., "Improved biocompatibility but limited graft survival after purification of alginate for microencapsulation of pancreatic islets", Diabetologia 40(3):262-70 (1997).

Kovach, et al., "The Effects of PEG-based surface modification of PDMS microchannels on long-term hemocompatibility", J. of Biomedical Research Pt. A, 102A:4195-4205 (2014).

Ratner, "A pore way to heal and regenerate: 21st century thinking on biocompatibility", Regenerative Biomaterials, 107-110 (2016).

Chen, et al., "Multifunctional Biocompatible Membrane and it's application to fabricate a miniaturized glucose sensor with potential for us in vivo", *Biomedical Microdevices*, 1(2):155-166 (1998).

Chen, "Differentiation of rat marrow mesenchymal stem cells into pancreatic islet beta-cells", *World Journal of Gastroenterology*, 10(20): 3016-3020 (2004).

Chu, et al., "A soft and flexible biosensor using a phospholipid polymer for continuous glucose monitoring", *Biomedical Microdevices*, 11(4):837-842 (2009).

Costa, et al., "Covalent immobilization of antimicrobial peptides (AMPs) onto biomaterial surfaces", *Acta Biomaterialia*, 7(5): 1431-1440 (2010).

Cui, et al., "Electrochemical deposition and characterization of poly(3,4-ethylenedioxythiopene) on neural microelectrode arrays", *Sensors and actuators B: Chemical: International Journal Devoted to Research and Development of Physical and Chemical Transducers*, 89(1-2): 92-102 (2003).

Dai, "Swelling characteristics and drug delivery properties of nifedipine-loaded pH sensitive alginate-chitosan hydrogel beads", Journal of Biomedical Materials Research Part B: Applied Biomaterials, 86(2):493-500 (2008).

Desei, et al., "Advances in islet encapsulation technologies", *Nature Reviews, Drug Discovery*, 16(5):338-350 (2016).

Dusseault, "Evaluation of alginate purification methods: effect on polyphenol, endotoxin, and protein contamination", *J Biomed Mater Res A.*, 76(2):243-251 (2006).

Gattas-Asfura, "Chemoselective cross-linking and functionalization of alginate via Staudinger ligation", *Biomacromolecules*, 10:3122-3129 (2009).

Hall, "Microencapsulation of islets within alginate/poly(ethylene glycol) gels cross-linked via Staudinger ligation", *Acta Biomaterialia*, 7:614-624 (2011).

Hersel, et al., "RGD modified polymers: biomaterials for stimulated cell adhesion and beyond", *Biomaterials*, 24(24):4385-4415 (2003).

Hudalla, et al., "Immobilization of peptides with distinct biological activities onto stem cell culture substrates using orthogonal chemistries", *Langmuir*, 26(9):6449-6456 (2010).

Huh, et al., "From 3D cell culture to organs-on-chips", 21(12): 745-754 (2011).

Klock, "Biocompatibility of mannuronic acid-rich alginates", *Appl Microbiol Biotechnol*, 40:638-643 (1994).

Pedraza, "Engineering an optimal bioartificial pancreas for islet transplantation using bioactive scaffolds", *Dissertation (Ph.D.) University of Miami*, (2011).

Skrzypek, et al., "Pancreatic islet macroencapsulation using microwell porous membranes", *Scientific Reports*, 7(1) (2017).

(56) References Cited

OTHER PUBLICATIONS

Sun, et al., "Funcitonalization of quantum dots with multidentate zwitterionic ligands: impact on cellular interactions and cytotoxicicty", *Journal of Materials Cemistry B*, 1(44):6137 (2013).
Thevenot, et al., "Surface chemistry infulences implant biocompatibility", *Current topics in Medicinal Chemistry*, 1-21 (2011).
Valle, et al., "Synthesis and rheological properties of hydrogels based on amphilic alginate-amide derivatives", *Carbohydrate Research*, 344(2):223-228 (2009).
Wang, et al., "Significantly reduced absorption and activation of blood components in a membrane oxygenator system coated with crosslinkable zwitterionic copolymer", *ACTA Biomaterialia*, 40(8): 153-161 (2016).
West, et al., "The biocompatibility of crosslinkable copolymer coatings containing sulfobetaines and phosphobetaines", *Biomateri*, 25(7-8): 1195-1204 (2004).
Wikstrom, et al., Alginate-base microencapsulation of retinal epithelial cell line for cell therapy, *Biomaterials*, 29:869-876 (2008).
Yang, et al., "Zwitterionic poly(carboxybetaine) hydrogels for glucose biosensors in complex media", *Biosensors and Bioelectronics*, 26(5): 2454-2459 (2011a).
Yang, et al., "Research progress on chemical modification of alginate: A review", *Carbohydrate Polymers*, 84(1):33-39 (2011b).
Yesilyurt, et al., "A Facile and Versatile Method to Endow Biomaterial Devices with Zwitterionic Surface Coatings", *Advanced Healthcare Materials*, 6(4): 2192-2640 (2016).
Extendend European Search Report issued for EP 18 16 2427 dated Jun. 19, 2018.
Pedraza, et al., "Macroporous three-dimensional PDMS scaffolds for extrahepatic islet transplantation", *Cell Transplantation*, 22:1123-1135 (2013).
Tang, et al., "Reprogramming liver-stem WB cells into functional insulin-producing cells by persistent expression of Pdx1-and Pdx1-VP16 mediated by lentiviral vectors", *Lab Invest.*, 86(1)83-93 (2006).
Tang, et al., "Reprogramming liver-stem WB fcells into functional insulin-prodcuing cells by persistent expression of Pdx1-and Pdx1-VP16 mediated by lentiviral vectors", Lab Invest 86(1)83-93 (2006).
Anderson, et al., "Foreign body reaction to biomaterials", Semin. Immunol., 20:86-100 (2008).
Bratlie, et al., "Rapid Biocompatibility Analysis of Materials via In Vivo Fluorescence Imaging of Mouse Models", Plos One, 5(4):C1032 (2010).
Chen, et al., "Novel Zwitterionic Copolymers with Dihydrolipoic Acid: Synthesis and Preparation of Nonfouling Nanorods", Macromolecules, 46:119-27 (2013).
Chienm, et al., "Surface conjugation of zwitterionic polymers to inhibit cell adhesion and protein adsorption", Colloids Surfaces B, 107:152-9 (2013).
Field, et al., "Improved islet isolation from rat pancreas using 35% bovine serum albumin in combination with Dextran gradient separation", Transplantation 61:1554-56 (1996).
Grainger, "All charged up about implanted biomaterials", Nat. Biotechnol. 31:507-9 (2013).
Ham, et al., "Facile DNA immobilization on surfaces through a catecholamine polymer", Angew. Chem. Int. Ed., 50:732-6 (2011).
Harding and Reynolds, "Combating medical device fouling", Trends Biotechnol. 32:140-6 (2014).
Hetrick, et al., "Reduced foreign body response at nitric oxide-releasing subcutaneous implants", Biomaterials 28:457-80 (2007).
Ishara, et al., "Antithrombogenic polymer alloy composed of 2-methacryloyloxyethyl phosphorylcholine polymer and segmented polyurethane", J Biomat Sci Polymet, 11(11):1183-95 (2000).
Kim, et al., "Cytoprotective alginate/polydopamine core/shell microcapsules in microbial encapsulation", Angew. Chem. Int. Ed., 53:14443-6 (2014).
King, et al., "The effect of host factors and capsule composition on the cellular overgrowth on implanted alginate capsules", J. Biomed. Mater. Res., 57:374-83 (2001).

Kobayashi, et al., "Segmented polyurethane modified by photopolymerization and cross-linking with 2-methacryloyloxyethyl phosphorylcholine polymer for blood-contacting surfaces of ventricular assist devices", Int J Artificial Organs, 8(4):237-44 (2005).
Langer, "Perspectives and challenges in tissue engineering and regenerative medicine", Adv. Mater., 21:3235-6 (2009).
Lee, et al., "Mussel-inspired surface chemistry for multifunctional coatings", Science, 318:426 (2007).
Lee, et al., "Facile Conjugation of Biomolecules onto Surfaces via Mussel Adhesive Protein Inspired Coatings", Adv. Mater., 21:431-4 (2009).
Lee and Mooney, "Alginate: properties and biomedical applications.", Prog. Polym. Sci. 37, 106 (2012).
Lim and Sun, "Microencapsulated islets as bioartificial endocrine pancreas", Science, 210:908-10 (1980).
Lin, et al., "Photoreactive Polymers Bearing a Zwitterionic Phosphorylcholine Group for Surface Modification of Biomaterials", ACS App Mat Interfaces, 7(31):17489-98 (2015).
Linetsky, et al., "Improved human islet isolation using a new enzyme blend, liberase", Diabetes 46:1120-3 (1997).
Ma, et al., "Development of cationic polymer coatings to regulate foreign-body responses", Adv. Mater.,23:H189-94 (2011).
Ratner, "Reducing capsular thickness and enhancing angiogenesis around implant drug release systems" J. Controlled Release 78:211-218 (2002).
Rodriguez, et al., "Quantitative in vivo cytokine analysis at synthetic biomaterial implant sites", J. Biomed. Mater. Res. A,89:152-9 (2009).
Scharp and Marchetti, "Encapsulated islets for diabetes therapy: history, current progress, and critical issues requiring solution", Adv. Drug. Deliv. Rev., 67-68:35-73 (2014).
Seetho, et al., "Facile Synthesis of a Phosphorylcholine-Based Zwitterionic Amphiphilic Copolymer for Anti-Biofouling Coatings", ACS Macro Lett., 4:505-10 (2015).
Spasojevic, et al., "Reduction of the inflammatory responses against alginate-poly-L-lysine microcapsules by anti-biofouling surfaces of PEG-b-PLL diblock copolymers", PLoS One, 9:e109837 (2014).
Sussman, et al., "Porous Implants Modulate Healing and Induce Shifts in Local Macrophage Polarization in the Foreign Body Reaction", Ann. Biomed. Eng., 42:1508-16 (2013).
Tu, et al., "Synthesis of polyethylene glycol- and sulfobetaine-conjugated zwitterionic poly(L-lactide) and assay of its antifouling properties",Colloids Surf B Biointerfaces, 102:331-40 (2013).
Vegas, et al., "Combinatorial hydrogel library enables identification of materials that mitigate the foreign body response in primates", Nat. Biotechnol., 34:345-52 (2016).
Veiseh, et al., "Size- and shape-dependent foreign body immune response to materials implanted in rodents and non-human primates", Nat. Mater.,14:643-51 (2015).
Ward, "A review of the foreign-body response to subcutaneously-implanted devices: the role of macrophages and cytokines in biofouling and fibrosis", Diabetes Sci. Technol. Online 2(5):768-77 (2008).
Wick, et al., "The immunology of fibrosis", Annu. Rev. Immunol. 31:107-35 (2013).
Williams, "On the mechanisms of biocompatibility", Biomaterials, 29:2941-53 (2008).
Wynn and Ramalingam, "Mechanisms of fibrosis: therapeutic translation for fibrotic disease", Nat. Med. 18:1028-40 (2012).
Yuan, et al., "Polyurethane vascular catheter surface grafted with zwitterionic sulfobetaine monomer activated by ozone", Colliods Surface B, 35(1):1-5 (2004).
Zhang et al., "Zwitterionic hydrogels implanted in mice resist the foreign-body rea", Nat. Biotechnol. 31:553-6 (2013).
Zhang, et al., "Synthesis and characterization of phosphoryl-choline-capped poly(epsilon-caprolactone)-poly(ethylene oxide) di-block co-polymers and its surface modification on polyurethanes", J Biomat Sci Polym Ed., 19(4):509-24 (2008).
Ahad, et al., "Surface modification of polymers for biocompatibility via exposure to extreme ultraviolet radiation", Society for Biomaterials, 3296-3310 (2013).

* cited by examiner

SB1 SB2 CB1 CB2 CB3 MPC M1

BIOCOMPATIBLE COATINGS AND HYDROGELS FOR REDUCING FOREIGN BODY RESPONSE AND FIBROSIS

CROSS REFERENCE TO RELATED APPLICATIONS

This application claims benefit of and priority to U.S. Provisional Application No. 62/349,408 filed Jun. 13, 2016, and where permissible is hereby incorporated by reference in its entirety.

STATEMENT REGARDING FEDERALLY SPONSORED RESEARCH

This invention was made with government support under Grant Nos. EB000244, EB000351, DE013023, CA151884, and P41EB015871-27 awarded by the National Institutes of Health; and Grant Nos. 3-2013-178 and W81XWH-13-1-0215 awarded by the Department of Defense/Congressionally Directed Medical Research Programs. The government has certain rights in the invention.

FIELD OF THE INVENTION

This invention is in the field of materials with improved biocompatibility, particularly implantable devices with reduced foreign body response.

BACKGROUND OF THE INVENTION

The foreign body response is an immune-mediated reaction that impacts the fidelity of implanted biomedical devices (Anderson et al., *Semin. Immunol.* 20:86-100 (2008); Langer, *Adv. Mater.* 21:3235-3236 (2009); Ward, *J. Diabetes Sci. Technol. Online* 2:768-777 (2008); Harding & Reynolds, *Trends Biotechnol.* 32:140-146 (2014)). Macrophage recognition of biomaterial surfaces in these devices initiate a cascade of inflammatory events that result in the fibrous and collagenous encapsulation of these foreign materials (Anderson et al. (2008); Ward (2008); Harding & Reynolds (2014); Grainger, *Nat. Biotechnol.* 31:507-509 (2013); Williams, *Biomaterials* 29:2941-2953 (2008)). This encapsulation, over time, often leads to device failure and can result in discomfort for the recipient (Anderson et al. (2008); Harding & Reynolds (2014); Williams (2008)). These adverse outcomes emphasize the critical need for biomaterials that do not elicit foreign body responses to overcome this key challenge to long-term biomedical device function.

The foreign body response to implanted biomaterials is the culmination of inflammatory events and wound-healing processes resulting in implant encapsulation (Anderson et al. (2008)). The final pathological product of this response is fibrosis, which is characterized by the accumulation of excessive extracellular matrix at sites of inflammation and is a key obstacle for implantable medical devices as the cellular and collagenous deposition isolate the device from the host (Anderson et al. (2008); Wick et al., *Annu. Rev. Immunol.* 31:107-135 (2013); Wynn & Ramalingam, *Nat. Med.* 18:1028-1040 (2012)). This device isolation can interfere with sensing of the host environment, lead to painful tissue distortion, cut off nourishment (for implants containing living, cellular components), and ultimately lead to device failure. Materials commonly used for medical device manufacture today elicit a foreign body response that results in fibrous encapsulation of the implanted material (Langer (2009); Ward (2008); Harding & Reynolds (2014); Williams (2008); Zhang et al., *Nat. Biotechnol.* 31:553-556 (2013)). Overcoming the foreign body response to implanted devices could pave the way for implementing new medical advances, making the development of materials with both anti-inflammatory and anti-fibrotic properties a critical medical need (Anderson et al. (2008); Langer (2009); Harding & Reynolds (2014)).

Macrophages are a key component of material recognition and actively adhere to the surface of foreign objects (Anderson et al. (2008); Ward (2008); Grainger, *Nat. Biotechnol.* 31:507-509 (2013); Sussman et al., *Ann. Biomed. Eng.* 1-9 (2013) (doi:10.1007/s10439-013-0933-0)). Objects too large for macrophage phagocytosis initiate processes that result in the fusion of macrophages into foreign-body giant cells. These multi-nucleated bodies amplify the immune response by secreting cytokines and chemokines that result in the recruitment of fibroblasts that actively deposit matrix to isolate the foreign material (Anderson et al. (2008); Ward (2008); Rodriguez et al., *J. Biomed. Mater. Res. A* 89:152-159 (2009); Hetrick et al., *Biomaterials* 28:4571-4580 (2007)). This response has been described for materials of both natural and synthetic origins that encompass a wide range of physicochemical properties, including alginate, chitosan, dextran, collagen, hyaluronan, poly(ethylene glycol) (PEG), poly(methyl methacrylate) (PMMA), poly(2-hydroxyethyl methacrylate) (PHEMA), polyurethane, polyethylene, silicone rubber, Teflon, gold, titanium, silica, and alumina (Ward (2008); Ratner, *J. Controlled Release* 78:211-218 (2002)).

The development of implantable devices that resist host foreign body responses for protracted periods of time is important for improving the performance and safety of such devices, and remains an unmet need.

Accordingly, the search for materials of clinical relevance that address the foreign body response to implantable devices, i.e., ameliorate biocompatibility, remains an area of active research.

Therefore, it is an object of the invention to provide polymers for encapsulating and implanting cells, where the polymers have greater biocompatibility following implantation.

It is another object of the invention to provide polymers for modifying the surface of a product to impart a beneficial effect to the product compared to a corresponding product that lacks the polymers.

It is also an object of the invention to provide methods for encapsulating cells using polymers.

It is also an object of the invention to provide methods for modifying the surface of a product using polymers, where the modified product has improved biocompatibility compared to a corresponding product that lacks the polymers.

SUMMARY OF THE INVENTION

Zwitterionic polymers or biocompatible polymers with improved properties for cell encapsulation, coating of devices, or a combination thereof have been developed. The biocompatible polymer contain zwitterionic monomer, monomer with a reactive side chain, and optionally another hydrophobic monomer or a neutral hydrophilic monomer.

In some embodiments, the zwitterionic polymers are cross-linked with a cross-linker via covalent bonds to form a zwitterionic hydrogel, optionally in the presence of cells. When cross-linking occurs in the presence of cells, the weight average molecular weights of the zwitterionic polymers are selected to avoid cytotoxicity.

Also provided are methods of synthesizing zwitterionic polymers that contain a monomer with a reactive side chain, and cross-linking the zwitterionic polymers with a cross-linker via covalent bond formation to form a zwitterionic hydrogel. In some embodiments, the cross-linking of the zwitterionic polymers is carried out in the presence of cells to be encapsulated. In some embodiments, the cross-linking is carried out in a medium that is substantially free of organic solvents. In some embodiments, the cross-linking of the zwitterionic polymers is carried out in the presence of cells to be encapsulated and in a medium that is substantially free of organic solvents. Preferably the cross-linking reaction occurs in the presence of cells to be encapsulated, while avoiding any of the use of extreme temperatures, the presence of toxic photoinitiators, and reagents that damage cells.

The zwitterionic polymers can be used to encapsulate cells, coat biomaterials and other medical devices. Methods of use are described. Examples demonstrate enhanced biocompatibility and decreased cell toxicity.

BRIEF DESCRIPTION OF THE DRAWINGS

FIG. 6A is a schematic of the surface coating of alginate microspheres. FIG. 6B is a schematic of the synthesis and structure of thiol-containing zwitterionic copolymer.

FIG. 7A shows the quantity of myeloid cells retrieved from implanted alginate microspheres and the quantity of myeloid cells retrieved from implanted alginates microspheres with a zwitterionic polymer (poly(methacryloyloxyethyl phosphorylcholine)) on its surface. FIG. 7B shows the quantity of myeloid cells retrieved from implanted polystyrene microspheres and the quantity of myeloid cells retrieved from implanted polystyrene microspheres with a zwitterionic polymer (poly(methacryloyloxyethyl phosphorylcholine)) on its surface.

DETAILED DESCRIPTION OF THE INVENTION

I. Definitions

Figures 1A, 1B, 1C, 1D, 1E, 1F, 1G:
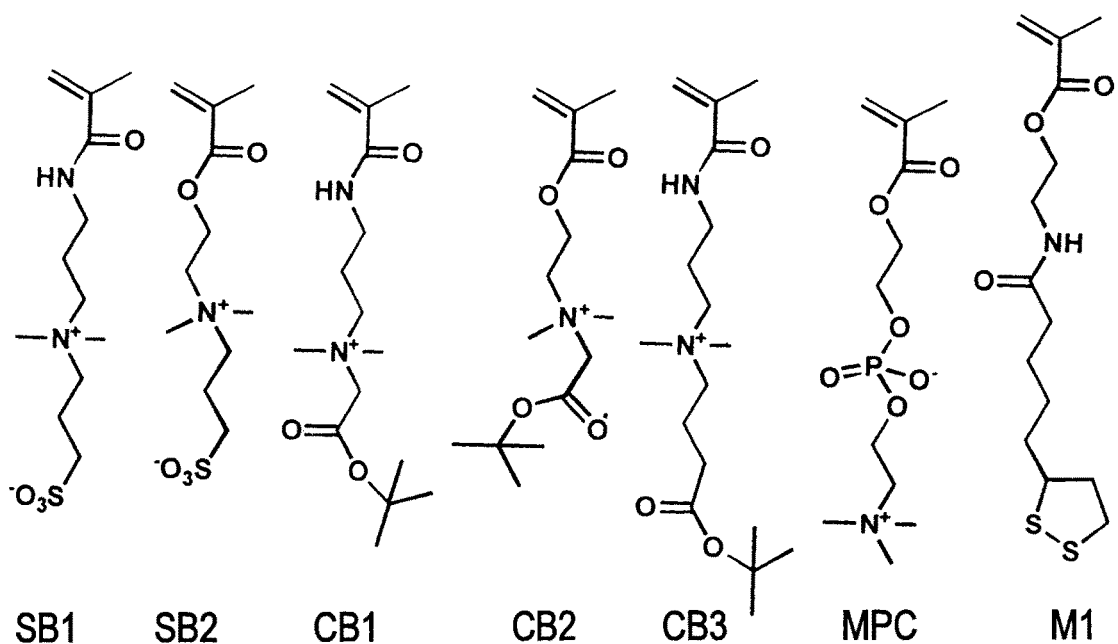
FIG. 1A-1G are representative zwitterionic monomers and zwitterionic monomer precursors, and a monomer containing a reactive side chain or a side chain with a reactive group. CB1, CB2, and CB3 are precursor monomers to their corresponding zwitterionic monomers. These monomers can be deprotected after polymerizations to get the corresponding zwitterions. M1 is also deprotected after polymerization to generate reactive free thiols.

"Beneficial effect," as used herein, refers to any effect that is desired. In the context disclosed herein, beneficial effects include lower foreign body response, improved biocompatibility measured by less cell toxicity, and reduced immune response or reaction.

"Biocompatible," as used herein, refers to a substance or object that performs its desired function when introduced into an organism without inducing significant inflammatory response, immunogenicity, or cytotoxicity to native cells, tissues, or organs, or to cells, tissues, or organs introduced with the substance or object. For example, a biocompatible product is a product that performs its desired function when introduced into an organism without inducing significant inflammatory response, immunogenicity, or cytotoxicity to native cells, tissues, or organs.

Biocompatibility, as used herein, can be quantified using the following in vivo biocompatibility assay. A material or product is considered biocompatible if it produces, in a test of biocompatibility related to immune system reaction, less than 50%, 45%, 40%, 35%, 30%, 25%, 20%, 15%, 10%, 8%, 6%, 5%, 4%, 3%, 2%, or 1% of the reaction, in the same test of biocompatibility, produced by a material or product the same as the test material or product except for a lack of the surface modification on the test material or product. Examples of useful biocompatibility tests include measuring and assessing cytotoxicity in cell culture, inflammatory response after implantation (such as by fluorescence detection of cathepsin activity), and immune system cells recruited to implant (for example, macrophages and neutrophils).

"Capsule," as used herein, refers to a particle having a mean diameter of about 150 µm to about 5 cm, formed of a cross-linked hydrogel, having a cross-linked hydrogel core that is surrounded by one or more polymeric shells, having one or more cross-linked hydrogel layers, having a cross-linked hydrogel coating, or a cell encapsulation. The capsule may contain one or more cells dispersed in the cross-linked hydrogel, thereby "encapsulating" the cells. Reference to "capsules" herein refers to and includes microcapsules unless the context clearly indicates otherwise. Preferred capsules have a mean diameter between about 150 µm and about 30 mm, inclusive. Preferably, the capsules have a mean diameter of about 5 mm.

"Microcapsule" and "microgel," as used herein, are used interchangeably to refer to a particle or capsule having a mean diameter between about 150 µm and about 1000 µm, inclusive.

"Biological material" and "biomaterial," as used herein, refers to any biological substance, including, but not limited to, tissue, cells, biological micromolecules, such as proteins, nucleic acid molecules, sugars and polysaccharides, lipids, and combinations thereof, for example, enzymes, receptors, secretory proteins, structural and signaling proteins, hormones, and ligands.

"Coating" as used herein, refers to any temporary, semi-permanent or permanent layer, covering or surface. A coating can be applied as a gas, vapor, liquid, paste, semi-solid, or solid. In addition a coating can be applied as a liquid and solidified into a hard coating. Elasticity can be engineered into coatings to accommodate pliability, e.g. swelling or shrinkage, of the substrate or surface to be coated.

"Corresponding product" and "similar product," as used herein, refer to a product that has, as far as is practical or possible, the same composition, structure, and construction as a reference product. The terms "corresponding" and "similar" can be used for the same meaning with any particular or subgroup of products or other materials described herein. For example, a "similar surface modification" refers a surface modification that has, as far as is practical or possible, the same composition, structure, and construction as a reference surface modification.

"Control corresponding product" and "control similar product," as used herein, refers to a product that has, as far as is practical or possible, the same composition, structure, and construction as a reference product except for one or more specified parameters. For example, a control corresponding product that lacks the chemical modification in reference to a chemically modified product refers to a product that has, as far as is practical or possible, the same composition, structure, and construction as a reference product except for the chemical modification. Generally, a product prior to chemical modification constitutes a control corresponding product to the chemically modified form of the product. The terms "control corresponding" and "control similar" can be used for the same meaning with any particular or subgroup of products or other materials described herein. For example, a "control similar surface modification" refers a surface modification that has, as far as is practical or possible, the same composition, structure, and construction as a reference surface modification except for one or more specified parameters. Components that are "control corresponding" or "control similar" relative to a reference component are useful as controls in assays assessing the effect of independent variables.

"Foreign body response" as used herein, refers to the immunological response of biological tissue to the presence of any foreign material in the tissue which can include protein adsorption, infiltration by immune cells or fibrosis.

"Hydrophilic" refers to molecules which have a greater affinity for, and thus solubility in, water as compared to organic solvents. The hydrophilicity of a compound can be quantified by measuring its partition coefficient between water (or a buffered aqueous solution) and a water-immiscible organic solvent, such as octanol, ethyl acetate, methylene chloride, or methyl tert-butyl ether. If after equilibration a greater concentration of the compound is present in the water than in the organic solvent, then the molecule is considered hydrophilic.

"Hydrophobic" refers to molecules which have a greater affinity for, or solubility in an organic solvent as compared to water. The hydrophobicity of a compound can be quantified by measuring its partition coefficient between water (or a buffered aqueous solution) and a water-immiscible organic solvent, such as octanol, ethyl acetate, methylene chloride, or methyl tert-butyl ether. If after equilibration a greater concentration of the compound is present in the organic solvent than in the water, then the molecule is considered hydrophobic.

"Hydrogel," as used herein, refers to a gelatinous colloid, or aggregate of polymeric molecules in a finely dispersed semi-solid state, where the polymeric molecules are in the external or dispersion phase and water (or an aqueous solution) is forms the internal or dispersed phase. Generally, hydrogels are at least 90% by weight of an aqueous solution.

"Implanting," as used herein, refers to the insertion or grafting into the body of a subject of a product or material.

"Neutral" refers to a monomer or monomeric unit within a polymer that does not contain a charged group covalently bound to another atom within the monomer or monomeric unit.

"Pharmaceutically acceptable excipient" refers to a carrier that is physiologically acceptable to the subject to which it is administered and that preserves the therapeutic properties of the compound with which it is administered. One exemplary pharmaceutically acceptable excipient is physiological saline. Other physiologically acceptable excipients and their formulations are known to one skilled in the art and described, for example, in "Remington: The Science and Practice of Pharmacy," (20th ed., ed. A. R. Gennaro, 2000, Lippincott Williams & Wilkins).

"Reactive side chain" refers to the pendant group of a monomer or monomeric unit within a polymer, which contains an organic functional group that reacts with another organic functional group to form a covalent bond.

"Surface modification" and related terms, as used herein in the context of the disclosed products, refers to chemical modification of the surface of the product. Generally, such surface modification is by direct attachment, coupling, or adherence of a compound to the surface material of the product. Preferably, the surface modification involves modification with one or more of the disclosed compounds. Surface modification, as defined herein in the context of the disclosed products, can be accomplished at any time and in any manner, including, for example, synthesis or production of the modified form of the product or material when the product or material is formed, addition of the chemical modification after the final product or material is formed, or at any time in between. Except where specifically and expressly provided to the contrary, the term "surface modification" refers to a structural property, regardless of how the structure was formed, and the structure is not limited to a structure made by any specific method.

In some embodiments, the moieties or compounds modifying the product can be present on the surface of the product, and are not present, or are not present in a significant amount, elsewhere in the product, e.g., on an internal or interior surface. In some embodiments, at least 50, 60, 70, 80, 90, 95, or 99% of the moieties or compounds are present on the surface of the product. In some embodiments, the moieties or compounds (e.g., a moiety or compound described herein) are present on the exterior face of the surface of the product, and are not present, or not present in a significant amount, elsewhere in the product, e.g., on an internal or interior surface. In some embodiments, at least 50, 60, 70, 80, 90, 95, or 99% of the moieties or compounds are present on the external face of the surface of the product.

"Surface," as used herein in the context herein, refers to a boundary of a product. The surface can be an interior surface (e.g. the interior boundary of a hollow product), or an exterior or outer boundary or a product. Generally, the surface of a product corresponds to the idealized surface of a three dimensional solid that is topological homeomorphic with the product. The surface can be an exterior surface or an interior surface. An exterior surface forms the outermost layer of a product or device. An interior surface surrounds an inner cavity of a product or device, such as the inner cavity of a tube. As an example, both the outside surface of a tube and the inside surface of a tube are part of the surface of the tube. However, internal surfaces of the product that are not in topological communication with the exterior surface, such as a tube with closed ends, can be excluded as the surface of a product. In some embodiments, an exterior surface of the product is chemically modified, e.g., a surface that can contact an immune system component. In some embodiments, where the product is porous or has holes in its mean (idealized or surface), the internal faces of passages and holes are not considered part of the surface of the product if its opening on the mean surface of the product is less than 1 µm.

"Substantial" and "substantially," as used herein, specify an amount of between 95% and 100%, inclusive, between 96% and 100%, inclusive, between 97% 100%, inclusive, between 98% 100%, inclusive, or between 99% 100%, inclusive.

"Zwitterion," "zwitterionic," and "zwitterionic monomer" are used interchangeably to refer to chemical compound, or a monomer or monomeric unit within a polymer, which contains one or more cationic groups and one or more anionic groups. Typically, the charges on the cationic and anionic groups are balanced, resulting in a monomer with zero net charge. However, it is not necessary that the charges on the cationic and anionic groups balance out.

"Zwitterionic polymer" refers to a polymer that contains at least a zwitterionic monomer, monomers with cationic and anionic groups on different monomer units, or a combination thereof. The zwitterionic polymers can be random copolymers, block copolymers, or a combination thereof.

"Biocompatible polymer" is used interchangeably with "zwitterionic polymer."

"Zwitterionic hydrogel" refers to a hydrogel that contains a zwitterion. "Biocompatible hydrogel" is used interchangeably with "zwitterionic hydrogel."

"Substituted," as used herein, refers to all permissible substituents of the compounds or functional groups described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups. Such alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups can be further substituted.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

"Aryl," as used herein, refers to $C_5$-$C_{26}$-membered aromatic, fused aromatic, fused heterocyclic, or biaromatic ring systems. Broadly defined, "aryl," as used herein, includes 5-, 6-, 7-, 8-, 9-, 10-, 14-, 18-, and 24-membered single-ring aromatic groups, for example, benzene, naphthalene, anthracene, phenanthrene, chrysene, pyrene, corannulene, coronene, etc.

"Aryl" further encompasses polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles.

The term "substituted aryl" refers to an aryl group, wherein one or more hydrogen atoms on one or more aromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfonamido, sulfonyl, heterocyclyl, alkylaryl, haloalkyl (such as $CF_3$, —$CH_2$—$CF_3$, —$CCl_3$), —CN, aryl, heteroaryl, and combinations thereof.

"Heterocycle," "heterocyclic" and "heterocyclyl" are used interchangeably, and refer to a cyclic radical attached via a ring carbon or nitrogen atom of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, $C_1$-$C_{10}$ alkyl, phenyl or benzyl, and optionally containing 1-3 double bonds and optionally substituted with one or more substituents. Heterocyclyl are distinguished from heteroaryl by definition. Examples of heterocycles include, but are not limited to piperazinyl, piperidinyl, piperidonyl, 4-piperidonyl, dihydrofuro[2,3-b]tetrahydrofuran, morpholinyl, piperazinyl, piperidinyl, piperidonyl, 4-piperidonyl, piperonyl, pyranyl, 2H-pyrrolyl, 4H-quinolizinyl, quinuclidinyl, tetrahydrofuranyl, 6H-1,2,5-thiadiazinyl. Heterocyclic groups can optionally be substituted with one or more substituents as defined above for alkyl and aryl.

The term "heteroaryl" refers to $C_5$-$C_{26}$-membered aromatic, fused aromatic, biaromatic ring systems, or combinations thereof, in which one or more carbon atoms on one or more aromatic ring structures have been substituted with an heteroatom. Suitable heteroatoms include, but are not limited to, oxygen, sulfur, and nitrogen. Broadly defined, "heteroaryl," as used herein, includes 5-, 6-, 7-, 8-, 9-, 10-, 14-, 18-, and 24-membered single-ring aromatic groups that may include from one to four heteroatoms, for example, pyrrole, furan, thiophene, imidazole, oxazole, thiazole, triazole, tetrazole, pyrazole, pyridine, pyrazine, pyridazine and pyrimidine, and the like. The heteroaryl group may also be referred to as "aryl heterocycles" or "heteroaromatics". "Heteroaryl" further encompasses polycyclic ring systems having two or more rings in which two or more carbons are common to two adjoining rings (i.e., "fused rings") wherein at least one of the rings is heteroaromatic, e.g., the other cyclic ring or rings can be cycloalkyls, cycloalkenyls, cycloalkynyls, aryls, heterocycles, or combinations thereof. Examples of heteroaryl rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, purinyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, quinoxalinyl, tetrahydroisoquinolinyl, tetrahydroquinolinyl, tetrazolyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined below for "substituted heteroaryl".

The term "substituted heteroaryl" refers to a heteroaryl group in which one or more hydrogen atoms on one or more heteroaromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfonamido, sulfonyl, heterocyclyl, alkylaryl, haloalkyl (such as $CF_3$, —$CH_2$—$CF_3$, —$CCl_3$), —CN, aryl, heteroaryl, and combinations thereof.

"Alkyl," as used herein, refers to the radical of saturated aliphatic groups, including straight-chain alkyl, alkenyl, or alkynyl groups, branched-chain alkyl, cycloalkyl (alicyclic), alkyl substituted cycloalkylgroups, and cycloalkyl substituted alkyl. In preferred embodiments, a straight chain or branched chain alkyl has 30 or fewer carbon atoms in its backbone (e.g., $C_1$-$C_{30}$ for straight chains, $C_3$-$C_{30}$ for branched chains), preferably 20 or fewer, more preferably 15 or fewer, most preferably 10 or fewer. Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a hosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

"Alkyl" includes one or more substitutions at one or more carbon atoms of the hydrocarbon radical as well as heteroalkyls. Suitable substituents include, but are not limited to, halogens, such as fluorine, chlorine, bromine, or iodine; hydroxyl; —NRR', wherein R and R' are independently hydrogen, alkyl, or aryl, and wherein the nitrogen atom is optionally quaternized; —SR, wherein R is hydrogen, alkyl, or aryl; —CN; —$NO_2$; —COOH; carboxylate; —COR, —COOR, or —CON(R)$_2$, wherein R is hydrogen, alkyl, or aryl; azide, aralkyl, alkoxyl, imino, phosphonate, phosphinate, silyl, ether, sulfonyl, sulfonamido, heterocyclyl, aromatic or heteroaromatic moieties, haloalkyl (such as —$CF_3$, —$CH_2$—$CF_3$, —$CCl_3$); —CN; —$NCOCOCH_2CH_2$, —NCOCOCHCH; —NCS; and combinations thereof.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), haloalkyls, —CN and the like. Cycloalkyls can be substituted in the same manner.

The terms "alkenyl" and "alkynyl" refer to unsaturated aliphatic groups analogous in length and possible substitution to the alkyls described above, but that contain at least one double or triple bond, respectively.

The term "substituted alkenyl" refers to alkenyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "substituted alkynyl" refers to alkynyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "phenyl" is art recognized, and refers to the aromatic moiety —$C_6H_5$, i.e., a benzene ring without one hydrogen atom.

The term "substituted phenyl" refers to a phenyl group, as defined above, having one or more substituents replacing one or more hydrogen atoms on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

"Amino" and "Amine," as used herein, are art-recognized and refer to both substituted and unsubstituted amines, e.g., a moiety that can be represented by the general formula:

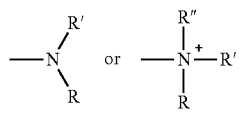

wherein, R, R', and R" each independently represent a hydrogen, substituted or unsubstituted alkyl, substituted or unsubstituted alkenyl, substituted or unsubstituted alkynyl, substituted or unsubstituted carbonyl, —$(CH_2)_m$—R''', or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of R and R' can be a carbonyl, e.g., R and R' together with the nitrogen do not form an imide. In preferred embodiments, R and R' (and optionally R") each independently represent a hydrogen atom, substituted or unsubstituted alkyl, a substituted or unsubstituted alkenyl, or —$(CH_2)_m$—R'''. Thus, the term 'alkylamine' as used herein refers to an amine group, as defined above, having a substituted or unsubstituted alkyl attached thereto (i.e. at least one of R, R', or R" is an alkyl group).

"Carbonyl," as used herein, is art-recognized and includes such moieties as can be represented by the general formula:

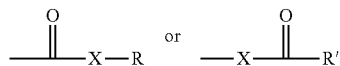

wherein X is a bond, or represents an oxygen or a sulfur, and R represents a hydrogen, a substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —$(CH_2)_m$—R", or a pharmaceutical acceptable salt, R' represents a hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl or —$(CH_2)_m$—R"; R" represents a hydroxy group, substituted or unsubstituted carbonyl group, an aryl, a cycloalkyl ring, a cycloalkenyl ring, a heterocycle, or a polycycle; and m is zero or an integer ranging from 1 to 8. Where X is oxygen and R is defines as above, the moiety is also referred to as a carboxyl group. When X is oxygen and R is hydrogen, the formula represents a 'carboxylic acid'. Where X is oxygen and R' is hydrogen, the formula represents a 'formate'. Where X is oxygen and R or R' is not hydrogen, the formula represents an "ester". In general, where the oxygen atom of the above formula is replaced by a sulfur atom, the formula represents a 'thiocarbonyl' group. Where X is sulfur and R or R' is not hydrogen, the formula represents a 'thioester.' Where X is sulfur and R is hydrogen, the formula represents a 'thiocarboxylic acid.' Where X is sulfur and R' is hydrogen, the formula represents a 'thioformate.' Where X is a bond and R is not hydrogen, the above formula represents a 'ketone.' Where X is a bond and R is hydrogen, the above formula represents an 'aldehyde.'

The term "substituted carbonyl" refers to a carbonyl, as defined above, wherein one or more hydrogen atoms in R, R' or a group to which the moiety

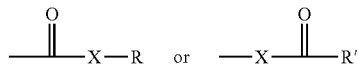

is attached, are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "carboxyl" is as defined above for the formula

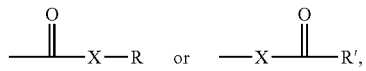

and is defined more specifically by the formula —$R^{iv}$COOH, wherein $R^{iv}$ is an alkyl, alkenyl, alkynyl, cycloalkyl, heterocyclyl, alkylaryl, arylalkyl, aryl, or heteroaryl. In preferred embodiments, a straight chain or branched chain alkyl, alkenyl, and alkynyl have 30 or fewer carbon atoms in its backbone (e.g., $C_1$-$C_{30}$ for straight chain alkyl, $C_3$-$C_{30}$ for branched chain alkyl, $C_2$-$C_{30}$ for straight chain alkenyl and alkynyl, $C_3$-$C_{30}$ for branched chain alkenyl and alkynyl), preferably 20 or fewer, more preferably 15 or fewer, most preferably 10 or fewer. Likewise, preferred cycloalkyls, heterocyclyls, aryls and heteroaryls have from 3-10 carbon atoms in their ring structure, and more preferably have 5, 6 or 7 carbons in the ring structure.

The term "substituted carboxyl" refers to a carboxyl, as defined above, wherein one or more hydrogen atoms in R are substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

"Heteroalkyl," as used herein, refers to straight or branched chain, or cyclic carbon-containing radicals, or combinations thereof, containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized.

Examples of saturated hydrocarbon radicals include, but are not limited to, methyl, ethyl, n-propyl, isopropyl, n-butyl, t-butyl, isobutyl, sec-butyl, cyclohexyl, (cyclohexyl)methyl, cyclopropylmethyl, and homologs and isomers of, for example, n-pentyl, n-hexyl, n-heptyl, n-octyl. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, and 3-butynyl.

The terms "alkoxyl" or "alkoxy," "aroxy" or "aryloxy," generally describe compounds represented by the formula —OR$^v$, wherein R$^v$ includes, but is not limited to, substituted or unsubstituted alkyl, alkenyl, alkynyl, cycloalkyl, heterocyclyl, cycloalkenyl, heterocycloalkenyl, aryl, heteroaryl, arylalkyl, heteroalkyls, alkylaryl, alkylheteroaryl.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. The term alkoxy also includes cycloalkyl, heterocyclyl, cycloalkenyl, heterocycloalkenyl, and arylalkyl having an oxygen radical attached to at least one of the carbon atoms, as valency permits.

The term "substituted alkoxy" refers to an alkoxy group having one or more substituents replacing one or more hydrogen atoms on one or more carbons of the alkoxy backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "phenoxy" is art recognized, and refers to a compound of the formula —OR' wherein R$^v$ is (i.e., —O—C$_6$H$_5$). One of skill in the art recognizes that a phenoxy is a species of the aroxy genus.

The term "substituted phenoxy" refers to a phenoxy group, as defined above, having one or more substituents replacing one or more hydrogen atoms on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The terms "aroxy" and "aryloxy," as used interchangeably herein, are represented by —O-aryl or —O-heteroaryl, wherein aryl and heteroaryl are as defined herein.

The terms "substituted aroxy" and "substituted aryloxy," as used interchangeably herein, represent —O-aryl or —O-heteroaryl, having one or more substituents replacing one or more hydrogen atoms on one or more ring atoms of the aryl and heteroaryl, as defined herein. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "alkylthio" refers to an alkyl group, as defined above, having a sulfur radical attached thereto. The "alkylthio" moiety is represented by —S-alkyl. Representative alkylthio groups include methylthio, ethylthio, and the like. The term "alkylthio" also encompasses cycloalkyl groups having a sulfur radical attached thereto.

The term "substituted alkylthio" refers to an alkylthio group having one or more substituents replacing one or more hydrogen atoms on one or more carbon atoms of the alkylthio backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "phenylthio" is art recognized, and refers to —S—C$_6$H$_5$, i.e., a phenyl group attached to a sulfur atom.

The term "substituted phenylthio" refers to a phenylthio group, as defined above, having one or more substituents replacing a hydrogen on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

"Arylthio" refers to —S-aryl or —S-heteroaryl groups, wherein aryl and heteroaryl as defined herein.

The term "substituted arylthio" represents —S-aryl or —S-heteroaryl, having one or more substituents replacing a hydrogen atom on one or more ring atoms of the aryl and heteroaryl rings as defined herein. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

"Arylalkyl," as used herein, refers to an alkyl group that is substituted with a substituted or unsubstituted aryl or heteroaryl group.

"Alkylaryl," as used herein, refers to an aryl group (e.g., an aromatic or hetero aromatic group), substituted with a substituted or unsubstituted alkyl group.

The terms "amide" or "amido" are used interchangeably, refer to both "unsubstituted amido" and "substituted amido" and are represented by the general formula:

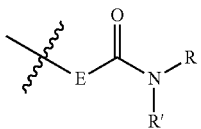

wherein, E is absent, or E is substituted or unsubstituted alkyl, substituted or unsubstituted alkenyl, substituted or unsubstituted alkynyl, substituted or unsubstituted aralkyl, substituted or unsubstituted cycloalkyl, substituted or unsubstituted aryl, substituted or unsubstituted heteroaryl, substituted or unsubstituted heterocyclyl, wherein independently of E, R and R' each independently represent a hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —$(CH_2)_m$—R''', or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of R and R' can be a carbonyl, e.g., R and R' together with the nitrogen do not form an imide. In preferred embodiments, R and R' each independently represent a hydrogen atom, substituted or unsubstituted alkyl, a substituted or unsubstituted alkenyl, or —$(CH_2)_m$—R'''. When E is oxygen, a carbamate is formed. The carbamate cannot be attached to another chemical species, such as to form an oxygen-oxygen bond, or other unstable bonds, as understood by one of ordinary skill in the art.

The term "sulfonyl" is represented by the formula

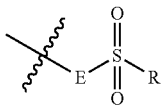

wherein E is absent, or E is alkyl, alkenyl, alkynyl, aralkyl, alkylaryl, cycloalkyl, aryl, heteroaryl, heterocyclyl, wherein independently of E, R represents a hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —$(CH_2)_m$—R''', or E and R taken together with the S atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of E and R can be substituted or unsubstituted amine, to form a "sulfonamide" or "sulfonamido." The substituted or unsubstituted amine is as defined above.

The term "substituted sulfonyl" represents a sulfonyl in which E, R, or both, are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "sulfonic acid" refers to a sulfonyl, as defined above, wherein R is hydroxyl, and E is absent, or E is substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl.

The term "sulfate" refers to a sulfonyl, as defined above, wherein E is absent, oxygen, alkoxy, aroxy, substituted alkoxy or substituted aroxy, as defined above, and R is independently hydroxyl, alkoxy, aroxy, substituted alkoxy or substituted aroxy, as defined above. When E is oxygen, the sulfate cannot be attached to another chemical species, such as to form an oxygen-oxygen bond, or other unstable bonds, as understood by one of ordinary skill in the art.

The term "sulfonate" refers to a sulfonyl, as defined above, wherein E is oxygen, alkoxy, aroxy, substituted alkoxy or substituted aroxy, as defined above, and R is independently hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —$(CH_2)_m$—R''', R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. When E is oxygen, sulfonate cannot be attached to another chemical species, such as to form an oxygen-oxygen bond, or other unstable bonds, as understood by one of ordinary skill in the art.

The term "sulfamoyl" refers to a sulfonamide or sulfonamide represented by the formula

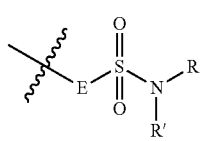

wherein E is absent, or E is substituted or unsubstituted alkyl, substituted or unsubstituted alkenyl, substituted or unsubstituted alkynyl, substituted or unsubstituted aralkyl, substituted or unsubstituted alkylaryl, substituted or unsubstituted cycloalkyl, substituted or unsubstituted aryl, substituted or unsubstituted heteroaryl, substituted or unsubstituted heterocyclyl, wherein independently of E, R and R' each independently represent a hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R''', or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of R and R' can be a carbonyl, e.g., R and R' together with the nitrogen do not form an imide.

The term "phosphonyl" is represented by the formula

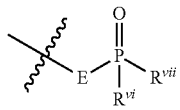

wherein E is absent, or E is substituted or unsubstituted alkyl, substituted or unsubstituted alkenyl, substituted or unsubstituted alkynyl, substituted or unsubstituted aralkyl, substituted or unsubstituted alkylaryl, substituted or unsubstituted cycloalkyl, substituted or unsubstituted aryl, substituted or unsubstituted heteroaryl, substituted or unsubstituted heterocyclyl, wherein, independently of E, R'' and R''' are independently hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R''', or R and R' taken together with the P atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8.

The term "substituted phosphonyl" represents a phosphonyl in which E, R$^{vi}$ and R$^{vii}$ are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "phosphoryl" defines a phoshonyl in which E is absent, oxygen, alkoxy, aroxy, substituted alkoxy or substituted aroxy, as defined above, and independently of E, R$^{vi}$ and R$^{vii}$ are independently hydroxyl, alkoxy, aroxy, substituted alkoxy or substituted aroxy, as defined above. When E is oxygen, the phosphoryl cannot be attached to another chemical species, such as to form an oxygen-oxygen bond, or other unstable bonds, as understood by one of ordinary skill in the art. When E, R$^{vi}$ and R$^{vii}$ are substituted, the substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "polyaryl" refers to a chemical moiety that includes two or more aryls, heteroaryls, and combinations thereof. The aryls, heteroaryls, and combinations thereof, are fused, or linked via a single bond, ether, ester, carbonyl, amide, sulfonyl, sulfonamide, alkyl, azo, and combinations thereof.

The term "substituted polyaryl" refers to a polyaryl in which one or more of the aryls, heteroaryls are substituted, with one or more substituents including, but not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof. The term "C$_3$-C$_{20}$ cyclic" refers to a substituted or unsubstituted cycloalkyl, substituted or unsubstituted cycloalkenyl, substituted or unsubstituted cycloalkynyl, substituted or unsubstituted heterocyclyl that have from three to 20 carbon atoms, as geometric constraints permit. The cyclic structures are formed from single or fused ring systems. The substituted cycloalkyls, cycloalkenyls, cycloalkynyls and heterocyclyls are substituted as defined above for the alkyls, alkenyls, alkynyls and heterocyclyls, respectively.

"Water-soluble", as used herein, generally means at least about 10 g of a substance is soluble in 1 L of water, i.e., at neutral pH, at 25° C.

The term "substituted C$_1$-C$_x$ alkyl" refers to alkyl groups having from one to x carbon atoms, wherein at least one carbon atom is substituted, wherein "x" is an integer from one to ten. The term "unsubstituted C$_1$-C$_x$ alkyl" refers to alkyl groups having from one to x carbon atoms that are not substituted, wherein "x" is an integer from one to ten.

The term "substituted C$_1$-C$_x$ alkylene" refers to alkylene groups having from one to x carbon atoms, wherein at least one carbon atom is substituted, wherein "x" is an integer from one to ten. The term "unsubstituted C$_1$-C$_x$ alkylene" refers to alkylene groups having from one to x carbon atoms that are not substituted, wherein "x" is an integer from one to ten. The term "alkylene" as used herein, refers to a moiety with the formula —(CH$_2$)$_a$—, wherein "a" is an integer from one to ten.

The term "substituted C$_2$-C$_x$ alkenyl" refers to alkenyl groups having from two to x carbon atoms, wherein at least one carbon atom is substituted, wherein "x" is an integer from two to ten. The term "unsubstituted C$_2$-C$_x$ alkenyl"

refers to alkenyl groups having from two to x carbon atoms that are not substituted, wherein "x" is an integer from two to ten.

The term "substituted $C_2$-$C_x$ alkynyl" refers to alkynyl groups having from two to x carbon atoms, wherein at least one carbon atom is substituted, wherein "x" is an integer from two to ten. The term "unsubstituted $C_2$-$C_x$ alkynyl" refers to alkynyl groups having from two to x carbon atoms that are not substituted, wherein "x" is an integer from two to ten.

The term "substituted $C_1$-$C_x$ alkoxy" refers to alkoxy groups having from one to x carbon atoms, wherein at least one carbon atom is substituted, wherein "x" is an integer from one to ten. The term "unsubstituted $C_1$-$C_x$ alkoxy" refers to alkoxy groups having from one to x carbon atoms that are not substituted, wherein "x" is an integer from one to ten.

The term "substituted $C_1$-$C_x$ alkylamino" refers to alkylamino groups having from one to x carbon atoms, wherein at least one carbon atom is substituted, wherein "x" is an integer from one to ten. The term "unsubstituted $C_1$-$C_x$ alkylamino" refers to alkyl groups having from one to x carbon atoms that are not substituted, wherein "x" is an integer from one to ten. The terms "alkylamine" and "alkylamino" are used interchangeably. In any alkylamino, where the nitrogen atom is substituted with one, two, or three substituents, the nitrogen atom can be referred to as a secondary, tertiary, or quaternary nitrogen atom, respectively.

The term "substituted $C_1$-$C_x$ alkylthio" refers to alkylthio groups having from one to x carbon atoms, wherein at least one carbon atom is substituted, wherein "x" is an integer from one to ten. The term "unsubstituted $C_1$-$C_x$ alkylthio" refers to alkylthio groups having from one to x carbon atoms that are not substituted, wherein "x" is an integer from one to ten.

The term "substituted $C_1$-$C_x$ carbonyl" refers to carbonyl groups having from one to x carbon atoms, wherein at least one carbon atom is substituted, wherein "x" is an integer from one to ten. The term "unsubstituted $C_1$-$C_x$ carbonyl" refers to carbonyl groups having from one to x carbon atoms that are not substituted, wherein "x" is an integer from one to ten.

The term "substituted $C_1$-$C_x$ carboxyl" refers to carboxyl groups having from one to x carbon atoms, wherein at least one carbon atom is substituted, wherein "x" is an integer from one to ten. The term "unsubstituted $C_1$-$C_x$ carboxyl" refers to carboxyl groups having from one to x carbon atoms that are not substituted, wherein "x" is an integer from one to ten.

The term "substituted $C_1$-$C_x$ amido" refers to amido groups having from one to x carbon atoms, wherein at least one carbon atom is substituted, wherein "x" is an integer from one to ten. The term "unsubstituted $C_1$-$C_x$ amido" refers to amido groups having from one to x carbon atoms that are not substituted, wherein "x" is an integer from one to ten.

The term "substituted $C_1$-$C_x$ sulfonyl" refers to sulfonyl groups having from one to x carbon atoms, wherein at least one carbon atom is substituted, wherein "x" is an integer from one to ten. The term "unsubstituted $C_1$-$C_x$ sulfonyl" refers to sulfonyl groups having from one to x carbon atoms that are not substituted, wherein "x" is an integer from one to ten.

The term "substituted $C_1$-$C_x$ sulfonic acid" refers to sulfonic acid groups having from one to x carbon atoms, wherein at least one carbon atom is substituted, wherein "x" is an integer from one to ten. The term "unsubstituted $C_1$-$C_x$ sulfonic acid" refers to sulfonic acid groups having from one to x carbon atoms that are not substituted, wherein "x" is an integer from one to ten.

The term "substituted $C_1$-$C_x$ sulfamoyl" refers to sulfamoyl groups having from one to x carbon atoms, wherein at least one carbon atom is substituted, wherein "x" is an integer from one to ten. The term "unsubstituted $C_1$-$C_x$ sulfamoyl" refers to sulfamoyl groups having from one to x carbon atoms that are not substituted, wherein "x" is an integer from one to ten.

The term "substituted $C_1$-$C_x$ sulfoxide" refers to sulfoxide groups having from one to x carbon atoms, wherein at least one carbon atom is substituted, wherein "x" is an integer from one to ten. The term "unsubstituted $C_1$-$C_x$ sulfoxide" refers to sulfoxide groups having from one to x carbon atoms that are not substituted, wherein "x" is an integer from one to ten.

The term "substituted $C_1$-$C_x$ phosphoryl" refers to phosphoryl groups having from one to x carbon atoms, wherein at least one carbon atom is substituted, wherein "x" is an integer from one to ten. The term "unsubstituted $C_1$-$C_x$ phosphoryl" refers to phosphoryl groups having from one to x carbon atoms that are not substituted, wherein "x" is an integer from one to ten.

The term "substituted $C_1$-$C_x$ phosphonyl" refers to phosphonyl groups having from one to x carbon atoms, wherein at least one carbon atom is substituted, wherein "x" is an integer from one to ten. The term "unsubstituted $C_1$-$C_x$ phosphonyl" refers to phosphonyl groups having from one to x carbon atoms that are not substituted, wherein "x" is an integer from one to ten.

The term "substituted $C_0$-$C_x$ sulfonyl" refers to sulfonyl groups having from zero to x carbon atoms, wherein, if present, at least one carbon atom is substituted, wherein "x" is an integer from zero to ten. The term "unsubstituted $C_0$-$C_x$ sulfonyl" refers to sulfonyl groups having from zero to x carbon atoms that are not substituted, wherein "x" is an integer from zero to ten.

The term "substituted $C_0$-$C_x$ sulfonic acid" refers to sulfonic acid groups having from zero to x carbon atoms, wherein, if present, at least one carbon atom is substituted, wherein "x" is an integer from zero to ten. The term "unsubstituted $C_0$-$C_x$ sulfonic acid" refers to sulfonic acid groups having from zero to x carbon atoms that are not substituted, wherein "x" is an integer from zero to ten.

The term "substituted $C_0$-$C_x$ sulfamoyl" refers to sulfamoyl groups having from zero to x carbon atoms, wherein, if present, at least one carbon atom is substituted, wherein "x" is an integer from zero to ten. The term "unsubstituted $C_0$-$C_x$ sulfamoyl" refers to sulfamoyl groups having from zero to x carbon atoms that are not substituted, wherein "x" is an integer from zero to ten.

The term "substituted $C_0$-$C_x$ sulfoxide" refers to sulfoxide groups having from zero to x carbon atoms, wherein at least one carbon atom is substituted, wherein "x" is an integer from zero to ten. The term "unsubstituted $C_0$-$C_x$ sulfoxide" refers to sulfoxide groups having from zero to x carbon atoms that are not substituted, wherein "x" is an integer from zero to ten.

The term "substituted $C_0$-$C_x$ phosphoryl" refers to phosphoryl groups having from zero to x carbon atoms, wherein, if present, at least one carbon atom is substituted, wherein "x" is an integer from zero to ten. The term "unsubstituted $C_0$-$C_x$ phosphoryl" refers to phosphoryl groups having from zero to x carbon atoms that are not substituted, wherein "x" is an integer from zero to ten.

The term "substituted $C_0$-$C_x$ phosphonyl" refers to phosphonyl groups having from zero to x carbon atoms, wherein, if present, at least one carbon atom is substituted, wherein "x" is an integer from zero to ten. The term "unsubstituted $C_0$-$C_x$ phosphonyl" refers to phosphonyl groups having from zero to x carbon atoms that are not substituted, wherein "x" is an integer from zero to ten.

The terms substituted "$C_x$ alkyl," "$C_x$ alkylene," "$C_x$ alkenyl," "$C_x$ alkynyl," "$C_x$ alkoxy," "$C_x$ alkylamino," "$C_x$ alkylthio," "$C_x$ carbonyl," "$C_x$ carboxyl," "$C_x$ amido," "$C_x$ sulfonyl," "$C_x$ sulfonic acid," "$C_x$ sulfamoyl," "$C_x$ phosphoryl," and "$C_x$ phosphonyl" refer to alkyl, alkylene, alkenyl, alkynyl, alkoxy, alkylamino, alkylthio, carbonyl, carboxyl, amido, sulfonyl, sulfonic acid, sulfamoyl, sulfoxide, phosphoryl, and phosphonyl groups, respectively, having x carbon atoms, wherein at least one carbon atom is substituted, wherein "x" is an integer from one to ten. The terms unsubstituted "$C_x$ alkyl," "$C_x$ alkylene," "$C_x$ alkenyl," "$C_x$ alkynyl," "$C_x$ alkoxy," "$C_x$ alkylamino", "$C_x$ alkylthio," "$C_x$ carbonyl," "$C_x$ carboxyl," "$C_x$ amido," "$C_x$ sulfonyl," "$C_x$ sulfonic acid," "$C_x$ sulfamoyl," "$C_x$ phosphoryl," and "$C_x$ phosphonyl" refer to alkyl, alkylene, alkenyl, alkynyl, alkoxy, alkylamino, alkylthio, carbonyl, carboxyl, amido, sulfonyl, sulfonic acid, sulfamoyl, sulfoxide, phosphoryl, and phosphonyl groups, respectively, having x carbon atoms that are not substituted, wherein "x" is an integer from one to ten.

II. Polymeric Materials for Encapsulating Cells

The polymers used to encapsulate the cells contain a backbone and a plurality of side chains formed by monomer subunits A and B, and optionally another monomer subunit C. Each A within the polymer is a zwitterionic monomer. The A subunits can be formed from monomers having the same zwitterion or from monomers having different zwitterions. Each B is a monomer with a reactive side chain. The B subunits can be formed from monomers having the same reactive side chain or from monomers having different reactive side chains. Each C is independently a hydrophobic monomer or a neutral hydrophilic monomer. The C subunits can be formed from the monomers with having the same hydrophobic or neutral side chain or from monomers having different hydrophobic or neutral side chains.

In some embodiments, the zwitterionic polymers can be mixed or blended with other non-zwitterionic polymers to form a mixture. The non-zwitterionic polymers can be hydrophilic, hydrophobic, or amphiphilic.

The zwitterionic polymers can be biocompatible, biodegradable, non-biodegradable, or a combination thereof. The polymers can be purified after synthesis to remove any unreacted or partially reacted contaminants present with the chemically polymeric product. The purified polymers induce a lower foreign body response than a similar polymer that has not been purified.

A. Polymer Backbone

The polymer backbone can be neutral (e.g., polyalkylene or polyether) or contain permanently charged moieties (e.g., cyclic or acyclic quaternized nitrogen atoms), or even zwitterionic backbones (e.g., phosphorylcholine backbones). Therefore, the backbone of the polymers can be formed from polymers that include, but are not limited to, poly(acrylate), poly(methacrylate), poly(acrylamide), poly(methacrylamide), poly(vinyl alcohol), poly(ethylene vinyl acetate), poly(vinyl acetate), polyolefin, polyester, polyanhydride, poly(orthoester), polyamide, polyamine, polyether, polyazine, poly(carbonate), polyetheretherketone (PEEK), polyguanidine, polyimide, polyketal, poly(ketone), polyphosphazine, polysaccharide, polysiloxane, polysulfone, polyurea, polyurethane, combinations thereof.

B. Monomers Used to Form the Polymers

1. Zwitterionic Monomers

Each zwitterionic monomer within the polymer is denoted A. The zwitterionic monomers contain carboxybetaine moieties, sulfobetaine moieties, and phosphoryl choline moieties.

The zwitterionic moieties can be represented by:

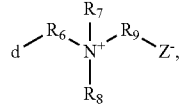

Formula I

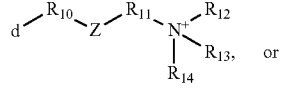

Formula II

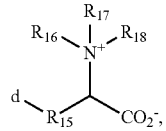

Formula III d is the point of covalent attachment of the zwitterion to the backbone of the polymer.

In some embodiments, Z can be a carboxylate, phosphate, phosphonic, phosphanate, sulfate, sulfinic, or sulfonate. The zwitterionic monomers can be provided in their zwitterionic states, as precursor monomers containing a protecting group, or combinations thereof. After the polymerization reaction, the precursor monomers can be deprotected to produce the zwitterionic monomer. For example, the precursor to a carboxybetaine monomer can be a cationic carboxybetaine ester, as shown in FIGS. 1A-1G. After polymerization the cationic carboxybetaine ester is hydrolyzed thereby converting it to the carboxybetaine, i.e., zwitterion.

In some embodiments, $R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$ are independently unsubstituted alkyl, substituted alkyl, unsubstituted alkenyl, substituted alkenyl, unsubstituted alkynyl, substituted alkynyl, unsubstituted aryl, substituted aryl, unsubstituted heteroaryl, substituted heteroaryl, unsubstituted alkoxy, substituted alkoxy, unsubstituted aroxy, substituted aroxy, unsubstituted alkylthio, substituted alkylthio, unsubstituted arylthio, substituted arylthio, unsubstituted carbonyl, substituted carbonyl, unsubstituted carboxyl, substituted carboxyl, unsubstituted amino, substituted amino, unsubstituted amido, substituted amido, unsubstituted sulfonyl, substituted sulfonyl, unsubstituted sulfamoyl, substituted sulfamoyl, unsubstituted phosphonyl, substituted phosphonyl, unsubstituted polyaryl, substituted polyaryl, unsubstituted $C_3$-$C_{20}$ cyclic, substituted $C_3$-$C_{20}$ cyclic, unsubstituted $C_3$-$C_{20}$ heterocyclic, substituted $C_3$-$C_{20}$ heterocyclic, amino acid, poly(ethylene glycol), poly(lactic-co-glycolic acid), peptide, or polypeptide group.

In some embodiments, $R_6$-$R_{18}$ are independently unsubstituted $C_1$-$C_{10}$ alkyl, substituted $C_1$-$C_{10}$ alkyl, unsubstituted $C_1$-$C_{10}$ alkenyl, substituted $C_1$-$C_{10}$ alkylene, unsubstituted $C_1$-$C_{10}$ alkylene, substituted $C_1$-$C_{10}$ alkenyl, unsubstituted $C_1$-$C_{10}$ alkynyl, substituted $C_1$-$C_{10}$ alkynyl, unsubstituted aryl, substituted aryl, unsubstituted heteroaryl, substituted heteroaryl, unsubstituted $C_1$-$C_{10}$ alkoxy, substituted $C_1$-$C_{10}$ alkoxy, unsubstituted aroxy, substituted aroxy, unsubstituted $C_1$-$C_{10}$ alkylthio, substituted $C_1$-$C_{10}$ alkylthio, unsubstituted arylthio, substituted arylthio, unsubstituted $C_1$-$C_{10}$ carbonyl, substituted $C_1$-$C_{10}$ carbonyl, unsubstituted $C_1$-$C_{10}$ carboxyl, substituted $C_1$-$C_{10}$ carboxyl, unsubstituted $C_1$-$C_{10}$ amino, substituted $C_1$-$C_{10}$ amino, unsubstituted $C_1$-$C_{10}$ amido, substituted $C_1$-$C_{10}$ amido, unsubstituted $C_1$-$C_{10}$ sulfonyl, substituted $C_1$-$C_{10}$ sulfonyl, unsubstituted $C_1$-$C_{10}$ sulfamoyl, substituted $C_1$-$C_{10}$ sulfamoyl, unsubstituted $C_1$-$C_{10}$ phosphonyl, substituted $C_1$-$C_{10}$ phosphonyl, unsubstituted polyaryl, substituted polyaryl, unsubstituted $C_3$-$C_{20}$ cyclic, substituted $C_3$-$C_{20}$ cyclic, unsubstituted $C_3$-$C_{20}$ heterocyclic, or substituted $C_3$-$C_{20}$ heterocyclic.

In some embodiments, $R_6$-$R_{18}$ are unsubstituted $C_1$-$C_5$ alkyl, substituted $C_1$-$C_5$ alkyl, unsubstituted $C_1$-$C_5$ alkenyl, substituted $C_1$-$C_5$ alkylene, unsubstituted $C_1$-$C_5$ alkylene, substituted $C_1$-$C_5$ alkenyl, unsubstituted $C_1$-$C_5$ alkynyl, substituted $C_1$-$C_5$ alkynyl, unsubstituted aryl, substituted aryl, unsubstituted heteroaryl, substituted heteroaryl, unsubstituted $C_1$-$C_5$ alkoxy, substituted $C_1$-$C_5$ alkoxy, unsubstituted aroxy, substituted aroxy, unsubstituted $C_1$-$C_5$ alkylthio, substituted $C_1$-$C_5$ alkylthio, unsubstituted arylthio, substituted arylthio, unsubstituted $C_1$-$C_5$ carbonyl, substituted $C_1$-$C_5$ carbonyl, unsubstituted $C_1$-$C_5$ carboxyl, substituted $C_1$-$C_5$ carboxyl, unsubstituted $C_1$-$C_5$ amino, substituted $C_1$-$C_5$ amino, unsubstituted $C_1$-$C_5$ amido, substituted C amido, unsubstituted C sulfonyl, substituted $C_1$-$C_5$ sulfonyl, unsubstituted $C_1$-$C_5$ sulfamoyl, substituted C sulfamoyl, unsubstituted $C_1$-$C_5$ phosphonyl, substituted $C_1$-$C_5$ phosphonyl, unsubstituted polyaryl, substituted polyaryl, unsubstituted $C_3$-$C_{10}$ cyclic, substituted $C_3$-$C_{10}$ cyclic, unsubstituted $C_3$-$C_{10}$ heterocyclic, or substituted $C_3$-$C_{20}$ heterocyclic.

In some embodiments, $R_6$, $R_9$, $R_{10}$, $R_{11}$ and $R_{15}$, are independently unsubstituted $C_1$-$C_5$ alkyl, substituted $C_1$-$C_5$ alkyl, substituted $C_1$-$C_5$ alkylene, or unsubstituted C alkylene, $C_1$-$C_5$ alkoxy, substituted C alkoxy, unsubstituted aroxy, substituted aroxy, unsubstituted C alkylthio, substituted $C_1$-$C_5$ alkylthio, unsubstituted arylthio, substituted arylthio, unsubstituted C carbonyl, substituted $C_1$-$C_5$ carbonyl, unsubstituted $C_1$-$C_5$ carboxyl, substituted $C_1$-$C_5$ carboxyl, unsubstituted $C_1$-$C_5$ amino, substituted $C_1$-$C_5$ amino, unsubstituted C amido, substituted $C_1$-$C_5$ amido, unsubstituted C sulfonyl, substituted C sulfonyl, unsubstituted C sulfamoyl, substituted $C_1$-$C_5$ sulfamoyl, unsubstituted $C_1$-$C_5$ phosphonyl, or substituted $C_1$-$C_5$ phosphonyl.

In some embodiments, $R_7$, $R_8$, $R_{12}$, $R_{13}$, $R_{14}$, $R_{16}$, $R_{17}$, and $R_{18}$, are independently hydrogen, unsubstituted $C_1$-$C_5$ alkyl, or substituted $C_1$-$C_5$ alkyl.

In some embodiments, the zwitterionic moieties can be:

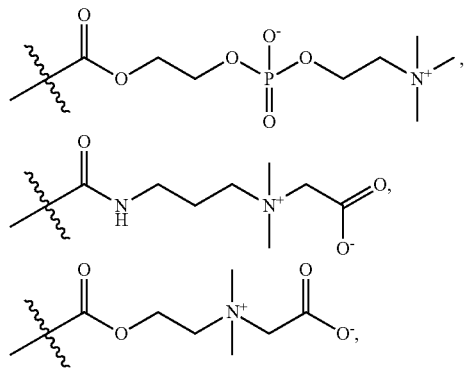

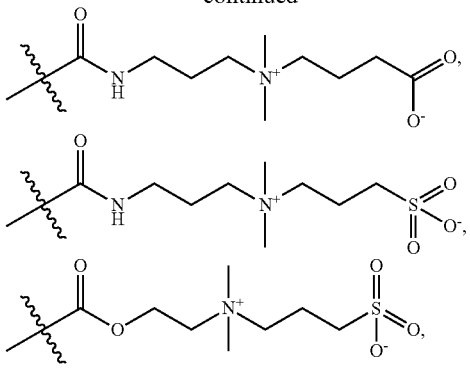

or combinations thereof.

2. Monomers with a Reactive Side Chain

Each reactive side chain within the polymer is denoted B. The reactive side chains can be represented by the formula:

$$d\text{-}R_1\text{—}Y, \quad \text{Formula IV}$$

d is the point of covalent attachment of the reactive side chain to the backbone of the polymer.

In some embodiments, $R_1$ is unsubstituted alkyl, substituted alkyl, unsubstituted alkenyl, substituted alkenyl, unsubstituted alkynyl, substituted alkynyl, unsubstituted aryl, substituted aryl, unsubstituted heteroaryl, substituted heteroaryl, unsubstituted alkoxy, substituted alkoxy, unsubstituted aroxy, substituted aroxy, unsubstituted alkylthio, substituted alkylthio, unsubstituted arylthio, substituted arylthio, unsubstituted carbonyl, substituted carbonyl, unsubstituted carboxyl, substituted carboxyl, unsubstituted amino, substituted amino, unsubstituted amido, substituted amido, unsubstituted sulfonyl, substituted sulfonyl, unsubstituted sulfamoyl, substituted sulfamoyl, unsubstituted phosphonyl, substituted phosphonyl, unsubstituted polyaryl, substituted polyaryl, unsubstituted $C_3$-$C_{20}$ cyclic, substituted $C_3$-$C_{20}$ cyclic, unsubstituted $C_3$-$C_{20}$ heterocyclic, substituted $C_3$-$C_{20}$ heterocyclic, amino acid, poly(ethylene glycol), poly(lactic-co-glycolic acid), peptide, or polypeptide group.

In some embodiments, $R_1$ is -Aq-unsubstituted $C_1$-$C_{10}$ alkylene-Bq-unsubstituted $C_1$-$C_{10}$ alkylene-, Aq-unsubstituted $C_1$-$C_{10}$ alkylene-Bq-substituted $C_1$-$C_{10}$ alkylene-, -Aq-substituted $C_1$-$C_{10}$ alkylene-Bq-unsubstituted $C_1$-$C_{10}$ alkylene-, or Aq-substituted $C_1$-$C_{10}$ alkylene-Bq-substituted $C_1$-$C_{10}$ alkylene-, wherein Aq and Bq are independently —C(O)O—, —C(O)NH—, —OC(O)—, —NHC(O)—, —O—, —NH—NHC(O)—, —OC(O)NH—, —NHC(O)O—, —C(O)—, —OC(O)O—, —S($=O_2$)$_2$—, —S($=$O)—, —S—, —N$=$N—, or —N$=$CH—.

In some embodiments, $R_1$ is -Aq-unsubstituted $C_1$-$C_5$ alkylene-Bq-unsubstituted $C_1$-$C_5$ alkylene-, Aq-unsubstituted $C_1$-$C_5$ alkylene-Bq-substituted $C_1$-$C_5$ alkylene-, -Aq-substituted $C_1$-$C_5$ alkylene-Bq-unsubstituted $C_1$-$C_5$ alkylene-, or Aq-substituted $C_1$-$C_5$ alkylene-Bq-substituted $C_1$-$C_5$ alkylene-, wherein Aq and Bq are independently —C(O)O—, —C(O)NH—, —OC(O)—, —NHC(O)—, —NH—NHC(O)—, —OC(O)NH—, —NHC(O)O—, —C(O)—, —OC(O)O—, —S($=O_2$)$_2$—, —S($=$O)—, —S—, —N$=$N—, or —N$=$CH—.

In some embodiments, $R_1$ is —C(O)O-unsubstituted $C_2$ alkylene-NHC(O)-unsubstituted $C_4$ alkylene-, —C(O)O-unsubstituted $C_2$ alkylene-NHC(O)-substituted $C_4$ alkylene-, —C(O)O-substituted $C_2$ alkylene-NHC(O)-unsubstituted $C_4$ alkylene-, or —C(O)O-substituted $C_2$ alkylene-NHC(O)-substituted $C_4$ alkylene-.

In some embodiments, Y is propane-1,3-dithiol, 1,2-dithiolan-3-yl, 1,2-dithiol-3-ylidene, hydrogen, —SH, maleimide, aziridine, —$N_3$, —CN, acryloyl, acrylamide, —C(O)O$R_2$, —C(O)$R_3$, vinyl sulfone, —OH, cyanate, thiocyanate, isocyanate, isothiocyanate, alkoxysilane, vinyl silane, silicon hydride, —$NR_4R_5$, acetohydrazide, acyl azide, acyl halides, N-hydroxysuccinimide ester, sulfonyl chloride, glyoxal, epoxide, carbodiimides, aryl halides, imido ester.

In some embodiments, $R_1$ is unsubstituted alkyl, substituted alkyl, unsubstituted alkenyl, substituted alkenyl, unsubstituted alkynyl, substituted alkynyl, unsubstituted aryl, substituted aryl, unsubstituted heteroaryl, substituted heteroaryl, unsubstituted alkoxy, unsubstituted aroxy, substituted aroxy, unsubstituted alkylthio, substituted alkylthio, unsubstituted arylthio, substituted arylthio, unsubstituted carbonyl, unsubstituted carboxyl, unsubstituted amido, unsubstituted sulfonyl, substituted sulfonyl, unsubstituted sulfamoyl, substituted sulfamoyl, unsubstituted phosphonyl, substituted phosphonyl, unsubstituted polyaryl, substituted polyaryl, unsubstituted $C_3$-$C_{20}$ cyclic, substituted $C_3$-$C_{20}$ cyclic, unsubstituted $C_3$-$C_{20}$ heterocyclic, substituted $C_3$-$C_{20}$ heterocyclic, amino acid, poly(lactic-co-glycolic acid), peptide, or polypeptide group; and Y is propane-1,3-dithiol, 1,2-dithiolan-3-yl, 1,2-dithiol-3-ylidene, hydrogen, —SH, maleimide, aziridine, —$N_3$, —CN, acryloyl, acrylamide, —C(O)O$R_2$, —C(O)$R_3$, vinyl sulfone, —OH, cyanate, thiocyanate, isocyanate, isothiocyanate, alkoxysilane, vinyl silane, silicon hydride, —$NR_4R_5$, acetohydrazide, acyl azide, acyl halides, N-hydroxysuccinimide ester, sulfonyl chloride, glyoxal, epoxide, carbodiimides, aryl halides, imido ester, or $R_1$ is unsubstituted alkyl, substituted alkyl, unsubstituted alkenyl, substituted alkenyl, unsubstituted alkynyl, substituted alkynyl, unsubstituted aryl, substituted aryl, unsubstituted heteroaryl, substituted heteroaryl, unsubstituted alkoxy, substituted alkoxy, unsubstituted aroxy, substituted aroxy, unsubstituted alkylthio, substituted alkylthio, unsubstituted arylthio, substituted arylthio, unsubstituted carbonyl, substituted carbonyl, unsubstituted carboxyl, substituted carboxyl, unsubstituted amino, substituted amino, unsubstituted amido, substituted amido, unsubstituted sulfonyl, substituted sulfonyl, unsubstituted sulfamoyl, substituted sulfamoyl, unsubstituted phosphonyl, substituted phosphonyl, unsubstituted polyaryl, substituted polyaryl, unsubstituted $C_3$-$C_{20}$ cyclic, substituted $C_3$-$C_{20}$ cyclic, unsubstituted $C_3$-$C_{20}$ heterocyclic, substituted $C_3$-$C_{20}$ heterocyclic, amino acid, poly(ethylene glycol), poly(lactic-co-glycolic acid), peptide, or polypeptide group; and Y is propane-1,3-dithiol, 1,2-dithiolan-3-yl, 1,2-dithiol-3-ylidene, —SH, maleimide, aziridine, —$N_3$, —CN, acrylamide, —C(O)O$R_2$, —C(O)$R_3$, vinyl sulfone, cyanate, thiocyanate, isocyanate, isothiocyanate, vinyl silane, silicon hydride, acetohydrazide, acyl azide, acyl halides, N-hydroxysuccinimide ester, sulfonyl chloride, glyoxal, carbodiimides, aryl halides, imido ester.

$R_2$, $R_4$, and $R_5$, are, independently, hydrogen, amino, hydroxyl, thiol, oxo, phosphate, or substituted or unsubstituted $C_1$-$C_{10}$ alkyl, substituted or unsubstituted $C_1$-$C_{10}$ alkylene, substituted or unsubstituted $C_2$-$C_{10}$ alkenyl, substituted or unsubstituted $C_2$-$C_{10}$ alkynyl, substituted or unsubstituted $C_1$-$C_{10}$ alkoxy, substituted or unsubstituted $C_1$-$C_{10}$ alkylamino, substituted or unsubstituted $C_1$-$C_{10}$ alkylthio, unsubstituted aryl, substituted aryl, unsubstituted heteroaryl, substituted heteroaryl, unsubstituted alkoxy, substituted alkoxy, unsubstituted aroxy, substituted aroxy, unsubstituted alkylthio, substituted alkylthio, unsubstituted arylthio, substituted arylthio, unsubstituted carbonyl, substituted carbonyl, unsubstituted carboxyl, substituted carboxyl, unsubstituted amino, substituted amino, unsubstituted amido, substituted amido, unsubstituted polyaryl, substituted polyaryl, unsubstituted $C_3$-$C_{20}$ cyclic, substituted $C_3$-$C_{20}$ cyclic, unsubstituted $C_3$-$C_{20}$ heterocyclic, or substituted $C_3$-$C_{20}$ heterocyclic; and wherein $R_3$ is hydrogen, amino, hydroxyl, thiol, oxo, phosphate, or substituted or unsubstituted $C_1$-$C_{10}$ alkyl, substituted or unsubstituted $C_1$-$C_{10}$ alkylene, substituted or unsubstituted $C_2$-$C_{10}$ alkenyl, substituted or unsubstituted $C_2$-$C_{10}$ alkynyl, substituted or unsubstituted $C_1$-$C_{10}$ alkoxy, substituted or unsubstituted $C_1$-$C_{10}$ alkylamino, substituted or unsubstituted $C_1$-$C_{10}$ alkylthio, unsubstituted aryl, substituted aryl, unsubstituted heteroaryl, substituted heteroaryl, unsubstituted alkoxy, substituted alkoxy, unsubstituted aroxy, substituted aroxy, unsubstituted alkylthio, substituted alkylthio, unsubstituted arylthio, substituted arylthio, unsubstituted carbonyl, substituted carbonyl, unsubstituted carboxyl, substituted carboxyl, unsubstituted amino, substituted amino, unsubstituted amido, substituted amido, unsubstituted polyaryl, substituted polyaryl, unsubstituted $C_3$-$C_{20}$ cyclic, substituted $C_3$-$C_{20}$ cyclic, unsubstituted $C_3$-$C_{20}$ heterocyclic, or substituted $C_3$-$C_{20}$ heterocyclic.

3. Hydrophobic Monomer

The polymers optionally contain a hydrophobic monomer with a hydrophobic side chain, represented by:

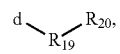

Formula V d is the point of covalent attachment of the hydrophobic side chain to the backbone of the polymer.

In some embodiments, $R_{19}$ and $R_{20}$ are independently unsubstituted alkyl, substituted alkyl, unsubstituted alkenyl, substituted alkenyl, unsubstituted alkynyl, substituted alkynyl, unsubstituted aryl, substituted aryl, unsubstituted heteroaryl, substituted heteroaryl, unsubstituted alkoxy, substituted alkoxy, unsubstituted aroxy, substituted aroxy, unsubstituted alkylthio, substituted alkylthio, unsubstituted arylthio, substituted arylthio, unsubstituted carbonyl, substituted carbonyl, unsubstituted carboxyl, substituted carboxyl, unsubstituted amino, substituted amino, unsubstituted amido, substituted amido, unsubstituted sulfonyl, substituted sulfonyl, unsubstituted sulfamoyl, substituted sulfamoyl, unsubstituted phosphonyl, substituted phosphonyl, —O—, —S—, —NH—NHC(O)—, —N=N—, —N=CH—, unsubstituted polyaryl, substituted polyaryl, unsubstituted $C_3$-$C_{20}$ cyclic, substituted $C_3$-$C_{20}$ cyclic, unsubstituted $C_3$-$C_{20}$ cyclic heterocyclic, substituted $C_3$-$C_{20}$ cyclic heterocyclic, amino acid, poly(ethylene glycol), poly(lactic-co-glycolic acid), peptide, or polypeptide group.

In some embodiments, $R_{19}$ is —C(O)NH—, —C(O)O—, —NHC(O)—, —OC(O)—, —O—, —NH—NHC(O)—, —OC(O)NH—, —NHC(O)O—, —C(O)—, —OC(O)O—, —S(=$O_2$)$_2$—, —S(=O)—, —S—, —N=N—, or —N=CH—.

In some embodiments, $R_{20}$ has the structure:

-Az-Bz-(-Cz)δ,   Formula VII wherein δ is an integer between 0 and 10, inclusive, preferably δ is 1.

In some embodiments of Formula VII, Az can be:

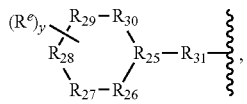

Formula VIII wherein $R_{31}$ in Az is $-(CR_{32}R_{32})_p-$; p is an integer from 0 to 5; each $R_{32}$ is hydrogen, unsubstituted alkyl, or substituted alkyl; each $R^e$ is independently unsubstituted alkyl, substituted alkyl, unsubstituted alkenyl, unsubstituted alkenyl, unsubstituted alkynyl, substituted alkynyl, unsubstituted alkoxy, substituted alkoxy, unsubstituted alkylamino, substituted alkylamino, unsubstituted dialkylamino, substituted dialkylamino, hydroxy, unsubstituted aryl, substituted aryl, unsubstituted heteroaryl, substituted heteroaryl, unsubstituted carboxyl, substituted carboxyl, unsubstituted amino, substituted amino, unsubstituted amido, substituted amido, unsubstituted $C_3$-$C_{20}$ cyclic, substituted $C_3$-$C_{20}$ cyclic, unsubstituted $C_3$-$C_{20}$ heterocyclic, or substituted $C_3$-$C_{20}$ heterocyclic; y is an integer between 0 and 11, inclusive; $R_{25}$, $R_{26}$, $R_{27}$, $R_{28}$, $R_{29}$, and $R_{30}$ are independently C or N, wherein the bonds between adjacent $R_{25}$ to $R_{30}$ are double or single according to valency, and wherein $R_{25}$ to $R_{30}$ are bound to none, one, or two hydrogens according to valency.

In some embodiments of Formula VIII, each $R_{32}$ is hydrogen, and p is 1.

In some embodiments of Formula VIII, each $R_{32}$ is hydrogen, p is 1, $R_{25}$ is C, and $R_{26}$-$R_{30}$ are CH, and the bonds between $R_{25}$ and $R_{26}$, between $R_{27}$ and $R_{28}$, and between $R_{29}$ and $R_{30}$ are double bonds.

In some embodiments of Formula VIII, each $R_{32}$ is hydrogen, p is 1, $R_{25}$ is C, and $R_{26}$-$R_{30}$ are CH, and the bonds between $R_{25}$ and $R_{26}$, between $R_{27}$ and $R_{28}$, and between $R_{29}$ and $R_{30}$ are double bonds, and y is 1.

In some embodiments of Formula VIII, each $R_{32}$ is hydrogen, p is 1, $R_{25}$ is C, and $R_{26}$-$R_{30}$ are CH, and the bonds between $R_{25}$ and $R_{26}$, between $R_{27}$ and $R_{28}$, and between $R_{29}$ and $R_{30}$ are double bonds, y is 1, and $R^e$ is Bz.

In some embodiments of Formula VIII, each $R_{32}$ is hydrogen, p is 1, $R_{25}$ is C, and $R_{26}$-$R_{30}$ are CH, and the bonds between $R_{25}$ and $R_{26}$, between $R_{27}$ and $R_{28}$, and between $R_{29}$ and $R_{30}$ are double bonds, y is 1, and $R^e$ contains a substituted heteroaryl group.

In some embodiments of Formula VIII, each $R_{32}$ is hydrogen, p is 1, $R_{25}$ is C, and $R_{26}$-$R_{30}$ are CH, and the bonds between $R_{25}$ and $R_{26}$, between $R_{27}$ and $R_{28}$, and between $R_{29}$ and $R_{30}$ are double bonds, y is 1, $R^e$ contains a substituted heteroaryl group, wherein the substituted heteroaryl group is a substituted triazole.

In some embodiments of Formula VII, Az can be:

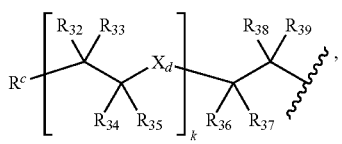

Formula IX wherein $R_{32}$, $R_{33}$, $R_{34}$, $R_{35}$, $R_{36}$, $R_{37}$, $R_{38}$, and $R_{39}$ in Az are independently hydrogen, unsubstituted alkyl, substituted alkyl, unsubstituted alkenyl, substituted alkenyl, unsubstituted alkynyl, substituted alkynyl, unsubstituted phenyl, substituted phenyl, unsubstituted aryl, substituted aryl, unsubstituted heteroaryl, substituted heteroaryl, unsubstituted arylalkyl, substituted arylalkyl, unsubstituted alkoxy, substituted alkoxy, unsubstituted aroxy, substituted aroxy, unsubstituted carbonyl, substituted carbonyl, unsubstituted carboxyl, substituted carboxyl, unsubstituted amino, substituted amino, unsubstituted amido, substituted amido, unsubstituted $C_3$-$C_{20}$ cyclic, substituted $C_3$-$C_{20}$ cyclic, unsubstituted $C_3$-$C_{20}$ heterocyclic, substituted $C_3$-$C_{20}$ heterocyclic, poly(ethylene glycol), or poly(lactic-co-glycolic acid); k is an integer from 0 to 20; each $X_d$ is independently absent, 0, or S; and $R^c$ can be Bz.

In some embodiments of Formula IX, Xd is O. In some embodiments of Formula IX, Xd is O, and $R_{32}$-$R_{39}$ are hydrogen.

In some embodiments of Formula IX, Xd is O, $R_{32}$-$R_{39}$ are hydrogen, and k is an integer between 1 and 5, inclusive, preferably 3.

In some embodiments of Formula VII or IX, Bz can be:

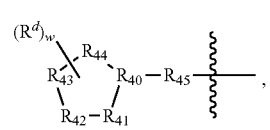

Formula X wherein $R_{45}$ in Bz is $-(CR_{46}R_{46})_p-$; p is an integer from 0 to 5; each $R_{46}$ is hydrogen, unsubstituted alkyl, or substituted alkyl; each $R^d$ is independently unsubstituted alkyl, substituted alkyl, unsubstituted alkenyl, unsubstituted alkenyl, unsubstituted alkynyl, substituted alkynyl, unsubstituted alkoxy, substituted alkoxy, unsubstituted alkylamino, substituted alkylamino, unsubstituted dialkylamino, substituted dialkylamino, hydroxy, unsubstituted aryl, substituted aryl, unsubstituted heteroaryl, substituted heteroaryl, unsubstituted carboxyl, substituted carboxyl, unsubstituted amino, substituted amino, unsubstituted amido, substituted amido, unsubstituted $C_3$-$C_{20}$ cyclic, substituted $C_3$-$C_{20}$ cyclic, unsubstituted $C_3$-$C_{20}$ heterocyclic, or substituted $C_3$-$C_{20}$ heterocyclic; w is an integer between 0 and 4, inclusive; each $R_{40}$, $R_{41}$, $R_{42}$, $R_{43}$, and $R_{44}$, are independently C or N, wherein the bonds between adjacent $R_{40}$ to $R_{44}$ are double or single according to valency, and wherein $R_{40}$ to $R_{44}$ are bound to none, one, or two hydrogens according to valency.

In some embodiments of Formula X, p is 0.

In some embodiments of Formula X, p is 0, and $R_{40}$-$R_{42}$ are N.

In some embodiments of Formula X, p is 0, $R_{40}$-$R_{42}$ are N, and $R_{43}$ and $R_{44}$ are C.

In some embodiments, Formula X is:

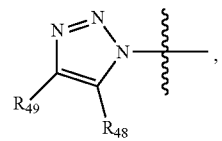

Formula XI wherein $R_{48}$ and $R_{49}$ are independently hydrogen,

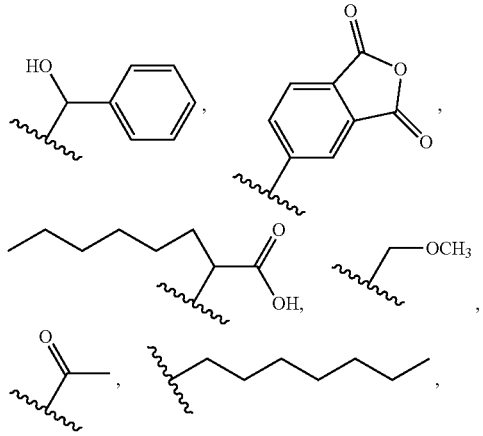

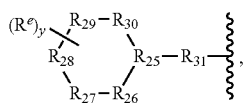

or Cz, with the proviso that at least one of $R_{48}$ and $R_{49}$ is not hydrogen.

In some embodiments of Formula VII or Formula XI, Cz can be:

Formula VIII wherein $R_{31}$ in Cz is —$(CR_{32}R_{32})_p$— or —$(CR_{32}R_{32})_p$—$X_b$—$(CR_{32}R_{32})_q$—; p and q are independently integers between 0 to 5, inclusive; each $R_{32}$ is hydrogen, unsubstituted alkyl, or substituted alkyl; $X_b$ is absent, —O—, —S—, —S(O)$_2$—, or $NR_{47}$; $R_{47}$ is unsubstituted alkyl or substituted alkyl; each $R^e$ is independently unsubstituted alkyl, substituted alkyl, unsubstituted alkenyl, unsubstituted alkenyl, unsubstituted alkynyl, substituted alkynyl, unsubstituted alkoxy, substituted alkoxy, unsubstituted alkylamino, substituted alkylamino, unsubstituted dialkylamino, substituted dialkylamino, hydroxy, unsubstituted aryl, substituted aryl, unsubstituted heteroaryl, substituted heteroaryl, unsubstituted carboxyl, substituted carboxyl, unsubstituted amino, substituted amino, unsubstituted amido, substituted amido, unsubstituted $C_3$-$C_{20}$ cyclic, substituted $C_3$-$C_{20}$ cyclic, unsubstituted $C_3$-$C_{20}$ heterocyclic, or substituted $C_3$-$C_{20}$ heterocyclic; y is an integer between 0 and 11, inclusive; $R_{25}$, $R_{26}$, $R_{27}$, $R_{28}$, $R_{29}$, and $R_{30}$ are independently C or N, wherein the bonds between adjacent $R_{25}$ to $R_{30}$ are double or single according to valency, and wherein $R_{25}$ to $R_{30}$ are bound to none, one, or two hydrogens according to valency.

In some embodiments of Formula VIII, $R_{31}$ is —$(CR_{32}R_{32})_p$—, each $R_{32}$ is hydrogen, and p is 1.

In some embodiments of Formula VIII, $R_{31}$ is —$(CR_{32}R_{32})_p$—, each $R_{32}$ is hydrogen, p is 1, and $R_{25}$ is N.

In some embodiments of Formula VIII, $R_{31}$ is —$(CR_{32}R_{32})_p$—, each $R_{32}$ is hydrogen, p is 1, $R_{25}$ is N, and $R_{28}$ is S(O)$_2$.

In some embodiments of Formula VIII, $R_{31}$ is —$(CR_{32}R_{32})_p$—, each $R_{32}$ is hydrogen, p is 1, $R_{25}$ is N, $R_{28}$ is S(O)$_2$, and $R_{26}$, $R_{27}$, $R_{29}$, and $R_{30}$ are CH$_2$.

In some embodiments of Formula VIII, $R_{31}$ is —$(CR_{32}R_{32})_p$—, each $R_{32}$ is hydrogen, p is 1, $R_{25}$ is N, $R_{28}$ is S(O)$_2$, $R_{26}$, $R_{27}$, $R_{29}$, and $R_{30}$ are CH$_2$, and y is 0, i.e.,

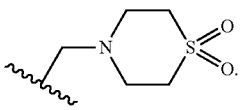 [SMILES: *CN1CCS(=O)(=O)CC1]

In some embodiments of Formula VIII, $R_{31}$ is —$(CR_{32}R_{32})_p$—$X_b$—$(CR_{32}R_{32})_q$—, each $R_{32}$ is hydrogen, and p is 0.

In some embodiments of Formula VIII, $R_{31}$ is —$(CR_{32}R_{32})_p$—$X_b$—$(CR_{32}R_{32})_q$—, each $R_{32}$ is hydrogen, p is 0, and q is 1.

In some embodiments of Formula VIII, $R_{31}$ is —$(CR_{32}R_{32})_p$—$X_b$—$(CR_{32}R_{32})_q$—, each $R_{32}$ is hydrogen, p is 0, q is 1, and $X_b$ is O or —S(O)$_2$—.

In some embodiments of Formula VIII, $R_{31}$ is —$(CR_{32}R_{32})_p$—$X_b$—$(CR_{32}R_{32})_q$—, each $R_{32}$ is hydrogen, p is 0, q is 1, $X_b$ is O, and $R_{26}$ is O.

In some embodiments of Formula VIII, $R_{31}$ is —$(CR_{32}R_{32})_p$—$X_b$—$(CR_{32}R_{32})_q$, each $R_{32}$ is hydrogen, p is 0, q is 1, $X_b$ is O, $R_{26}$ is O, and $R_{25}$ is CH.

In some embodiments of Formula VIII, $R_{31}$ is —$(CR_{32}R_{32})_p$—$X_b$—$(CR_{32}R_{32})_q$, each $R_{32}$ is hydrogen, p is 0, q is 1, $X_b$ is O, $R_{26}$ is O, $R_{25}$ is CH, $R_{27}$-$R_{30}$ are CH$_2$, and y is 0, i.e.,

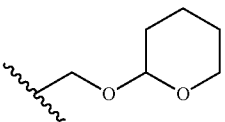

In some embodiments of Formula VIII, $R_{31}$ is —$(CR_{32}R_{32})_p$—$X_b$—$(CR_{32}R_{32})_q$, each $R_{32}$ is hydrogen, p is 0, q is 1, $X_b$ is —S(O)$_2$—, $R_{25}$ is C, $R_{26}$-$R_{30}$ are CH, and the bonds between $R_{25}$ and $R_{26}$, between $R_{27}$ and $R_{28}$, and between $R_{29}$ and $R_{30}$ are double bonds, i.e.,

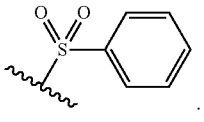

In some embodiments of Formula VIII, $R_{31}$ is —$(CR_{32}R_{32})_p$—, and p is 0. In some embodiments of Formula VIII, $R_{31}$ is —$(CR_{32}R_{32})_p$—, p is 0, $R_{25}$ is C, and $R_{26}$-$R_{30}$ are CH, and the bonds between $R_{25}$ and $R_{26}$, between $R_{27}$ and $R_{28}$, and between $R_{29}$ and $R_{30}$ are double bonds.

In some embodiments of Formula VIII, $R_{31}$ is —$(CR_{32}R_{32})_p$—, p is 0, $R_{25}$ is C, and $R_{26}$-$R_{30}$ are CH, the bonds between $R_{25}$ and $R_{26}$, between $R_{27}$ and $R_{28}$, and between $R_{29}$ and $R_{30}$ are double bonds, and y is 0 or 1.

In some embodiments of Formula VIII, $R_{31}$ is —$(CR_{32}R_{32})_p$—, p is 0, $R_{25}$ is C, and $R_{26}$-$R_{30}$ are CH, the bonds between $R_{25}$ and $R_{26}$, between $R_{27}$ and $R_{28}$, and between $R_{29}$ and $R_{30}$ are double bonds, y is 1, and $R^e$ is —NH$_2$, —OCH$_3$, or —CH$_2$OH, i.e.,

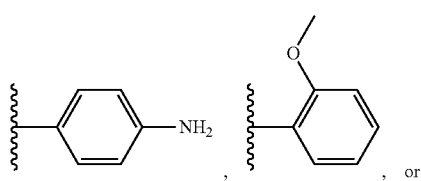

,

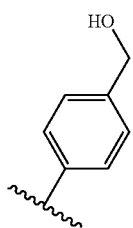

, respectively.

In some embodiments of Formula VIII, $R_{31}$ is —$(CR_{32}R_{32})_p$—, p is 0, $R_{25}$ is C, $R_{27}$ is N, $R_{26}$, $R_{28}$-$R_{30}$ are CH, the bonds between $R_{25}$ and $R_{26}$, between $R_{27}$ and $R_{28}$, and between $R_{29}$ and $R_{30}$ are double bonds, and y is 0, i.e.,

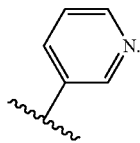 [SMILES: *c1cccnc1]

In some embodiments of Formula VIII, $R_{31}$ is —$(CR_{32}R_{32})_p$—, p is 0, $R_{25}$ is C(OH), and $R_{26}$-$R_{30}$ are $CH_2$, and y is 0, i.e.,

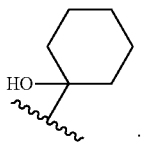

In some embodiments, the hydrophobic monomeric unit contains the moiety:

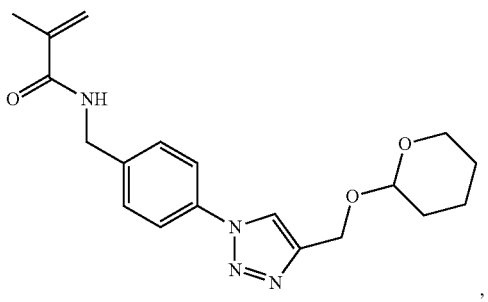

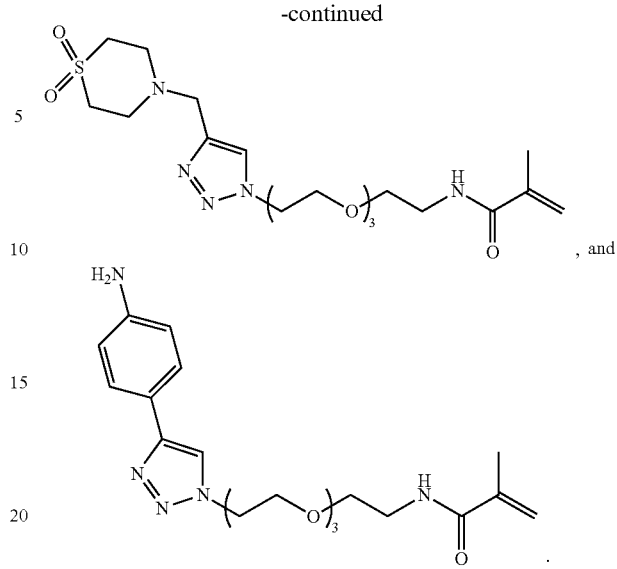

, and

4. Neutral Hydrophilic Monomer

The polymers optionally contain a neutral hydrophilic monomer with a hydrophilic side chain represented by:

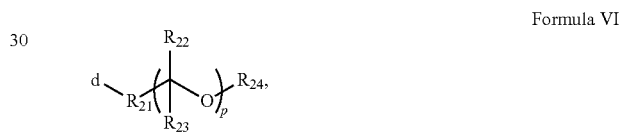

Formula VI wherein, d is the point of covalent attachment of the neutral hydrophilic side chain to the backbone of the polymer; and p is an integer between 1 and 10,000, inclusive, preferably between 1 and 30, inclusive.

In some embodiments of Formula VI, the $R_{21}$ is unsubstituted alkyl, substituted alkyl, unsubstituted alkenyl, substituted alkenyl, a unsubstituted alkynyl, substituted alkynyl, unsubstituted aryl, substituted aryl, unsubstituted heteroaryl, substituted heteroaryl, unsubstituted alkoxy, substituted alkoxy, unsubstituted aroxy, substituted aroxy, unsubstituted alkylthio, substituted alkylthio, unsubstituted arylthio, substituted arylthio, unsubstituted carbonyl, substituted carbonyl, unsubstituted carboxyl, substituted carboxyl, unsubstituted amino, substituted amino, unsubstituted amido, substituted amido, unsubstituted sulfonyl, substituted sulfonyl, unsubstituted sulfamoyl, substituted sulfamoyl, unsubstituted phosphonyl, substituted phosphonyl, unsubstituted polyaryl, substituted polyaryl, $C_3$-$C_{20}$ cyclic, substituted $C_3$-$C_{20}$ cyclic, unsubstituted $C_3$-$C_{20}$ cyclic heterocyclic, substituted $C_3$-$C_{20}$ cyclic heterocyclic, amino acid, poly(ethylene glycol), poly(lactic-co-glycolic acid), peptide, or polypeptide group.

In some embodiments of Formula VI, $R_{22}$, $R_{23}$, and $R_{24}$ are independently hydrogen, unsubstituted alkyl, substituted alkyl, unsubstituted alkenyl, substituted alkenyl, unsubstituted alkynyl, substituted alkynyl, unsubstituted aryl, substituted aryl, unsubstituted heteroaryl, substituted heteroaryl, unsubstituted alkoxy, substituted alkoxy, unsubstituted aroxy, substituted aroxy, unsubstituted alkylthio, substituted alkylthio, unsubstituted arylthio, substituted arylthio, unsubstituted carbonyl, substituted carbonyl unsubstituted carboxyl, substituted carboxyl, unsubstituted amido, substituted amido, unsubstituted sulfonyl, substituted sulfonyl, unsubstituted sulfamoyl, substituted sulfamoyl, unsubstituted phosphonyl, substituted phosphonyl, unsubstituted polyaryl, substituted polyaryl, unsubstituted $C_3$-$C_{20}$ cyclic, substituted $C_3$-$C_{20}$ cyclic, unsubstituted $C_3$-$C_{20}$ heterocyclic, substituted $C_3$-$C_{20}$ heterocyclic, amino acid, poly(lactic-co-glycolic acid), peptide, or polypeptide group.

In some embodiments of Formula VI, $R_{21}$ is a substituted carbonyl, $R_{22}$, $R_{23}$, and $R_{24}$ are hydrogen, and p is an integer between 1 and 20, inclusive.

In some embodiments of Formula VI, $R_{21}$ is a substituted carbonyl, $R_{22}$ and $R_{23}$ are hydrogen, $R_{24}$ is methyl, and p is an integer between 1 and 1000, inclusive, preferably between 1 and 20, inclusive.

C. Weight Average Molecular Weight

The weight average molecular weight of the polymers can vary. In some embodiments, the weight average molecular weight of the polymer, as determined by size exclusion chromatography (SEC), can be between about 500 Daltons and about 50,000 Daltons, preferably between about 2,000 Daltons and about 30,000 Daltons, most preferably between about 5,000 Daltons and about 20,000 Daltons. The weight average molecular weights of the polymers can also depend on their degree of polymerization. The term "degree of polymerization" is art recognized and refers to the number of monomeric units in a given polymer, such as a zwitterionic polymer described herein. In some embodiments, degree of polymerization is between about 2 and about 10,000, inclusive, between about 2 and about 5,000, inclusive, between about 5 and about 1,000, inclusive, between about 5 and about 500, inclusive, between about 10 and about 200, inclusive, or between about 20 and about 80, inclusive. In some embodiments, the weight average molecular weights of the polymers are selected such that toxicity to cells can be avoided.

D. Cross-Linkers

In some embodiments, cross-linkers are used to cross-link the polymers to form zwitterionic hydrogels. Any cross-linker can be used. In some embodiments, the cross-linker is water-soluble. In some embodiments, zwitterionic cross-linkers, neutral cross-linkers, or a combination thereof can be used to cross-link the polymers. The cross-linkers contain reactive moieties that can react with the reactive side chains of the polymers to form a covalent bond. Reactive moieties include, but are not limited to, hydroxyl, thiol, maleimide, aziridine, —$N_3$, —CN, acrylamide, vinyl sulfone, cyanate, thiocyanate, isocyanate, isothiocyanate, vinyl silane, silicon hydride, acetohydrazide, acyl azide, acyl halides, N-hydroxysuccinimide ester, sulfonyl chloride, glyoxal, carbodiimides, aryl halides, imido ester, and alkynes.

The cross-linking density can be adjusted to alter the rate of degradation, the strength, or both, of the zwitterionic hydrogel. The cross-link density can be adjusted by adjusting the proportion of the monomers containing reactive side chains in the polymers, adjusting the concentration of the cross-linker in the cross-linking reaction, changing the number of reactive arms in cross-linker, such as by using a two-arm linker instead of a four-armed linker, or combinations thereof. The cross-linking density can be determined for a cross-linked polymer using any means known in the art, such as the approach described in Wang, et al., Nat. Biotechnol. 2002, 20(6), 602-606.

1. Zwitterionic Cross-Linkers

Zwitterionic cross-linkers include cross-linkers that contain one or more cationic groups and one or more anionic groups. Zwitterionic cross-linkers can be used to cross-link the polymers to form zwitterionic hydrogels. In some embodiments the zwitterionic cross-linkers are two- or multi-armed. Exemplary zwitterionic cross-linkers include those described in U.S. Patent Application Publication No. 2015/0037598, the contents of which are incorporated herein by reference.

Two-Armed Zwitterionic Cross-Linkers

Two-armed zwitterionic cross-linkers are those that contain two reactive moieties that are used to cross-link the polymers. The two-armed zwitterionic cross-linkers can be homo-bifunctional (i.e., contain the same reactive moieties) or hetero-bifunctional (i.e., contain the different reactive moieties). In some embodiments, the reactive moieties are independently thiol and maleimide. An exemplary two-armed, homo-bifunctional zwitterionic cross-linker is shown below:

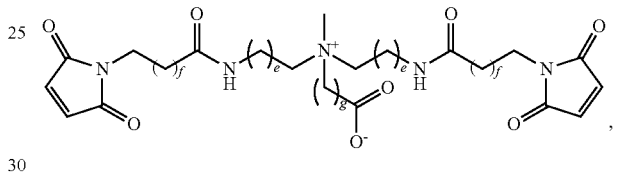

g and each e and f are independently an integer between 1 and 10, inclusive. Preferably, each f is independently an integer between 1 and 9, inclusive, each e is independently 1 or 2, and g is an integer between 1 and 3, inclusive.

Multi-Armed Zwitterionic Cross-Linkers

Multi-armed zwitterionic cross-linkers are those that contain three or more moieties that are used to cross-link the polymers. The multi-armed zwitterionic cross-linkers can be homo-polyfunctional (i.e., contain the same reactive moieties) or hetero-polyfunctional (i.e., contain the different reactive moieties). An exemplary multi-armed, homo-polyfunctional zwitterionic cross-linker is shown below:

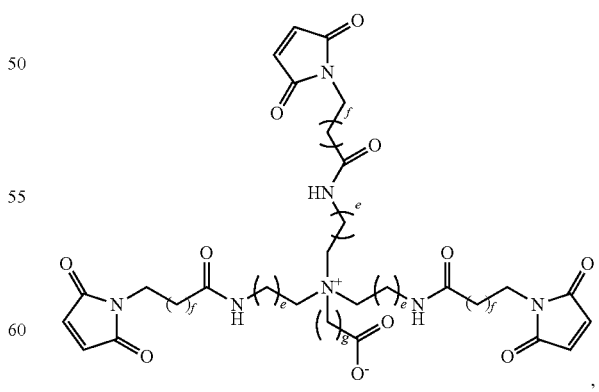

e, f, and g are as described above.

Exemplary four-armed zwitterionic cross-linkers are shown below:

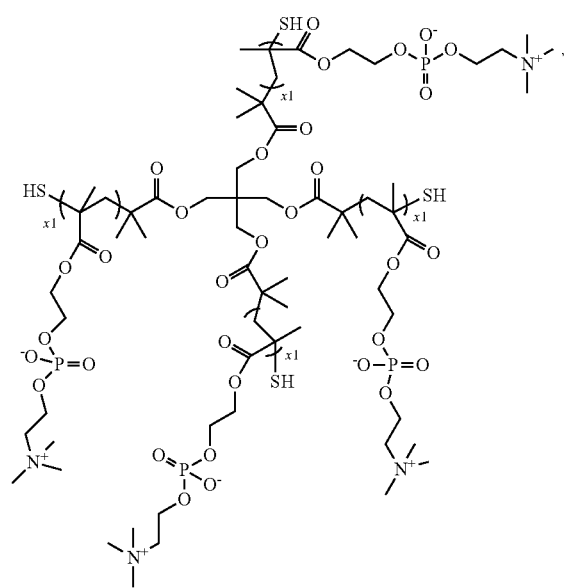
4 Arm MPC linker
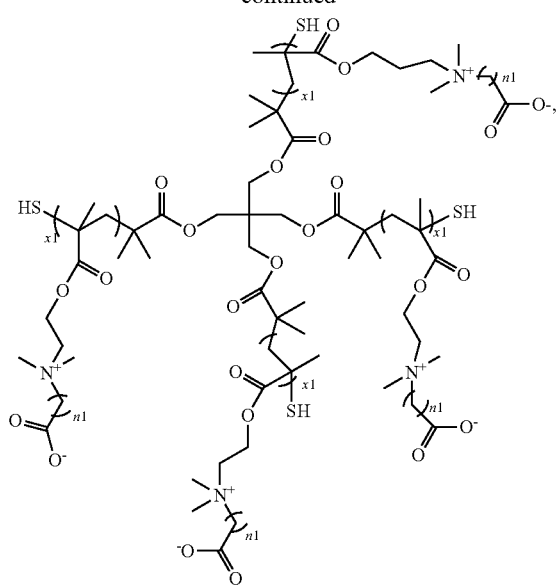
4 Arm CBMA linker
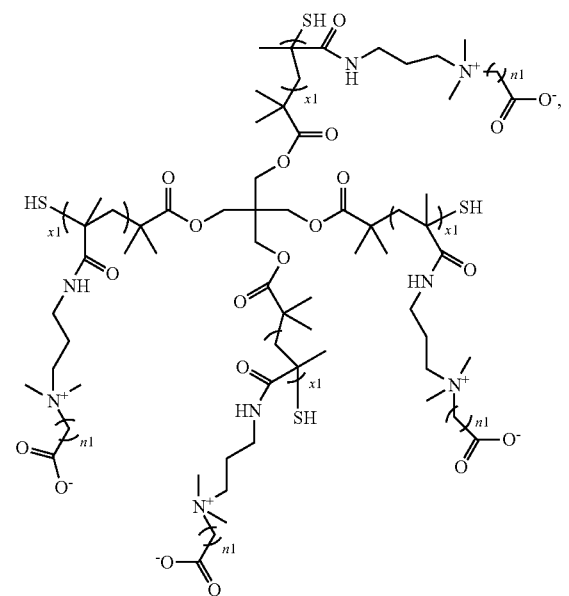
4 Arm CBMAA linker
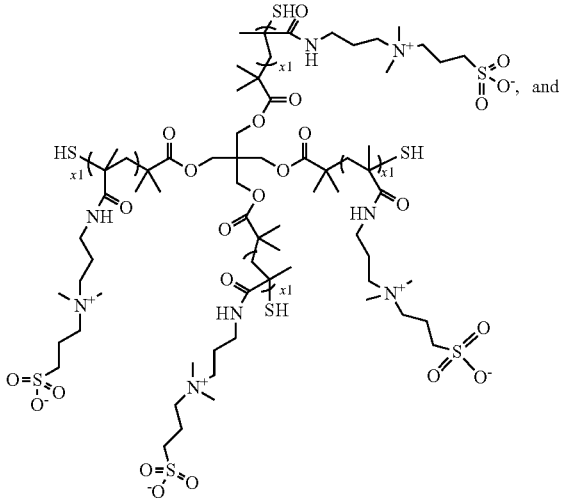
4 Arm SBMAA linker -continued

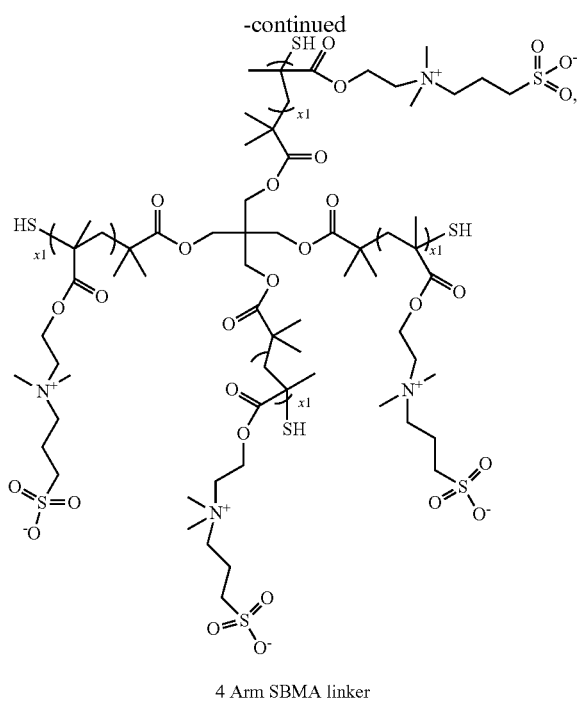

4 Arm SBMA linker wherein each n1 is independently an integer between 1 and 3, inclusive; each x1 is independently an integer between 1 and 1000, inclusive.

2. Neutral Cross-Linkers

Neutral cross-linkers include cross-linkers that do not contain a charged group covalently bound to another atom within the cross-linker. Neutral cross-linkers can be used to cross-link the polymers to form zwitterionic hydrogels. In some embodiments the neutral cross-linkers are two- or multi-armed.

Two-Armed Neutral Cross-Linkers

The two-armed neutral cross-linkers can be homo-bifunctional or hetero-bifunctional. An exemplary homo-bifunctional, neutral cross-linker is shown below:

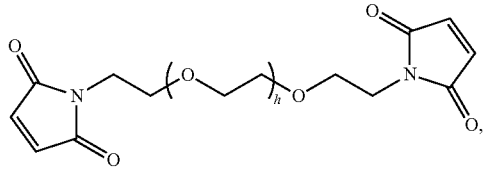

h is an integer between 1 and 1,000, inclusive, between 10 and 600, inclusive, or between 100 and 500. Preferably, h is about 450.

Additional examples of two-armed, neutral cross-linkers include, but are not limited to, aldehydes such as ethanedial, pyruvaldehyde, 2-formyl-malonaldehyde, glutaraldehyde, adipaldehyde, heptanedial, octanedial; di-glycidyl ether, diols such as 1,2-ethanediol, 1,3-propanediol, 1,4-butanediol, 2,3-butanediol, 1,5-pentanediol, benzene-1,4-diol, 1,6-hexanediol, tetra(ethylene glycol) diol), PEG, di-thiols such as 1,2-ethanedithiol, 1,3-propanedithiol, 1,4-butanedithiol, 2,3-butanedithiol, 1,5-pentanedithiol, benzene-1,4-dithiol, 1,6-hexanedithiol, tetra(ethylene glycol) dithiol), di-amine such as ethylene diamine, propane-1,2-diamine, propane-1,3-diamine, N-methylethylenediamine, N,N'-dimethylethylenediamine, pentane-1,5-diamine, hexane-1,6-diamine, spermine and spermidine, divinyladipate, divinylsebacate, diamine-terminated PEG, double-ester PEG-N-hydroxysuccinimide, and di-isocyanate-terminated PEG, epichlorohydrin, S-acetylthioglycolic acid N-hydroxysuccinimide ester, bromoacetic acid N-hydroxysuccinimide ester, N-(3-dimethylaminopropyl)-N'-ethylcarbodiimide, iodoacetic acid N-hydroxysuccinimide ester, 4-(N-maleimido)benzophenone 3-(2-pyridyldithio)propionic acid N-hydroxysuccinimide ester 3-maleimidobenzoic acid N-hydroxysuccinimide ester, N,N'-cystamine-bis-acrylamide, N,N'-methylene-bis-acrylamide and N,N'-ethylene-bis-acrylamide.

Multi-Armed Neutral Cross-Linkers

The multi-armed neutral cross-linkers can be homo-polyfunctional or hetero-polyfunctional. An exemplary homo-polyfunctional, multi-armed neutral cross-linker is shown below:

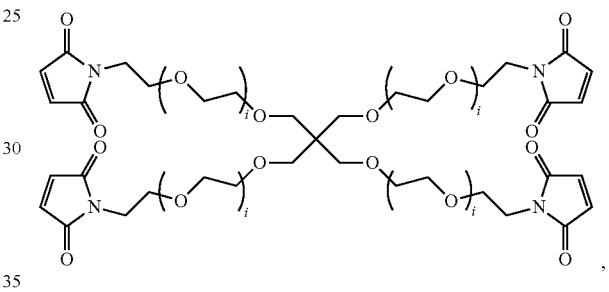

each i is independently an integer between 1 and 1,000, inclusive.

In some embodiments, the cross-linkers have the structures shown below in Formula III:

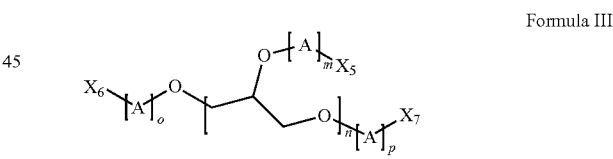

Formula III or Formula IV:

Formula IV wherein A is —$(CH_2)_2O$— or hydrogen, wherein m, n, o and p are independently integers from 1-50, and wherein, as valence permits, $X_5$, $X_6$, $X_7$, and $X_8$, when present, are independently

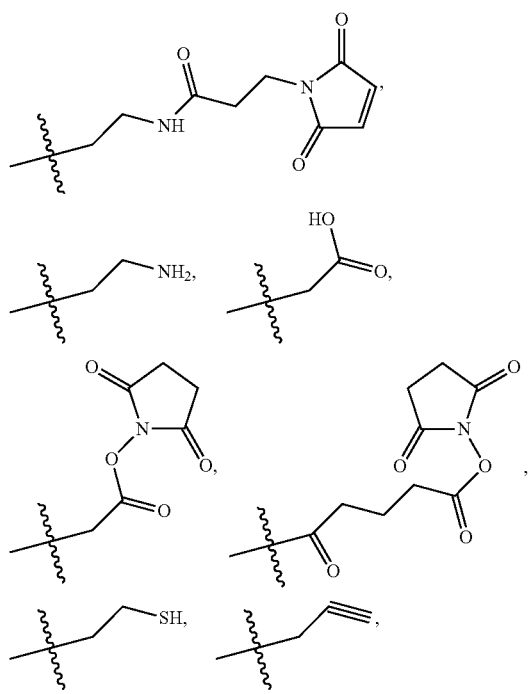

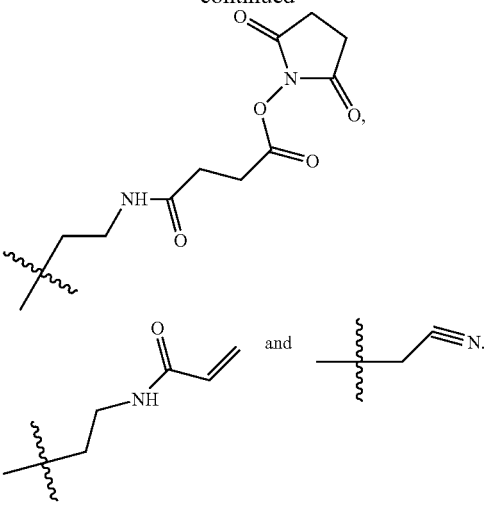

In some embodiments, $X_5$, $X_6$, $X_7$, and $X_8$, when present, are the same, giving rise to homo-polyfunctional cross-linkers. Additional examples of homo-polyfunctional cross-linkers include, but are not limited to, glycerol, monosaccharides, disaccharides, polysaccharides, hyperbranched polyglycerol, trimethylol propane, trimethylol propane triacrylate, triethanolamine, and glycerol trisglutaroyl chloride.

In some embodiments, $X_5$, $X_6$, $X_7$, and $X_8$, when present, are different, giving rise to hetero-polyfunctional cross-linkers. Additional examples of hetero-polyfunctional cross-linkers include, but are not limited to, 2-aminomalonaldehyde, genipin, 2,3-dithiopropanol, 2,3-bis(thiomethyl) butan-1,4-diol, 2,3-dihydroxybutane-1,4-dithiol, and methyl 3,4,5-trihydroxybenzoate, tris(hydroxymethyl)aminomethane.

3. Weight Average Molecular Weight

The weight average molecular weights of the cross-linkers can be varied to alter the porosity of the zwitterionic hydrogel. The weight average molecular weights can be between about 500 Daltons and about 50,000 Daltons, inclusive, between about 1000 Daltons and about 45,000 Daltons, inclusive, between about 1,500 Daltons and about 10,000 Daltons, inclusive. In some embodiments, the weight average molecular weight of the cross-linker can be 2,000 Daltons, 5,000 Daltons, 10,000 Daltons, 20,000 Daltons, or 40,000 Daltons.

III. Cells to be Encapsulated

Any biological cell can be included in the disclosed products.

The cell type chosen for inclusion depends on the desired therapeutic effect. For example, the cells can be endocrine cells, stem cells, and/or genetically engineered cells with sense and response functions. The cells may be from the patient (autologous cells), from another donor of the same species (allogeneic cells), or from another species (xenogeneic). Xenogeneic cells are easily accessible, but the potential for rejection and the danger of possible transmission of viruses to the patient restricts their clinical application. Any of these types of cells can be from natural sources, stem cells, derived cells, or genetically engineered cell.

In some embodiments, the cells secrete a therapeutically effective substance, such as a protein or nucleic acid. In some embodiments, the cells produce a metabolic product.

In some embodiments, the cells metabolize toxic substances. In some embodiments, the cells form structural tissues, such as skin, bone, cartilage, blood vessels, or muscle. In some embodiments, the cells are natural, such as islet cells that naturally secrete insulin, or hepatocytes that naturally detoxify. In some embodiments, the cells are genetically engineered to express a heterologous protein or nucleic acid and/or overexpress an endogenous protein or nucleic acid.

Types of cells for inclusion in the disclosed products include cells from natural sources, such as cells from xenotissue, cells from a cadaver, and primary cells; stem cells, such as embryonic stem cells, mesenchymal stem cells, and induced pluripotent stem cells; derived cells, such as cells derived from stem cells, cells from a cell line, reprogrammed cells, reprogrammed stem cells, and cells derived from reprogrammed stem cells; and genetically engineered cells, such as cells genetically engineered to express a protein or nucleic acid, cells genetically engineered to produce a metabolic product, and cells genetically engineered to metabolize toxic substances.

Types of cells for inclusion in the disclosed products include liver cells (e.g., hepatoblasts liver stellate cells, biliary cells, or hepatocytes), insulin producing cells (e.g., pancreatic islet cells, isolated pancreatic beta cells, or insulinoma cells), kidney cells, epidermal cells, epithelial cells, neural cells, including neurons and glial cells (e.g., astrocytes), ganglion cells, retinal epithelial cells, adrenal medulla cells, lung cells, cardiac muscle cells, osteoblast cells, osteoclast cells, bone marrow cells, spleen cells, thymus cells, glandular cells, blood cells (e.g., T cells, B cells, macrophage lineage cells, lymphocytes, or monocytes), endocrine hormone-producing cells (e.g., parathyroid, thyroid, or adrenal cells), cells of intestinal origin and other cells acting primarily to synthesize and secret or to metabolize materials, endothelial cells (e.g., capillary endothelial cells), fibroblasts (e.g., dermal fibroblasts), myogenic cells, keratinocytes, smooth muscle cells, progenitor cells (e.g., bone marrow progenitor cells, adipose progenitor cells, hepatic precursor cells, endothelia progenitor cells, peripheral blood progenitor cells, or progenitor cells from muscle, skin), and marrow stromal cells.

A preferred cell type is a pancreatic islet cell or other insulin-producing cell. Methods of isolating pancreatic islet cells are known in the art. Field et al., *Transplantation* 61:1554 (1996); Linetsky et al., *Diabetes* 46:1120 (1997). Fresh pancreatic tissue can be divided by mincing, teasing, commination and/or collagenase digestion. The islets can then be isolated from contaminating cells and materials by washing, filtering, centrifuging or picking procedures. Methods and apparatus for isolating and purifying islet cells are described in U.S. Pat. No. 5,447,863 to Langley, U.S. Pat. No. 5,322,790 to Scharp et al., U.S. Pat. No. 5,273,904 to Langley, and U.S. Pat. No. 4,868,121 to Scharp et al. The isolated pancreatic cells may optionally be cultured prior to inclusion in the product using any suitable method of culturing islet cells as is known in the art. See e.g., U.S. Pat. No. 5,821,121 to Brothers. Isolated cells may be cultured in a medium under conditions that helps to eliminate antigenic components. Insulin-producing cells can also be derived from stem cells and cell lines and can be cells genetically engineered to produce insulin.

Hormone-producing cells can produce one or more hormones, such as insulin, parathyroid hormone, anti-diuretic hormone, oxytocin, growth hormone, prolactin, thyroid stimulating hormone, adrenocorticotropic hormone, follicle-stimulating hormone, lutenizing hormone, thyroxine, calcitonin, aldosterone, cortisol, epinephrine, glucagon, estrogen, progesterone, and testosterone. Genetically engineered cells are also suitable for inclusion in the disclosed products. In some embodiments, the cells are engineered to produce one or more hormones, such as insulin, parathyroid hormone, anti-diuretic hormone, oxytocin, growth hormone, prolactin, thyroid stimulating hormone, adrenocorticotropic hormone, follicle-stimulating hormone, lutenizing hormone, thyroxine, calcitonin, aldosterone, cortisol, epinephrine, glucagon, estrogen, progesterone, and testosterone. In some embodiments, the cells are engineered to secrete blood clotting factors (e.g., in a subject with hemophilia) or to secrete growth hormones. In some embodiments, the cells are contained in natural or bioengineered tissue. For example, the cells for inclusion in the disclosed products are in some embodiments a bioartificial renal glomerulus. In some embodiments, the cells are suitable for transplantation into the central nervous system in cases of a neurodegenerative disease.

Cells can be obtained directly from a donor, from cell culture of cells from a donor, or from established cell culture lines. In the preferred embodiments, cells are obtained directly from a donor, washed and implanted directly in combination with the polymeric material. The cells are cultured using techniques known to those skilled in the art of tissue culture.

Cell viability can be assessed using standard techniques, such as histology and fluorescent microscopy. The function of the implanted cells can be determined using a combination of these techniques and functional assays. For example, in the case of hepatocytes, in vivo liver function studies can be performed by placing a cannula into the recipient's common bile duct. Bile can then be collected in increments. Bile pigments can be analyzed by high pressure liquid chromatography looking for underivatized tetrapyrroles or by thin layer chromatography after being converted to azodipyrroles by reaction with diazotized azodipyrroles ethylanthranilate either with or without treatment with P-glucuronidase. Diconjugated and monoconjugated bilirubin can also be determined by thin layer chromatography after alkalinemethanolysis of conjugated bile pigments. In general, as the number of functioning transplanted hepatocytes increases, the levels of conjugated bilirubin will increase. Simple liver function tests can also be done on blood samples, such as albumin production. Analogous organ function studies can be conducted using techniques known to those skilled in the art, as required to determine the extent of cell function after implantation. For example, pancreatic islet cells and other insulin-producing cells can be implanted to achieve glucose regulation by appropriate secretion of insulin. Other endocrine tissues and cells can also be implanted.

IV. Media and Pharmaceutically Acceptable Excipients

The cells to be encapsulated can be formulated in any cell culture, media, or pharmaceutically acceptable excipients suitable for implantation into a human, such as saline and phosphate buffered saline ("PBS").

Pharmaceutically acceptable excipients can be included in the formulations. Pharmaceutically acceptable excipients that can be used in the formulations include, but are not limited to, inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents can be present in the composition, according to the judgment of the formulator.

V. Methods of Making the Polymeric Materials

A. Zwitterionic Hydrogels Encapsulating Cells

1. Materials

The zwitterionic hydrogels are generated by cross-linking the zwitterionic polymers described above, using the cross-linkers described above. About 20 w/v % of polymer in PBS can be mixed with appropriate amount of cross linkers dissolved in PBS to form hydrogels. Upon mixing, hydrogels can be formed in about 10-60 seconds at room temperature.

2. Properties

Size

Figures 2A, 2B, 2C:
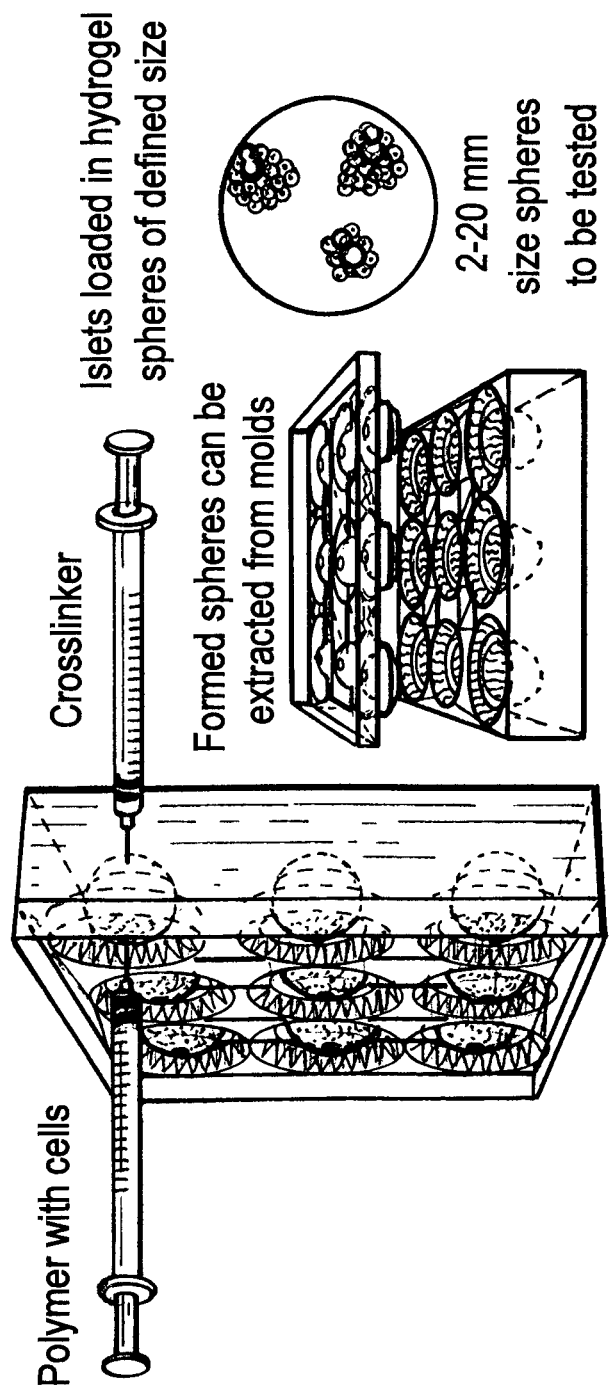
FIG. 2A-2C are prospective views of a closed mold for injection of polymer (FIG. 2A), the mold opened to remove spheres (FIG. 2B), and a spherical zwitterionic hydrogel produced in the mold (FIG. 2C).

The zwitterionic hydrogels can have any size and shape using appropriate molds such as those shown in FIGS. 2A and 2B into which the polymer is injected, where it hardens to the desired shape and size. The molds can be formed using materials that are chemically inert and/or have low surface free energies, i.e., the materials easily release substances. These materials include, but are not limited to, polysiloxanes, polytrifluoroethylene, polytetrafluoroethylene, polyurethanes, polysiloxanes, and polyimides. Preferably, the molds are made from polysiloxanes, such as polydimethylsiloxane. In some embodiments, the zwitterionic hydrogels are spheres (FIG. 2C), i.e., spherical. In some embodiments, the spherical zwitterionic hydrogels have a diameter between about 150 µm and about 30 mm, inclusive, between about 500 µm and about 30 mm, inclusive, or between about 2 mm and about 20 mm. The diameter of the spherical zwitterionic hydrogels can be about 500 µm, or 5 mm.

Porosity

In some embodiments, the mean pore size of zwitterionic hydrogels, determined using Cryo-Scanning electron microscopy can be between about 10 nm and about 20 µm, inclusive, between about 25 nm and about 15 µm, inclusive, between about 50 nm and about 15 µm, inclusive, between about 75 nm and about 10 µm, inclusive, or between about 100 nm and about 5 µm, inclusive.

Foreign Body Response

In general, the zwitterionic hydrogels possess a beneficial effect, such as inducing a lower foreign body response. The foreign body response for the zwitterionic hydrogels can be measured by determining the activities of responding macrophages and neutrophils, using an in vivo PROSENSE680™ (VisEn Medical, Woburn, Mass., excitation wavelength 680±10 nm, emission 700±10 nm) based imaging technique, and compared to the foreign body response to PEG control gels. The procedure for carrying out the in vivo PROSENSE™ imaging is described in Vegas, et al., Nat. Biotechnol. 2016, 34, 345. In some embodiments, the foreign body response to the zwitterionic hydrogel is less than 95%, 90%, 85%, 80%, 75%, 70%, 65%, 60%, 55%, 50%, 45%, 40%, 35%, 30%, 35%, or 20% of the foreign body response to a control hydrogel.

The zwitterionic hydrogels can be purified after cross-linking to remove any unreacted or partially reacted contaminants present with the zwitterionic hydrogels. The purified zwitterionic hydrogels can induce a lower foreign body response than a similar zwitterionic hydrogel that has not been purified.

Biodegradability

The zwitterionic hydrogels can be biocompatible, biodegrable, non-biodegradable, or a combination thereof. When the zwitterionic hydrogels are biodegradable (i.e., biodegrable or biocompatible and biodegradable), the choice of polymer backbone, weight average molecular weight of the polymer, the weight average molecular weight of the cross-linker, the type of cross-linker, cross-linking density, or combinations thereof, can influence the rate of degradation under physiological conditions.

B. Device Coatings

1. Materials

In some embodiments, the zwitterionic polymers are coated to the surfaces of other biomaterials and devices, collectively called substrates. The zwitterionic polymer coatings can reduce the foreign body responses and fibrosis to the biomaterials and devices after implantation. The zwitterionic polymers can be coated onto any substrates of any shape and size. When used as coatings, the zwitterionic polymers can be reacted with reactive groups on the surfaces of the substrates to form covalent bonds, physically adsorbed onto the surface of the substrates, cross-linked with any of the cross-linkers described above, or combinations thereof.

Substrates can be prepared from a variety of materials. In some embodiments, the material is biocompatible, biodegradable, non-biodegradable, or a combination thereof. Exemplary materials include metallic materials, metal oxides, polymeric materials, including degradable and non-degradable polymeric materials, ceramics, porcelains, glass, allogeneic, xenogeneic bone or bone matrix; genetically engineered bone; and combinations thereof.

Many pharmaceutically acceptable polymers can be used to form the biomaterials onto which the polymeric zwitterions are coated. Exemplary polymers include, but are not limited to, polysaccharides such as alginate, chitosan, hyaluronan, and chondroitin sulfate, polystyrene, polyphosphazenes, poly(acrylic acids), poly(methacrylic acids), poly(alkylene oxides), poly(vinyl acetate), polyvinylpyrrolidone (PVP), poly(vinyl amines), poly(vinyl pyridine), poly(vinyl imidazole), poly(anhydrides), poly(hydroxy acids), polyesters, poly(ortho esters), poly(propylene fumarates), polyamides, polyamino acids, polyethers, polyacetals, polyhydroxyalkanoates, polyketals, polyesteramides, poly(dioxanones), polycarbonates, polyorthocarbonates, polycyanoacrylates, polyalkylene oxalates, polyalkylene succinates, poly(malic acid), poly(methyl vinyl ether), poly(ethylene imine), poly(maleic anhydride), copolymers and blends thereof.

The zwitterionic polymers can be covalently or non-covalently associated with the surface of the substrates. In some embodiments, the zwitterionic polymers are non-covalently associated with the surface. The zwitterionic polymers can be applied by any of a variety of techniques in the art including, but not limited to, spraying, wetting, immersing, dipping, such as dip coating, painting, or otherwise applying a hydrophobic, polycationic polymer to a surface of the implant.

In some embodiments, the zwitterionic polymers can be coated directly onto the surfaces of the biomaterials or devices.

In other embodiments, the surfaces of the biomaterials or devices can be treated with a material, such as a polymer, followed by applying the zwitterionic polymers onto the treated surface. As a non-limiting example, the surface of the substrate can be modified first with mussel-inspired polydopamine (PDA) films by oxidative self-polymerization of dopamine, and followed by conjugation of the zwitterionic polymers to the PDA film via any reactive group in the reactive side chains of the zwitterionic polymer, such as thiol or amine. Simple immersion of virtually any substrate in an alkaline aqueous solution of dopamine results in spontaneous deposition of a thin PDA film, with subsequent reactivity of this film toward amines and thiols to form ad-layers (Lee, et al., Science 2007, 318, 426; Lee, et al., Adv. Mater. 2009, 21, 431; and Ham, et al., Angew. Chem. Int. Ed. 2011, 50, 732). Using this method, thiol-containing zwitterionic polymers were attached to the surface of biomaterials to reduce the foreign body responses and fibrosis to these biomaterials. Alginate and polystyrene (PS) microparticles were chosen as non-limiting examples of biomaterials, to test the efficacy of the coating method and to study the in vivo performance of these coatings.

Alginate and/or PS microparticles with diameters of about 0.5 mm in Tris HCl buffer (10 mM, pH 8.5) were simply shaken on a benchtop orbital shaker. A stock solution of dopamine hydrochloride in the same Tris buffer was added to the microspheres with a final concentration of 3 mg/mL. The resultant mixtures were shaken at room temperature for 18 hours, and then washed multiple times with Tris buffer until to get a clear supernatant solution. Dopamine coated spheres were then taken into Tris buffer solution (pH 8, 10 mM). To this solution, a stock solution of poly(methacryloyloxyethyl phosphorylcholine) (poly(MPC)) in the same buffer was added to give a final 4 w/v % of poly(MPC) concentration. The final reaction mixture was then purged with nitrogen for 10 minutes to deoxygenate the reaction solution. The resultant mixtures were shaken at RT for 18-20 hours in dark, and rinsed multiple times with Tris buffer and stored in 0.9% saline solution at 4° C. until further use.

Other devices that can be coated using the polymers described herein include any types of medical devices used, at least in part, for implantation in the body, or in long term contact with biomaterial, of a patient or subject in need thereof.

Examples include, but are not limited to, implants including implantable medical products, implantable devices, catheters and other tubes (including urological and biliary tubes, endotracheal tubes, wound drain tubes, needle injection catheters, peripherally insertable central venous catheters, dialysis catheters, long term tunneled central venous catheters peripheral venous catheters, short term central venous catheters, arterial catheters, pulmonary catheters, Swan-Ganz catheters, urinary catheters, peritoneal catheters), vascular catheter ports, blood clot filters, urinary devices (including long term urinary devices, tissue bonding urinary devices, artificial urinary sphincters, urinary dilators), shunts (including ventricular or arterio-venous shunts, stent transplants, biliary stents, intestinal stents, bronchial stents, esophageal stents, ureteral stents, and hydrocephalus shunts), cannulas, (including intravenous cannulas and nasal cannulas), balloons, pacemakers, implantable defibrillators, orthopedic products (including pins, plates, screws, and implants), transplants (including organs, vascular transplants, vessels, aortas, heart valves, and organ replacement parts), prostheses (including breast implants, penile prostheses, vascular grafting prostheses, heart valves, artificial joints, artificial larynxes, otological implants, artificial hearts, artificial blood vessels, and artificial kidneys), aneurysm-filling coils and other coil devices, transmyocardial revascularization devices, percutaneous myocardial revascularization devices, tubes, fibers, hollow fibers, membranes, blood containers, titer plates, adsorber media, dialyzers, connecting pieces, sensors, valves, endoscopes, filters, pump chambers, scalpels, needles, scissors (and other devices used in invasive surgical, therapeutic, or diagnostic procedures), and other medical products and devices intended to have anti-fibrotic properties. The expression "medical products" is broad and refers in particular to products that come in contact with blood briefly (e.g., endoscopes) or permanently (e.g., stents).

Useful medical products are balloon catheters and endovascular prostheses, in particular stents. Stents of a conventional design have a filigree support structure composed of metallic struts. The support structure is initially provided in an unexpanded state for insertion into the body, and is then widened into an expanded state at the application site. The stent can be coated before or after it is crimped onto a balloon. A wide variety of medical endoprostheses or medical products or implants for highly diverse applications and are known.

They are used, for example, to support vessels, hollow organs, and ductal systems (endovascular implants), to attach and temporarily affix tissue implants and tissue transplants, and for orthopedic purposes such as pins, plates, or screws.

Substrates can be in the form of, or form part of, films, particles (nanoparticles, microparticles, or millimeter diameter beads), fibers (wound dressings, bandages, gauze, tape, pads, sponges, including woven and non-woven sponges and those designed specifically for dental or ophthalmic surgeries), sensors, pacemaker leads, catheters, stents, contact lenses, bone implants (hip replacements, pins, rivets, plates, bone cement, etc.), or tissue regeneration or cell culture devices, or other medical devices used within or in contact with the body.

Particles that are substrates for coating with the polymers can be particles encapsulating cells. Such cell encapsulating particles to be coated with the polymer can be formed from any material known or useful for encapsulating cells and can have any known and useful structure and layering. 2. Properties a. Thickness and Density of the Coating In some embodiments, the thickness of the coating on the surface of the device, determined using Scanning Electron Microscopy can between about 10 nm and about 1 cm, inclusive, between about 50 nm and about 1 cm, inclusive, between about 500 nm and about 1 cm, inclusive, between about 1 µm and about 500 µm, inclusive, between about 50 nm and 500 nm, between about 100 nm and 500 nm, between about 1 mm and about 2 mm, inclusive, or between about 1 mm and about 5 mm, inclusive.

b. Porosity

In some embodiments, the mean pore size of the coating, determined using Scanning Electron Microscopy can be between about 1 nm and about 20 µm, inclusive, between about 5 nm and about 15 µm, inclusive, between about 5 nm and about 10 µm, inclusive, between about 10 nm and about 5 µm, inclusive, or between about 10 nm and about 1 µm, inclusive.

c. Foreign Body Response

In general, the coatings impart a beneficial effect to the device, such as inducing a lower foreign body response to the device. The foreign body response to the coatings can be measured by determining the activities of responding macrophages and neutrophils, using in vivo PROSENSE-680$^{Tm}$ (VisEn Medical, Woburn, Mass., excitation wavelength 680±10 nm, emission 700±10 nm) based imaging technique, and, compared to a similar device that does not include the coatings. In some embodiments, the foreign body response to the coated device is less than 95%, 90%, 85%, 80%, 75%, 70%, 65%, 60%, 55%, 50%, 45%, 40%, 35%, 30%, 35%, or 20% of the foreign body response to a similar device that does not include the coatings.

The coatings can be purified after they have been applied to the surface of the substrate to remove any unreacted or partially reacted contaminants present with the coatings. The purified coatings induce a lower foreign body response than a similar coating that has not been purified.

d. Biodegradability

The coatings can be biocompatible, biodegrable, non-biodegradable, or a combination thereof. When the coatings are biodegradable, the choice of polymer backbone, weight average molecular weight of the polymer, the weight average molecular weight of the cross-linker, the type of cross-linker, cross-linking density, or combinations thereof, can influence the rate of degradation under physiological conditions.

VI. Methods of Making

A. Zwitterionic Polymers

Methods for the synthesis of the polymers from a zwitterionic monomer, monomer with a reactive side chain, and a monomer with a hydrophobic side chain or a monomer with a neutral hydrophilic side chain, are also provided. Any suitable method known in the art can be used to generate the polymers from monomers. In some embodiments, the monomers contain the zwitterionic side chains, reactive side chains, hydrophobic side chains and neutral hydrophilic side chains prior to polymerization. In some embodiments, the polymer is formed first, followed by modifications of the polymer to introduce the zwitterionic side chains, reactive side chains, hydrophobic side chains and neutral hydrophilic side chains. Exemplary zwitterionic monomers and a monomer with a reactive side chain are shown in FIG. 1A-1G 1. In some embodiments, the polymers are prepared via reversible addition-fragmentation chain transfer as shown in Scheme 1 and scheme 2.

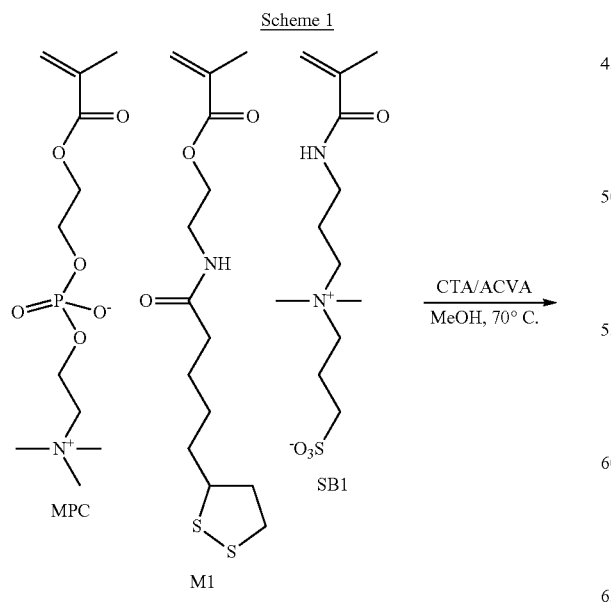

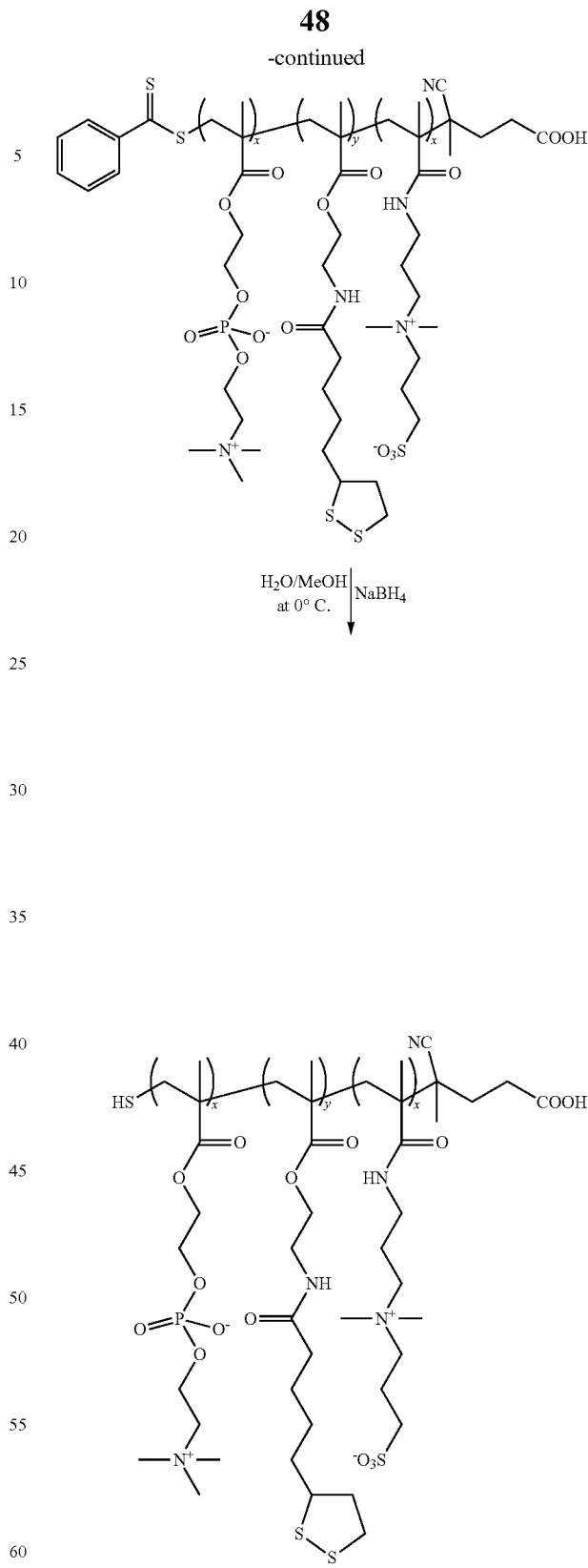

Zwitterionic selections + M1 →(RAFT)

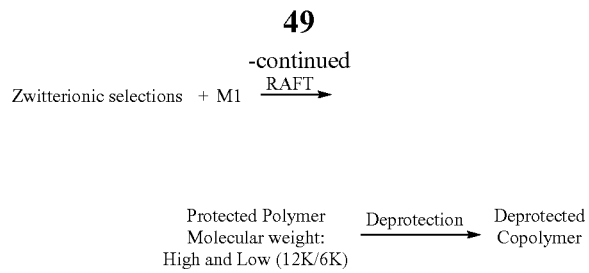

Scheme 1: Preparation of zwitterionic polymers containing two different zwitterionic monomers and a monomer with a reactive side chain. CTA-chain transfer agent; ACVA-4,4′-azobis(4-cyanovaleric acid); RAFT-Reversible addition-fragmentation chain transfer. M1-monomer with reactive side chain. Each x is independently an integer between 1 and 1,000, inclusive, preferably between 10 and 200, inclusive. y is an integer between 1 and 1,000, inclusive, preferably between 10 and 200, inclusive. In this scheme the monomer feed ratio of MPC/M1/SB1 was 70:10:20.

In some embodiments, such as in Scheme 2 below, z can be zero. Accordingly, in some forms, x and y are independently integers between 1 and 1000, inclusive, preferably x is between 10 and 200, inclusive, preferably y is between 2 and 20, inclusive; and z is between 0 and 1000, inclusive, preferably z is between 10 and 200, inclusive.

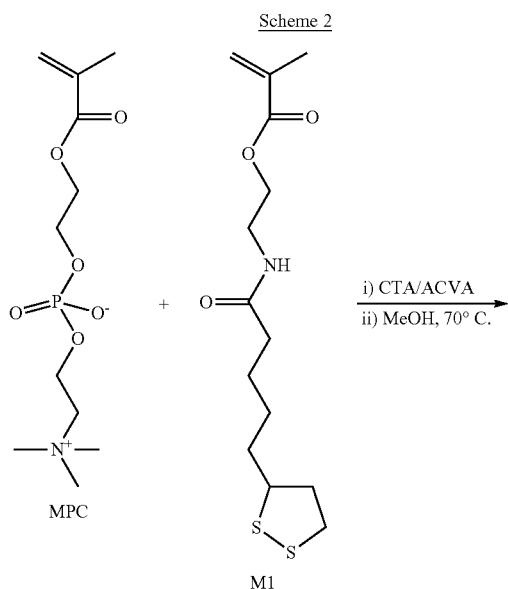

Scheme 2

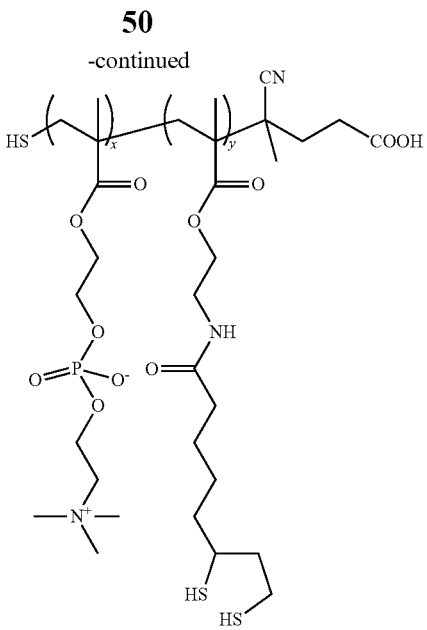

Scheme 2: Preparation of zwitterionic polymers containing one kind of zwitterionic monomers and a monomer with a reactive side chain. CTA-chain transfer agent; ACVA-4,4′-azobis(4-cyanovaleric acid); x and y are independently integers between 1 and 1,000, inclusive, preferably x is between 10 and 200, inclusive, and y is between 2 and 20, inclusive. In some embodiments, step (i) can be preformed in CTA/ACVA, methanol, and N,N-dimethyl acrylamide at 70° C.

The feed ratio of the monomer containing the reactive side chain to the zwitterionic monomer between about 1:1 and about 1:500, inclusive, between about 1:1 and about 1:100, inclusive, between about 1:1 and about 1:50, inclusive, between about 1:1 and about 1:30, inclusive, between about 1:1 and about 1:25, inclusive, or between about 1:1 and about 1:20, inclusive.

B. Zwitterionic Hydrogels

The zwitterionic hydrogels are prepared by cross-linking the polymers containing zwitterionic side chains, e.g., as described above, with any suitable cross-linker known in the art, such as the cross-linkers described above.

In some embodiments, the polymers are cross-linked using water-soluble cross-linkers without using organic solvents. The cross-linking reaction can be carried out at any temperature. In some embodiments, the cross-linking reaction can be carried out at room temperature in the presence of cells or other materials to be encapsulated. In some embodiments, the reactive side chain contains a thiol group, and the cross-linker contains a maleimide group. In this instance, cross-linking can occur via thiol-maleimide reactions at room temperature in a medium substantially free of organic solvents.

Performing the reactions in a medium substantially free of organic solvents, and using mild conditions are important improvements, because organic solvents, extreme, and the presence of toxic photoinitiators and reagents, can damage cells. Any condition conducive with biological cells can be used for zwitterionic hydrogel formation reaction. Exemplary mild conditions, under which the zwitterionic hydrogels can be formed in the presence of cells, include a temperature between about 3° C. and about 48° C., inclusive, a solution with salinity between about 0.01% and about 3%, or a combination thereof. The cross-linking reaction can be performed without the use of initiators, free radicals, or UV light.

An exemplary approach that can be used to generate zwitterionic hydrogels using the polymers and cross-linkers described above is shown in scheme 3.

Scheme 3

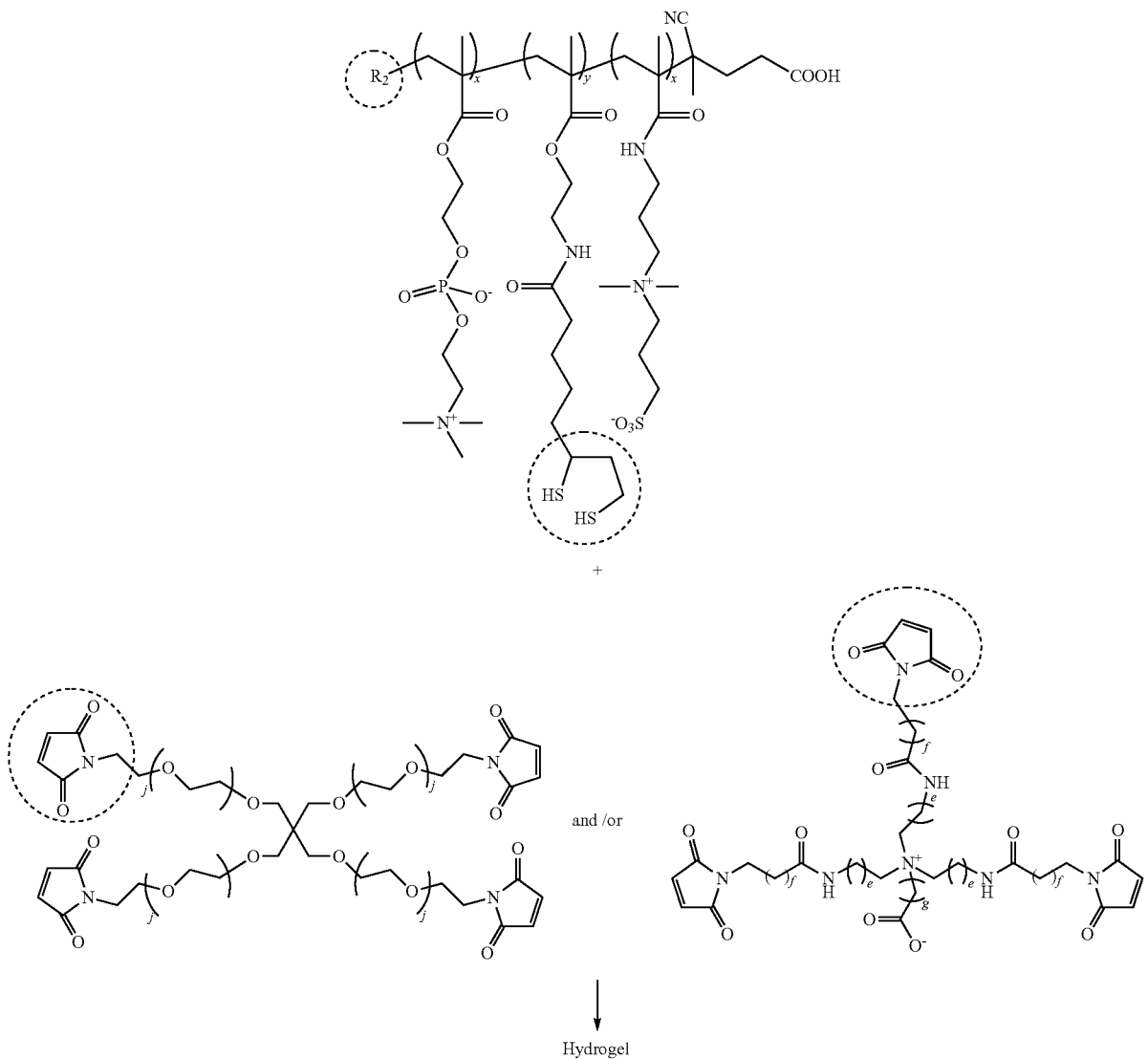

Scheme 3: An approach to preparing zwitterionic hydrogels. g is an integer between 1 and 20, inclusive. Each j is independently an integer between 1 and 1,000, inclusive. Each x is independently an integer between 1 and 1,000, inclusive, and y is an integer between 1 and 1,000, inclusive. Each e and f is independently an integer between 1 and 10, inclusive. preferably, each f is independently an integer between 1 and 9, inclusive, each e is independently 1 or 2, and g is an integer between 1 and 3, inclusive.

VII. Methods of Using

The products can be used in applications where improved biocompatibility and physical properties (such as being anti-fibrotic), as compared to other commercially available products or control products, are useful or preferred. These include, but are not limited to, tissue engineering, implanted sensors, drug delivery, gene transfection systems, medical nanotechnology and biotechnology, and implantable medical devices to reduce fibrosis and foreign body responses.

The products described herein can be used in the treatment or diagnosis of a broad spectrum of diseases, disorders, and conditions, i.e., to improve or diagnose diseases, disorders, and conditions in a human or animal subject. For example, products that include cells or tissues can be used in disorders characterized by a need for a product produced by the cell or tissue or of a reaction mediated by a product of the cell. For example, the cells can be an islet cells and the disorder is diabetes. In some embodiments, the product can include cells that metabolize or modify a substrate produced by the subject.

A. Methods of Encapsulation and Implantation

The site, or sites, where cells are to be implanted is determined based on individual need, as is the requisite number of cells. For cells replacing or supplementing organ or gland function (for example, hepatocytes or islet cells), the mixture can be injected into the mesentery, subcutaneous tissue, retroperitoneum, properitoneal space, and intramuscular space.

The amount and density of cells included in the products will vary depending on the choice of cell and site of implantation. In some embodiments, the single cells are present in the product at a concentration of $0.1\times10^6$ to $4\times10^6$ cells/ml, preferred $0.5\times10^6$ to $2\times10^6$ cells/ml. In other embodiments, the cells are present as cell aggregates. For example, islet cell aggregates (or whole islets) preferably contain between about 1500 and about 2000 cells, inclusive, for each aggregate with a diameter of about 150 μm, which is defined as one islet equivalent (IE). In some embodiments, islet cells are present at a concentration of between about 100 and about 10000 IE/ml, inclusive, preferably between about 200 and about 3,000 IE/ml, inclusive, more preferably between about 500 and about 1500 IE/ml, inclusive.

The cells to be encapsulated can be formulated in any cell culture, media, or pharmaceutically acceptable excipients suitable for implantation into human. The zwitterionic ionic hydrogels with or without cells can be formulated in any of the media optionally containing any of the pharmaceutically acceptable excipients described above for implantation.

Figure 3:
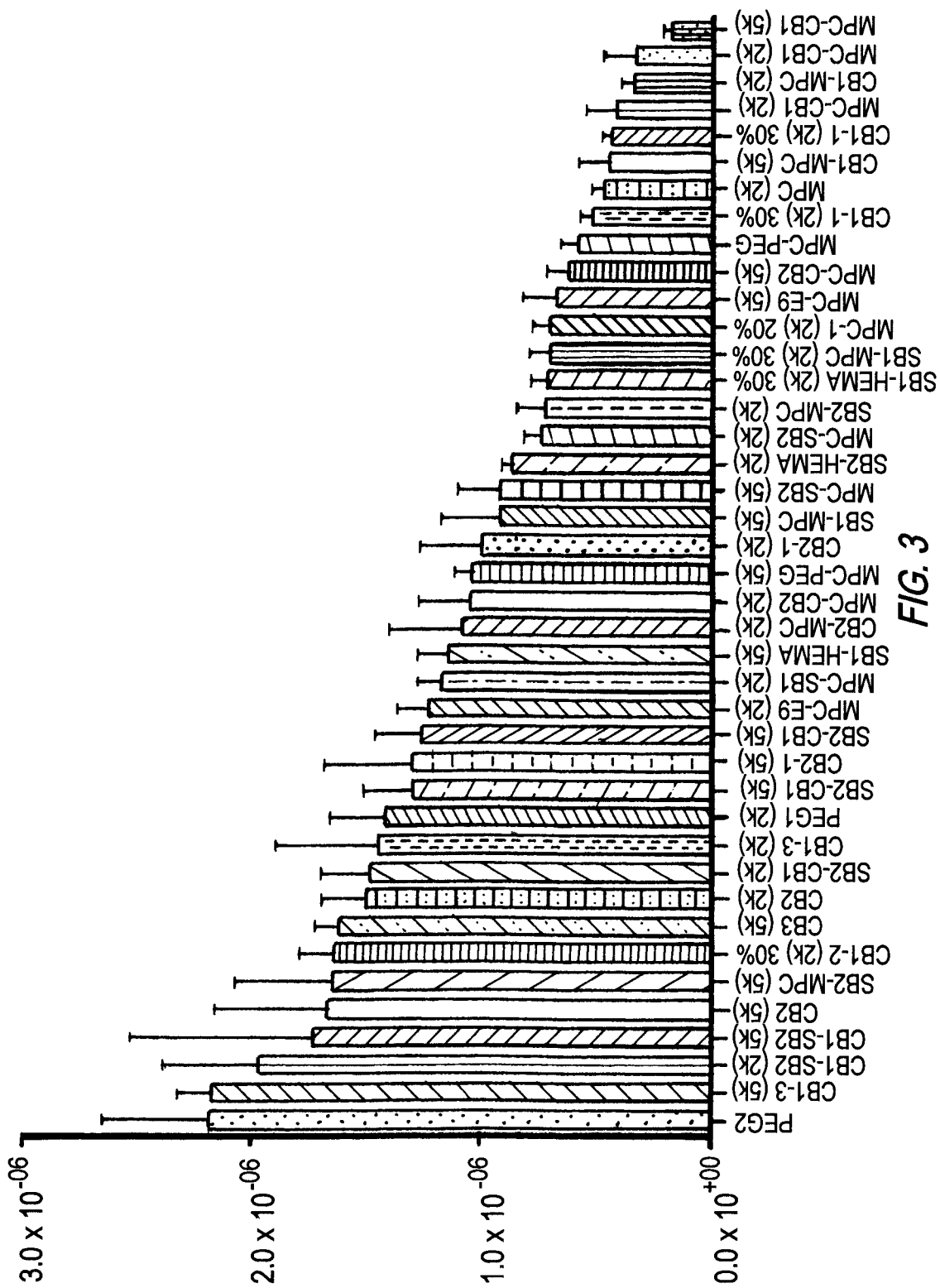
FIG. 3 is a bar graph of the in vivo screening of control and zwitterionic hydrogels using PROSENSE-680™. The hydrogels are shown on the horizontal axis and the foreign body response is shown on the vertical axis.

In some embodiments, the zwitterionic polymers are applied to a capsule that is formed from another biomaterial. In general, the coatings impart a beneficial effect to the device, such as improved biocompatibility, measured using an in vivo PROSENSE-680™ (VisEn Medical, Woburn, Mass., excitation wavelength 680±10 nm, emission 700±10 nm) based imaging technique, and compared to a similar device that does not include the coatings. For example, coating an alginate microcapsule with a zwitterionic polymer formed from 2-methacyloyloxyethyl-2'-trimethylammoniumethyl phosphate-(3-acryloylamino-propyl)-(2-carboxy-ethyl)-dimethyl-ammonium-polyethylene glycol (MPC-CBAA-PEG) improves the in vivo biocompatibility of the alginate capsule. See FIG. 3

B. Implantation of Coated Devices

The site where cells are to be implanted is determined based on individual need, as is the requisite number of cells. For cells replacing or supplementing organ or gland function (for example, hepatocytes or islet cells), the zwitterionic hydrogels or devices containing cells can be implanted into the mesentery, subcutaneous tissue, intraperitoneum, brain, retroperitoneum, properitoneal space, and intramuscular space.

EXAMPLES

Example 1: Combinatorial Synthesis and Screening of Library of Zwitterionic Hydrogels Using a combinatorial synthesis and screening strategy a broad library (more than 400 formulations) of zwitterionic acrylate hydrogels was generated, and the ability of each formulation to reduce foreign body response and fibrosis was tested.

Materials and Methods

Synthesis of Library of Zwitterionic Polymers

The zwitterionic monomers shown in FIGS. 1A-1G were synthesized in-house, and were used to generate a library of zwitterionic polymers using different combinations of these monomers, following the approach demonstrated in scheme 1 or scheme 2. Each zwitterionic polymer in the library was mixed with one or both of the cross-linkers shown in scheme 3 to cross-link the zwitterionic polymers to generate a library of zwitterionic hydrogels. See FIGS. 8A-8M. The cross-linking reaction was performed in saline solution.

In Vitro Screening Macrophage Adhesion Assay

Macrophage cells where seeded onto various zwitterionic gel formulations, and control alginate hydrogels. Fluorescence indicates the degree of adherence of macrophage cells, or an immune response.

In Vivo Screening to Determine Cytotoxicities of Zwitterionic Hydrogels

Figure 4:
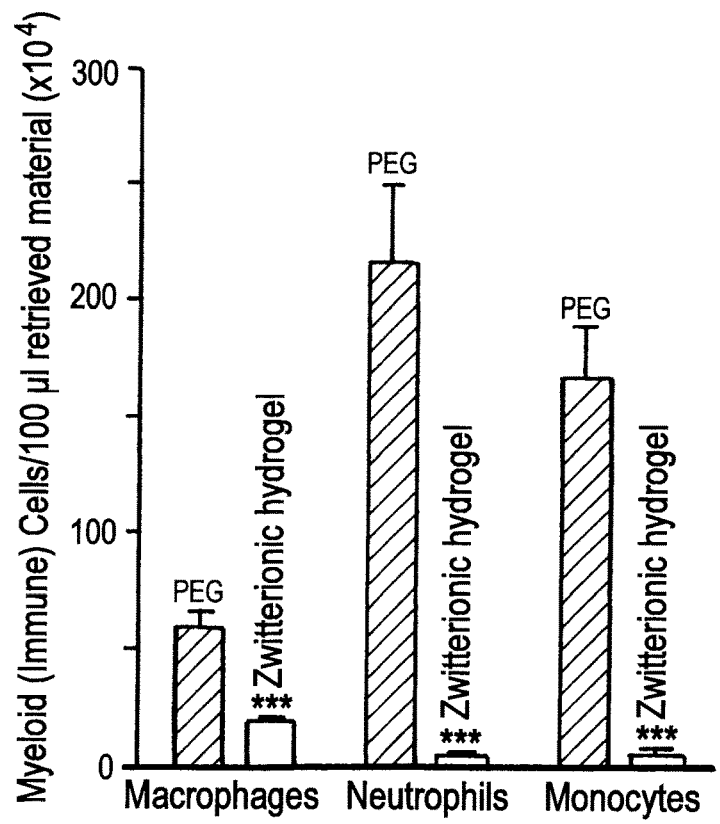
FIG. 4 is a bar graph of foreign body reactions to a zwitterionic hydrogel (MPC1) compared to a hydrogel formed with PEG, transplanted to the intraperitoneal space of B6 mice for 14 days. The hydrogels were molded as cylinders (4 mm×1 mm).

Mice were administered a zwitterionic gel implant and a control saline solution. Images were taken seven days after implantation. A difference in fluorescence between the gel and control sides indicated an immune response to the implant. Fluorescence intensity was quantified to compare gel immune responses. See FIG. 4 comparing macrophages, neutrophils, and monocytes.

Insulinoma cells were encapsulated in representative zwitterionic gels. Images were taken one day following encapsulation. Green fluorescence marks live cells. Displayed gel exhibited significant cell survival.

Figure 5:
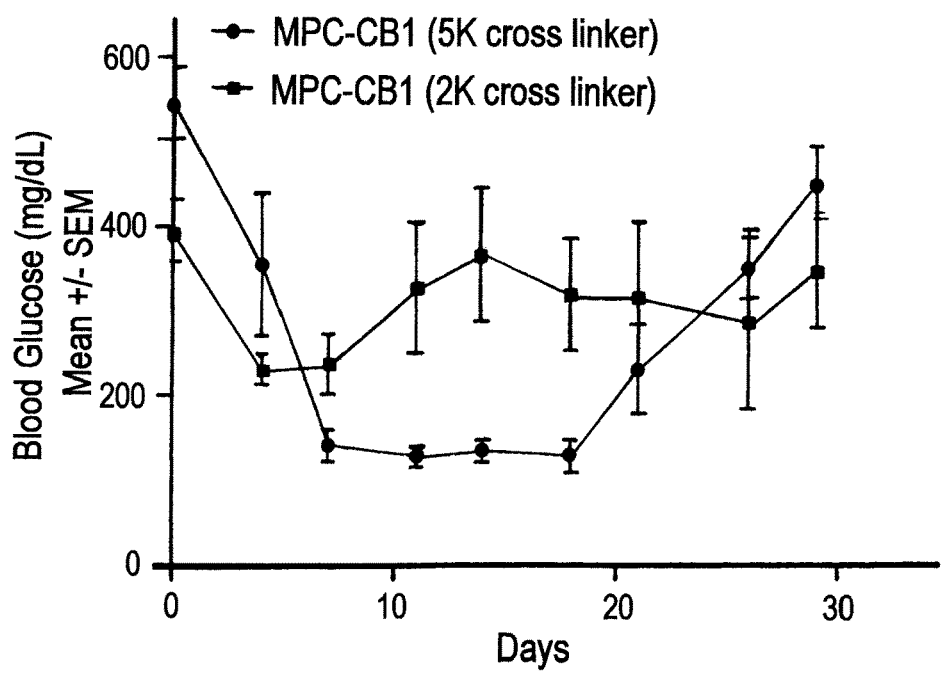
FIG. 5 is a line graph of blood glucose correction of STZ-057BL/6 with implanted 5 mm zwitterionic spheres encapsulating rat islets (800 clusters per mouse).

FIG. 5 is a line graph showing the differences in blood glucose as a function of the crosslinker, comparing 5 kD and 2 kD crosslinkers.

Example 2: Applying Zwitterionic Coatings to the Surfaces of Biomaterials

Materials 2-(Methacryloyloxy)ethyl 2-(trimethylammonio)ethylphosphate and (R)-α-lipoic acid were purchased from TCI Chemicals Inc. 2-aminoethyl methacrylate hydrochloride, 4-(dimethylamino)pyridine (DMAP), N-(3-dimethylaminopropyl)-N-ethylcarbodiimide hydrochloride (EDC.HCl), methanol, N,N-dimethylacetamide, dichloromethane (DCM), dimethylformamide (DMF), triethylamine (NEt$_3$), sodium borohydride (NaBH$_4$), 4-cyano-4-(phenylcarbonothioylthio)pentanoic acid, 4,4'-azobis(4-cyanovaleric acid), and dopamine hydrochloride salt were purchased from Sigma-Aldrich. Regenerated Cellulose Ester dialysis membrane tubing (2 kDa) was purchased from Spectrum Labs. Polystyrene microspheres (0.5 mm) was purchased from Phosphorex Inc. Cy3-conjugated anti-mouse alpha smooth muscle actin antibody was purchased from Sigma Aldrich. Filamentous actin (F-actin)-specific Alexa Fluor 488 conjugated Phallaoidin, and DAPI were purchased from Life Technologies.

Methods

Instrumentation $^1$H NMR and $^{13}$C NMR spectra were recorded on Varian Inova 500 MHz NMR spectrometer, using the residual proton resonance of the solvent as the internal standard. Chemical shifts are reported in parts per million (ppm). High resolution mass spectral (HRMS) data were obtained on 7 Tesk Bruker Fourier-Transform Ion Cyclotron Resonance Mass Spectrometer. Molecular weight and PDI values of the polymers were estimated by GPC in aqueous buffer containing 0.05 M sodium nitrate. One guard column and three Tosoh GMPWxL columns were calibrated with poly(ethylene oxide) standards. Flow rate was set to 1.0 mL/min and Viscotek refractive index detector was used for conventional calibration.

Phase contrast imaging of the retrieved capsules were performed using an EVOS X1 microscope. For bright-field imaging of retrieved materials, A Leica Stereoscopic microscope was used. A Zeiss LSM 700 system with ZEN microscope software was used to image and analyze the stained microspheres.

All XPS measurements were performed using PHI Versaprobe II X-ray photoelectron spectrometer from Physical Electronics with a monochromated Al Kα X-ray source (1486.6 eV) and operated at a base pressure of 1×10$^{-9}$ Torr during XPS analysis. The analysis area was 200 μm with a take-off angle of 45°.

Synthesis of Lipoic Acid Methacrylate

To a suspension of 2-aminoethyl methacrylate hydrochloride (5.0 g, 27.17 mmol) in dichloromethane (100 mL) was added triethylamine (4.54 mL, 32.60 mmol) at RT and stirred for a few minutes. (R)-α-lipoic acid (5.61 g, 27.17 mmol) was added. The mixture was cooled to 0° C., and then DMAP (1.66 g, 13.59 mmol) was added followed by EDC.HCl (7.81 g, 40.76 mmol). The reaction mixture was stirred under $N_2$ from 0° C. to RT overnight, washed with 1N HCL (100 mL×2), saturated $NaHCO_3$ (100 mL×2) and brine (100 mL). The organic phase was dried over $MgSO_4$. After the evaporation of solvent, the crude polymer was purified by flash chromatography (80 g ISCO silica gel column) with 10-50% EtOAc/hexane elution to give 7.80 g (90%) of the product as a yellow solid. $^1H$ NMR (500 MHz, $CDCl_3$): δ 6.13 (s, 1H), 5.81 (s, 1H), 5.63-5.59 (m, 1H), 4.28-4.22 (m, 2H), 3.62-3.52 (m, 3H), 3.23-3.07 (m, 2H), 2.50-2.41 (m 1H), 2.24-2.16 (m, 2H), 1.97-1.39 (m, 10H); $^{13}C$ NMR (500 MHz, $CD_3OD$): δ 176.2, 168.6, 137.6, 126.5, 64.3, 57.5, 41.3, 39.4, 39.3, 36.8, 35.7, 29.8, 26.7, 18.5; HRMS calculated for $C_{14}H_{23}NO_3S_2$ 318.1192, found 318.1189 [M+H].

Synthesis of Poly(MPC) Polymer 2-(Methacryloyloxy)ethyl 2-(trimethylammonio)ethylphosphate (2.0 g, 6.78 mmol), lipoic acid methacrylate (113 mg, 0.35 mmol), 4-cyano-4-(phenylcarbonothioylthio)pentanoic acid (10 mg, 0.035 mmol) and 4,4'-azobis(4-cyanovaleric acid (2.0 mg, 0.0071 mmol) were weighed in a weighing boat and transferred into a 10 ml of Schlenk flask. Methanol (3.6 mL) and N,N-dimethylacetamide (2.4 mL) were added. The flask was sealed with a rubber septum. The mixture was vortexed to get a homogenous solution, which was purged with nitrogen for 10 minutes. The flask was immersed in a preheated oil bath at 70° C. After 4 hr, the reaction was terminated by rapid cooling and exposure to air. The polymer was purified by dialysis in water. After lyophilization, a pinkish solid (2.09 g) was obtained. The resultant polymer was dissolved in mixed solvents of Methanol (5 mL) and water (10 mL), and then solution was cooled to 0° C. under $N_2$ atmosphere. A freshly prepared solution of $NaBH_4$ (200 mg) in water (2 mL) was slowly added. The reaction was stirred at 0° C. for 1.5 h, and then pH was adjusted to 3-4 by adding 2N HCl. The product was dialyzed against water using 1 kDa MWCO dialysis membrane in a cold room (4° C.) at dark for 2 days. After lyophilization, product (1.96 g) was obtained as a white solid, and stored at −20° C. $M_n$(aq. GPC): 27 kDa, PDI: 1.3.

Fabrication of Alginate Microspheres

Detailed procedure for alginate microsphere preparation can be found in Vegas, et al., Nat. Biotechnol. 2016, 34, 345, and Veiseh, et al. Nat. Mater. 2015, 14, 643. Briefly, 0.5 mm alginate spheres were prepared using a custom-built device, consisting of a voltage generator, a vertical syringe pump, and a grounded autoclavable glass collector. A 1.4% solution of a commercially available ultrapure-sterile alginate (Pronova SLG20, NovaMatrix, Norway) solution prepared in 0.9% saline was pumped out into a glass dish containing 20 mM $BaCl_2$ solution. Capsules are then collected, and washed with HEPES buffer and stored at 4° C. until use. The following settings were used to make 0.5 mm capsules; 25 G blunt needle, a voltage of 5 kV, and 200 μL/min flow rate. For animal studies, immediately before the implantation, capsules were washed additional two times with 0.9% sterile saline solution.

Modification of Microspheres with Zwitterionic Polymers

Figure 6A:
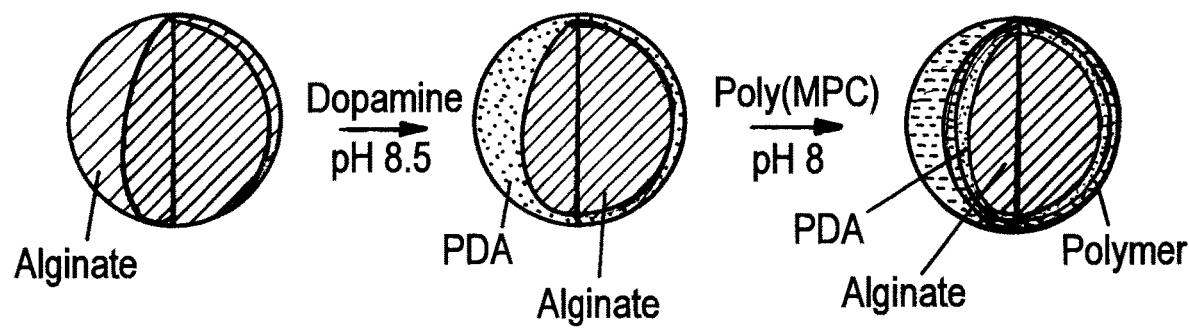
FIGS. 6A and 6B are schematics of the process of coating of the surface of alginate microspheres with zwitterionic polymers.

As shown in FIG. 6, Alginate and/or PS microparticles with diameters of 0.5 mm in Tris HCl buffer (10 mM, pH 8.5) were simply shaken on a benchtop orbital shaker, then a stock solution of dopamine hydrochloride in the same Tris buffer was added to the microspheres with a final concentration of 3 mg/mL. The resultant mixtures were shaken at room temperature for 18 hours, and then washed multiple times with Tris buffer until to get a clear supernatant solution. Dopamine coated spheres were then taken into Tris buffer solution (pH 8, 10 mM). To this solution, a stock solution of poly(MPC) in the same buffer was added to give a final 4 w/v % of poly(MPC) concentration. The final reaction mixture was then purged with nitrogen for 10 minutes to deoxygenate the reaction solution. The resultant mixtures were shaken at RT for 18-20 hours in dark, and rinsed multiple times with Tris buffer and stored in 0.9% saline solution at 4° C. until further use.

Implantation and Retrieval of Microspheres

All animal protocols were approved by Animal Care Committees at MIT, and all surgical procedures, and postoperative care was supervised by MIT Division of Comparative Medicine veterinary staff. Immunocompetent male C57BL/6J (Jackson Laboratory, ME) mice were used for all in vivo studies.

Cell Staining and Confocal Immunofluorescence

The retrieved materials were fixed overnight in 4% paraformaldehyde overnight, and then samples were washed twice with KREBS buffer, permeabilized for 30 min using a 0.1% Triton X-100 solution, and subsequently blocked for 1 hour using a 1% BSA solution. Next, the spheres were incubated for 1 hour in staining solution consisting of DAPI (500 nM), specific marker probes (1:200 dilution) in BSA. After 45 minutes in dark at RT, staining solution was aspirated, and then spheres were washed three times with a 0.1% Tween 20 solution, and maintained in a 50% glycerol solution. Spheres were then transferred to glass bottom dishes and imaged using an LSM 700 point scanning confocal microscope (Carl Zeiss) equipped with 5 and 10× objectives.

FACS Analysis

Single-cell suspensions of freshly excised tissues were prepared using a gentleMACS Dissociator (Miltenyi Biotec, Auburn, Calif.) according to the manufacturer's protocol. Single-cell suspensions were prepared in a passive PEB dissociation buffer (1×PBS, pH 7.2, 0.5% BSA, and 2 mM EDTA) and suspensions were passed through 70 μm filters (Cat. #22363548, Fisher Scientific, Pittsburgh, Pa.). This process removed the majority of cells adhered to the surface (>90%).[25] All tissue and material sample-derived, single-cell populations were then subjected to red blood cell lysis with 5 ml of 1×RBC lysis buffer (Cat. #00-4333, eBioscience, San Diego, Calif., USA) for 5 min at 4° C. The reaction was terminated by the addition of 20 ml of sterile 1×PBS. The cells remaining were centrifuged at 300-400 g at 4° C. and resuspended in a minimal volume (~50 μl) of eBioscience Staining Buffer (cat. #00-4222) for antibody incubation. All samples were then co-stained in the dark for 25 min at 4° C. with two of the fluorescently tagged monoclonal antibodies specific for the cell markers CD68 (Alexa-647, Clone FA-11, Cat. #11-5931, BioLegend), Ly-6G (Gr-1) (Alexa-647, Clone RB6-8C5, Cat. #108418, BioLegend), CD11b (Alexa-488, Clone M1/70, Cat. #101217, BioLegend). Two ml of eBioscience Flow Cytometry Staining Buffer (cat. #00-4222, eBioscience) was then added, and the samples were centrifuged at 400-500 g for 5 min at 4° C. Supernatants were removed by aspiration, and this wash step was repeated two more times with staining buffer. Following the third wash, each sample was resuspended in 500 μl of Flow Cytometry Staining Buffer and run through a 40 μm filter (Cat. #22363547, Fisher Scientific) for eventual FACS analysis using a BD FACSCalibur (cat. #342975), BD Biosciences, San Jose, Calif., USA). For proper background and laser intensity settings, unstained, single antibody, and IgG (labeled with either Alexa-488 or Alexa-647, BioLegend) controls were also run.

Results

This example demonstrates a platform approach to coating biomaterial surfaces with anti-biofouling zwitterionic polymers using facile and scalable methodology. The effect of this coating on in vivo biocompatibility was assessed. This approach employs, first, modification of the surface with mussel-inspired polydopamine (PDA) films by oxidative self-polymerization of dopamine, and followed by conjugation of thiol-containing zwitterionic polymers to this PDA layer. It has been previously shown that simple immersion of virtually any substrate in an alkaline aqueous solution of dopamine results in spontaneous deposition of a thin PDA film, with subsequent reactivity of this film toward amines and thiols to form ad-layers. (Lee, et al., Science 2007, 318, 426; Lee, et al., Adv. Mater. 2009, 21, 431; and Ham, et al., Angew. Chem. Int. Ed. 2011, 50, 732). Using this conjugation method, zwitterionic polymers were attached on to the surface of biomaterials and in vivo examined the efficacy of the coating approach to reduce host immune responses and fibrosis to implanted biomaterials.

As a preliminary evaluation, zwitterionic polymers were conjugated onto the surface of alginate hydrogel microspheres. Alginate, a naturally occurring anionic biopolymer, forms hydrogels in aqueous conditions through the addition of divalent cations such as $Ca^{2+}$ and $Ba^{2+}$. Commonly prepared as gelled microspheres, alginate has been broadly used as biomaterials for drug delivery, tissue engineering, and cell transplantation. (Lee and Mooney, Prog. Poly. Sci. 2012, 37, 106.) However, following implantation, alginate microspheres can promote the formation of excessive fibrous overgrowth around the microspheres, compromising function of the implant. (Vegas, et al., Nat. Biotechnol. 2016, 34, 345; King, et al., J. Biomed. Mater. Res. 2001, 57, 374; and Scharp and Marchetti, P. Adv. Drug. Deliv. Rev. 2014, 67-68, 35.) Therefore, the method for coating biomaterials with zwitterionic polymers was evaluated in order to reduce the fibrotic response to alginate microspheres. Polycations, such as poly-L-lysine (PLL), are commonly used to coat alginate surfaces to reduce fibrosis. (Ma, et al., Adv. Mater. 2011, 23, H189; Spasojevic, et al., PLoS One, 2014, 9, e109837; and Lim and Sun, Science, 1980, 210, 908).

Figure 6B:
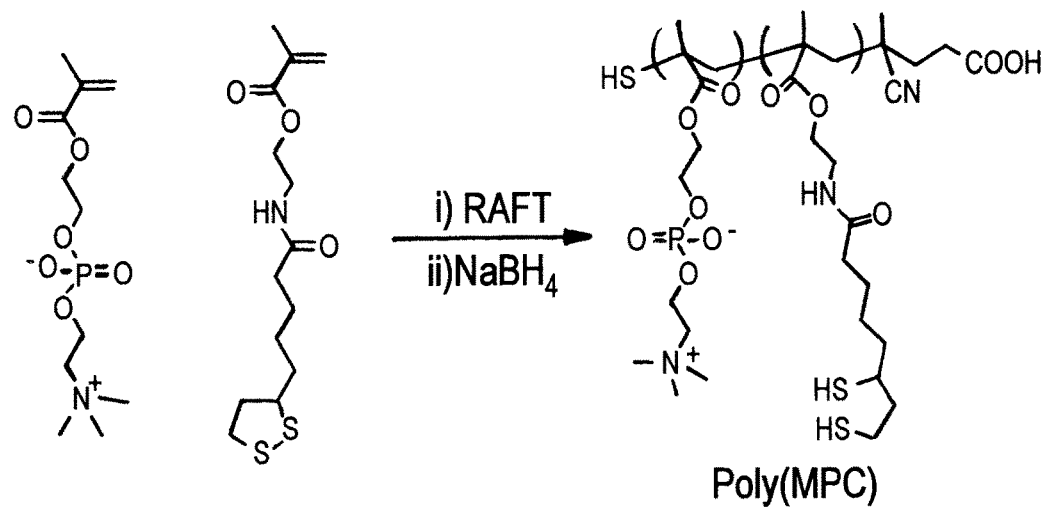

To assess the effect of zwitterionic coatings on the biocompatibility of alginate microspheres, a zwitterionic phosphorylcholine polymer with pendant dithiol-containing comonomers was synthesized. Phosphorylcholine polymers have several advantages as coating materials, including hydrophilicity, high water solubility and anti-biofouling properties. (Seetho, et al., ACS Macro Lett. 2015, 4, 505; and Chen, et al., Macromolecules 2013, 46, 119) Reversible addition-fragmentation chain transfer (RAFT) polymerization of methacryloyloxyethyl phosphorylcholine (MPC) and lipoic acid methacrylate monomers followed by disulfide reduction yielded a poly(MPC) with free pendant thiol groups along the backbone (FIG. 6B). (Chen, et al., Macromolecules 2013, 46, 119) After successfully synthesizing poly(MPC) copolymers with free thiol groups ($M_n$: 27 kDa, PDI: 1.3), these polymers were immobilized onto $Ba^{2+}$-crosslinked alginate hydrogel microspheres (_0.5 mm diameter), a size shown to produce higher level of fibrosis in vivo. (Veiseh, et al. Nat. Mater. 2015, 14, 643) Alginate microspheres were coated with PDA by immersion for 18-20 hours in a 3 mg/mL dopamine solution prepared in 10 mM Tris buffered saline (pH 8.5), followed by multiple rinses with Tris buffer. (Kim, et al., Angew. Chem. Int. Ed. 2014, 53, 14443) PDA coated alginate microspheres were then treated with poly(MPC) polymer in Tris buffer (pH 8.0) at room temperature for 18-24 hours. Using X-ray photoelectron spectroscopy (XPS), the characteristic N is peak of PDA at 399.5 eV and a distinct P 2p peak of poly(MPC) polymer at 134 eV was observed, confirming successful coating of alginate microspheres. (Ham, et al., Angew. Chem. Int. Ed. 2011, 50, 732)

Figure 7A:
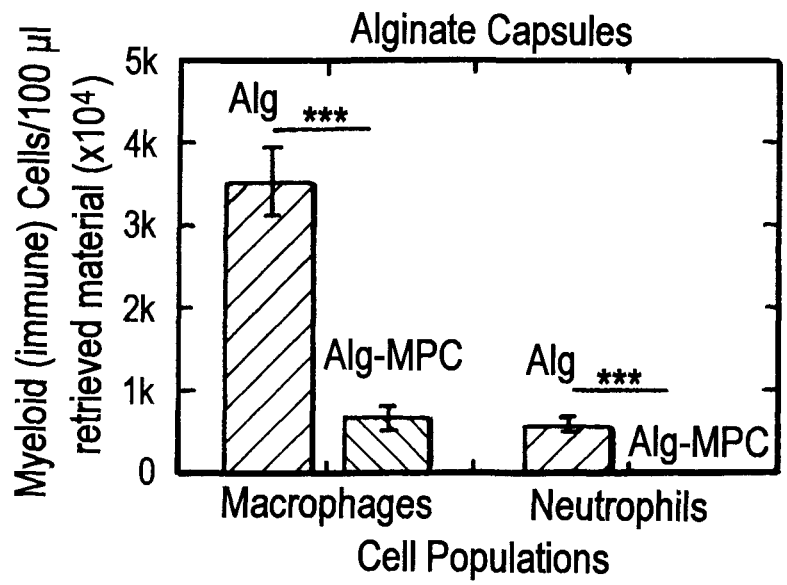
FIGS. 7A and 7B are bar graphs of myeloid cells retrieved from implanted microspheres.

To investigate the effect of poly(MPC) coating on the foreign body reactions, MPC-modified alginate microspheres and controls (polystyrene) microspheres were implanted into the intraperitoneal space of immunocompetent C57BL/6J mice (n=5). After 14 days, the capsules were retrieved and examined for cellular overgrowth and fibrosis. Dark field phase contrast microscopy of retrieved unmodified capsules showed extensive cellular deposition on unmodified microspheres, whereas poly(MPC) coated microspheres showed little cellular deposition (FIG. 7A). Immunofluorescence imaging was used to further characterize the cellular deposition on the microsphere surface. Staining of the retrieved microspheres using DAPI (nuclear stain), F-actin (cellular cytoskeleton marker) and α-smooth muscle actin (α-SMA, fibrosis-associated myofibroblast marker) revealed very little cellular staining on zwitterionic-coated microspheres (FIG. 7A). (Vegas, et al., Nat. Biotechnol. 2016, 34, 345; and Veiseh, et al., Nat. Mater. 2015, 14, 643) In contrast, the unmodified alginate microspheres stained extensively for these markers, indicating significant fibrosis formation on the unmodified spheres.

To ensure that the reduction in cellular deposition on modified alginate microspheres was attributable to coating with poly(MPC), PDA-coated alginate microspheres without subsequent zwitterionic modification were also evaluated. 14 days following implantation, phase contrast microscopy of these PDA microspheres showed clumping and extensive cellular deposition. This supports the function of the zwitterionic poly(MPC) coating in mitigating the fibrotic tissue response.

Figure 7B:
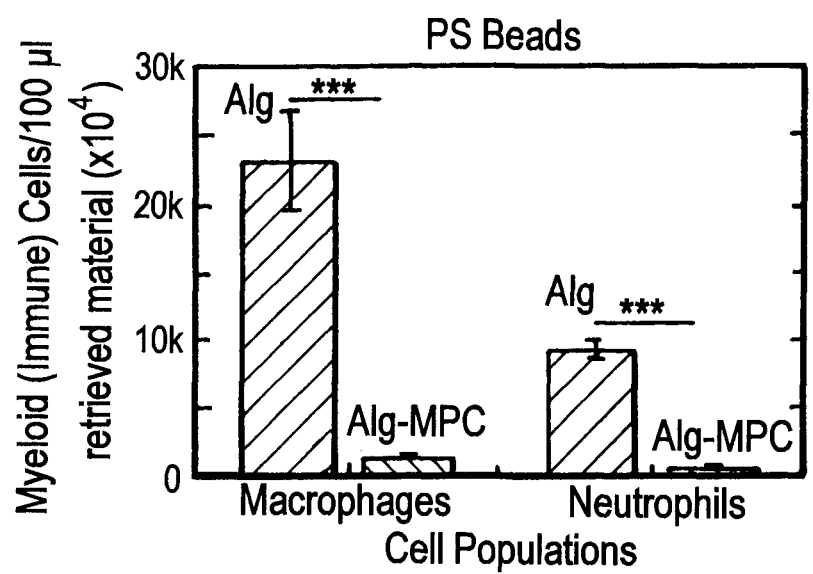
Figure 8A:
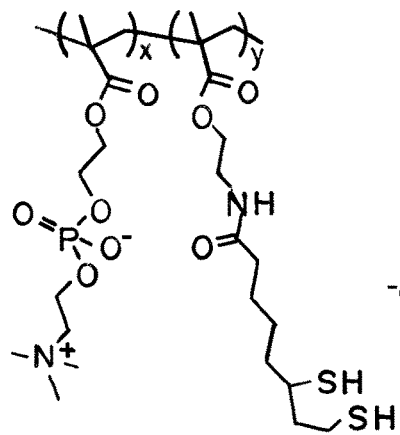
FIG. 8A-8T show exemplary zwitterionic polymers that have been synthesized.
Figure 8B:
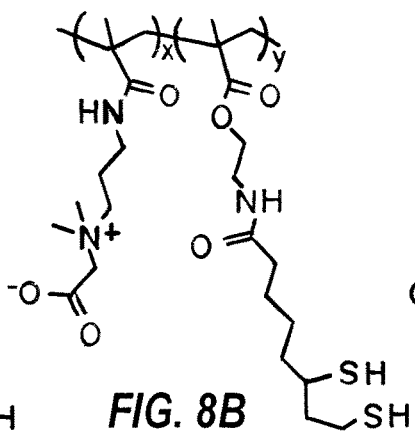
Figure 8C:
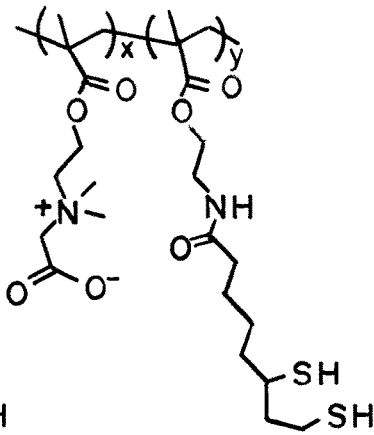
Figure 8D:
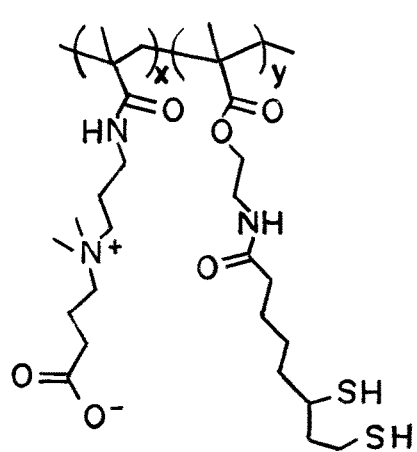
Figure 8E:
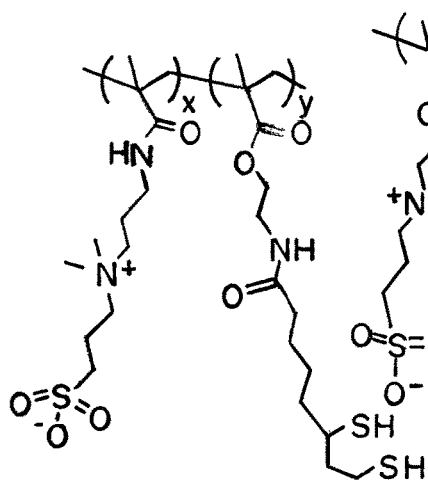
Figure 8F:
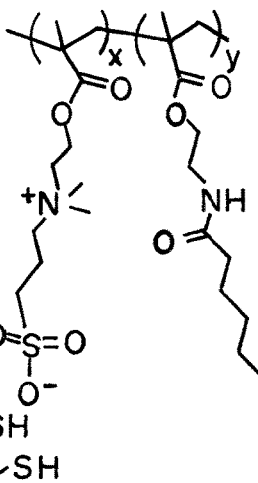
Figure 8G:
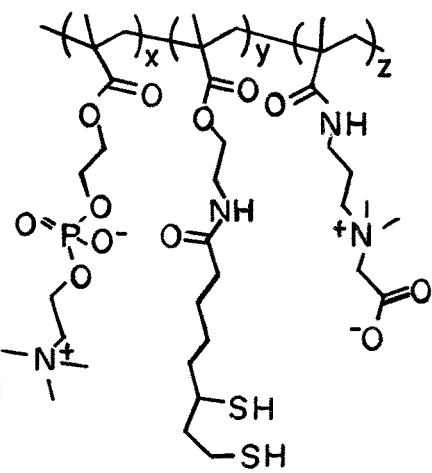
Figure 8H:
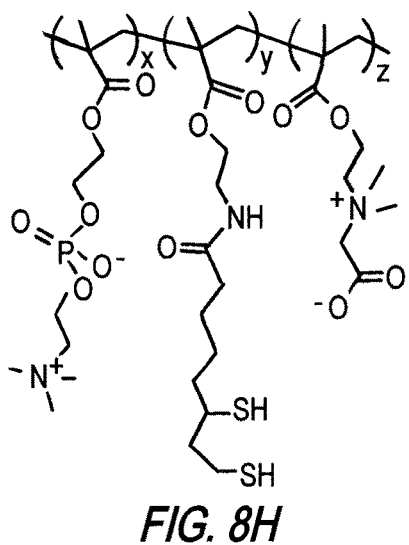
Figure 8I:
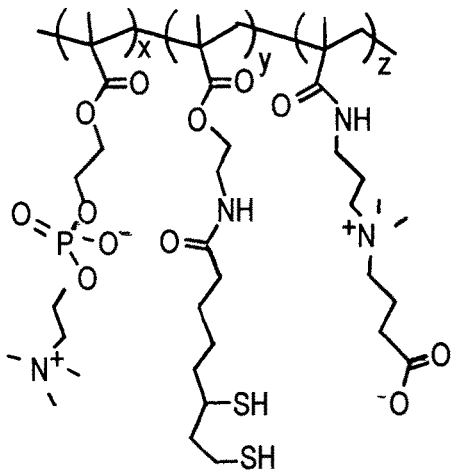
Figure 8J:
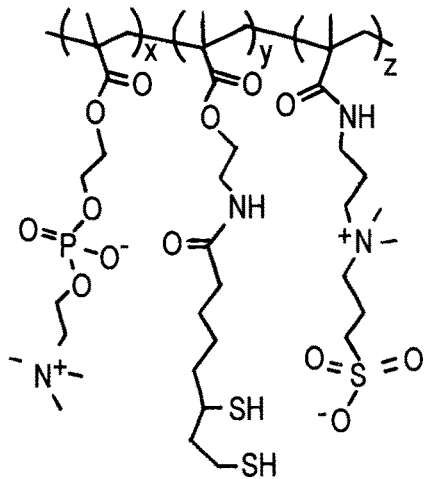
Figure 8K:
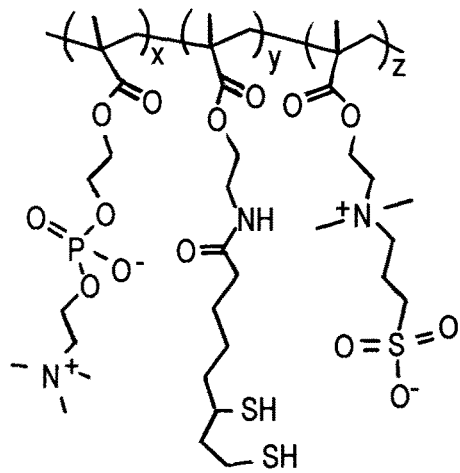
Figure 8L:
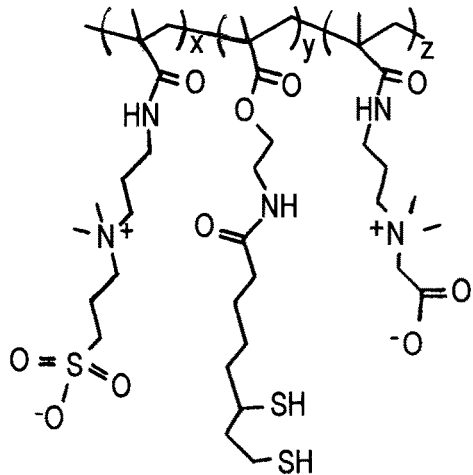
Figure 8M:
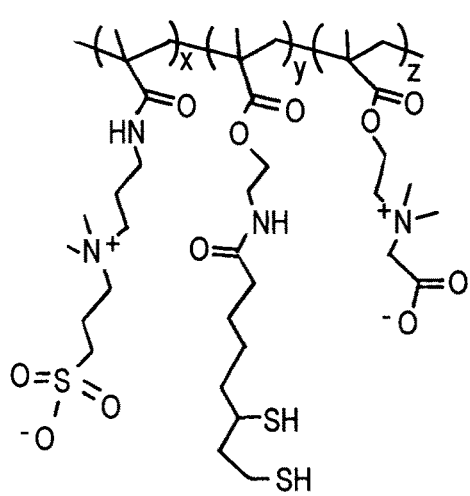
Figure 8N:
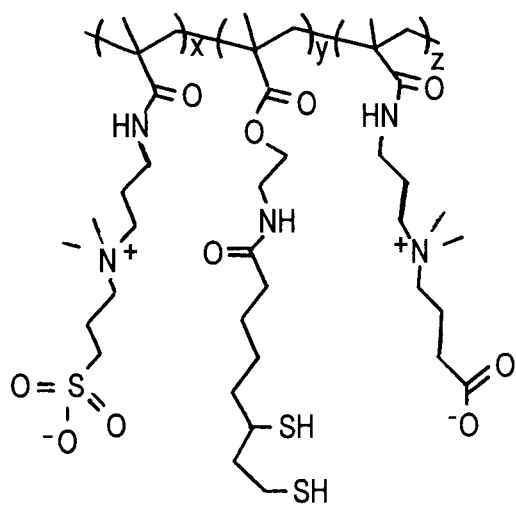
Figure 8O:
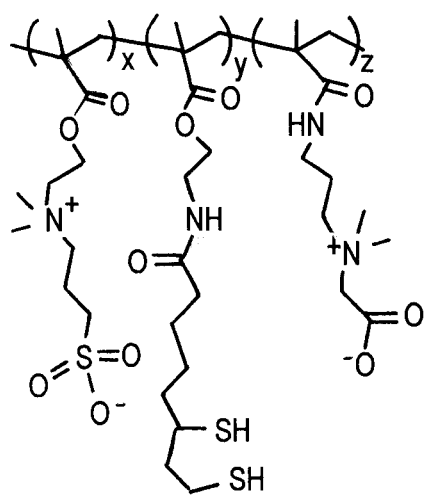
Figure 8P:
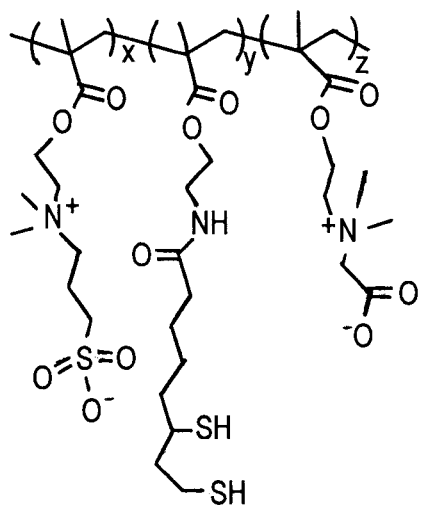
Figure 8Q:
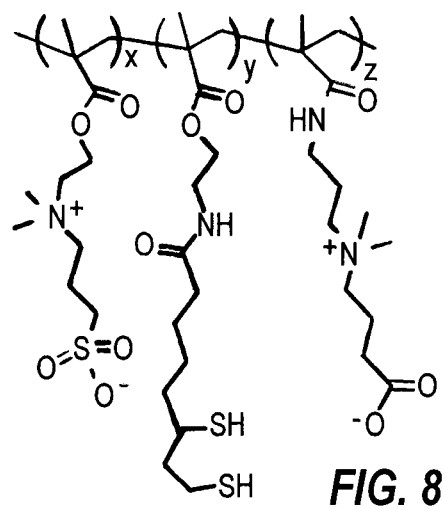
Figure 8R:
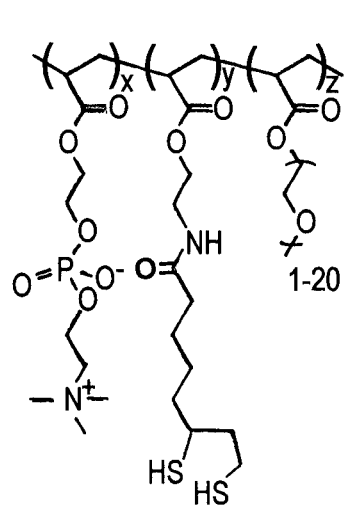
Figure 8S:
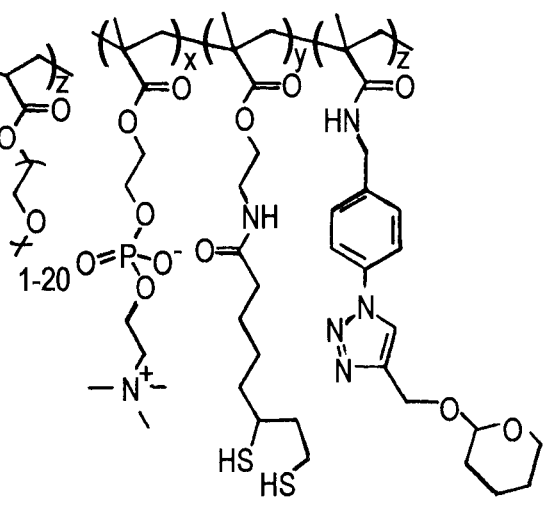
Figure 8T:
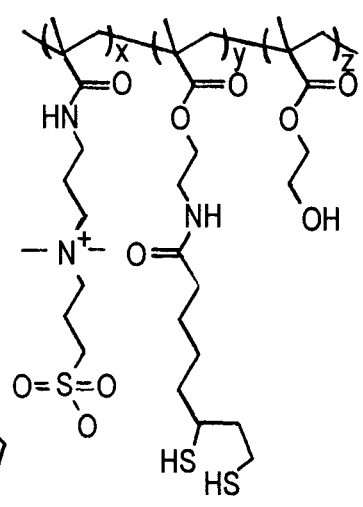

The versatility of this anti-fibrotic effect for other biomaterials was also evaluated. Since the PDA coating procedure can be used on effectively all types of materials, the coating strategy should likewise be material-independent. Polystyrene (PS), when used as a biomaterial, is known to induce a more severe fibrotic reaction when implanted. (Ma, et al., Adv. Mater. 2011, 23, H189; Veiseh, et al. *Nat. Mater.* 2015, 14, 643; and Bratlie, K. et al. Plos One 2010, 5(4), e10032) Therefore, polystyrene microspheres (0.5 mm) were coated with poly(MPC) polymer and implanted into mice to explore the versatility of this approach to reducing fibrosis of implanted materials. Phase contrast microscopy of retrieved PS microspheres confirms that unmodified materials become heavily encased in fibrotic tissue (FIG. 7B). However, poly(MPC) coated PS microspheres remained completely free of fibrosis. Immunofluorescence imaging of retrieved PS microspheres confirmed poly(MPC) coating resulted in a dramatic reduction in cellular depositions on PS microspheres (FIG. 7B). These results support the versatility of this coating methodology to a variety of implantable materials in order to control the fibrotic tissue response.

Additionally, flow cytometry analysis was performed on the cellular deposition from retrieved microspheres to quantify immune cells (macrophages and neutrophils) present onto the microsphere surface. See FIG. 4. It was found that poly(MPC) coating reduced the macrophage adhesion by A fold for alginate and _25 fold for PS microspheres. Zwitterioninc coating seems to completely abrogate neutrophil attachment to both materials. The reduction of immune cells on the material surface confirms findings from microscopy analysis for a reduction in cellular deposition attributable to poly(MPC) coating.

In summary, a facile and versatile method for surface modification of biomaterials with anti-fouling zwitterionic polymers has been demonstrated. This approach improved the biocompatibility of implanted materials by reducing the surface-mediated fibrotic reaction in vivo. This methodology is broadly applicable to endowing a variety of materials with zwitterionic polymer surface coatings, as demonstrated in data collected for both alginate and PS microspheres. This approach to surface modification with zwitterionic polymers can be applied to virtually any implantable biomaterial, with broad use for cell transplantation, drug delivery, tissue engineering, and biomedical device implantation.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A biocompatible polymer comprising one or more monomer subunits A and B, wherein the polymer optionally further comprises one or more monomer subunits C;
   wherein each A is a zwitterionic monomer;
   wherein each B is a monomer with a reactive side chain, wherein the reactive side chain is Formula IV: d-$R_1$-Y comprising an amide bond and further comprising an ester, ether, acylhydrazine, carbamate, ketone, carbonate, sulfone, sulfoxide, thioether, azo, or aldimine;
   wherein each C is independently a hydrophobic monomer or a neutral hydrophilic monomer;
     wherein d is the point of covalent attachment of the reactive side chain to the backbone of the polymer;
   wherein:
     $R_1$ is unsubstituted alkyl, substituted alkyl, unsubstituted alkenyl, substituted alkenyl, unsubstituted alkynyl, substituted alkynyl, unsubstituted aryl, substituted aryl, unsubstituted heteroaryl, substituted heteroaryl, unsubstituted alkoxy, unsubstituted aroxy, substituted aroxy, unsubstituted alkylthio, substituted alkylthio, unsubstituted arylthio, substituted arylthio, unsubstituted carbonyl, unsubstituted carboxyl, unsubstituted amido, unsubstituted sulfonyl, substituted sulfonyl, unsubstituted sulfamoyl, substituted sulfamoyl, unsubstituted phosphonyl, substituted phosphonyl, unsubstituted polyaryl, substituted polyaryl, unsubstituted $C_3$-$C_{20}$ cyclic, substituted $C_3$-$C_{20}$ cyclic, unsubstituted $C_3$-$C_{20}$ heterocyclic, substituted $C_3$-$C_{20}$ heterocyclic, amino acid, poly(lactic-co-glycolic acid), peptide, or polypeptide group; and Y is propane-1,3-dithiol, 1,2-dithiolan-3-yl, 1,2-dithiol-3-ylidene, —SH, maleimide, aziridine, —$N_3$, —CN, acryloyl, acrylamide, —C(O)OR$_2$, —C(O)R$_3$, vinyl sulfone, cyanate, thiocyanate, isocyanate, isothiocyanate, alkoxysilane, vinyl silane, silicon hydride, —NR$_4$R$_5$, acetohydrazide, acyl azide, acyl halides, N-hydroxysuccinimide ester, sulfonyl chloride, glyoxal, epoxide, carbodiimides, aryl halides, or imido ester;

or
   $R_1$ is unsubstituted alkyl, substituted alkyl, unsubstituted alkenyl, substituted alkenyl, unsubstituted alkynyl, substituted alkynyl, unsubstituted aryl, substituted aryl, heteroaryl, substituted heteroaryl, unsubstituted alkoxy, substituted alkoxy, aroxy, substituted aroxy, unsubstituted alkylthio, substituted alkylthio, unsubstituted arylthio, substituted arylthio, unsubstituted carbonyl, substituted carbonyl, unsubstituted carboxyl, substituted carboxyl, unsubstituted amino, substituted amino, unsubstituted amido, substituted amido, unsubstituted sulfonyl, substituted sulfonyl, unsubstituted sulfamoyl, substituted sulfamoyl, unsubstituted phosphonyl, substituted phosphonyl, unsubstituted polyaryl, substituted polyaryl, unsubstituted $C_3$-$C_{20}$ cyclic, substituted $C_3$-$C_{20}$ cyclic, unsubstituted $C_3$-$C_{20}$ heterocyclic, substituted $C_3$-$C_{20}$ heterocyclic, amino acid, poly(ethylene glycol), poly(lactic-co-glycolic acid), peptide, or polypeptide group; and Y is propane-1,3-dithiol, 1,2-dithiolan-3-yl, 1,2-dithiol-3-ylidene, —SH, maleimide, aziridine, —$N_3$, —CN, acrylamide, —C(O)OR$_2$, —C(O)R$_3$, vinyl sulfone, cyanate, thiocyanate, isocyanate, isothiocyanate, vinyl silane, silicon hydride, acetohydrazide, acyl azide, acyl halides, N-hydroxysuccinimide ester, sulfonyl chloride, glyoxal, carbodiimides, aryl halides, or imido ester;
   wherein $R_2$ and $R_4$ are, independently, hydrogen, amino, hydroxyl, thiol, oxo, phosphate, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, substituted or unsubstituted $C_1$-$C_{10}$ alkoxy, substituted or unsubstituted $C_1$-$C_{10}$ alkylamino, substituted or unsubstituted $C_1$-$C_{10}$ alkylthio, unsubstituted aryl, substituted aryl, unsubstituted heteroaryl, substituted heteroaryl, unsubstituted alkoxy, substituted alkoxy, unsubstituted aroxy, substituted aroxy, unsubstituted alkylthio, substituted alkylthio, unsubstituted arylthio, substituted arylthio, unsubstituted carbonyl, substituted carbonyl, unsubstituted carboxyl, substituted carboxyl, amino, substituted amino, amido, substituted amido, polyaryl, substituted polyaryl, $C_3$-$C_{20}$ cyclic, substituted $C_3$-$C_{20}$ cyclic, unsubstituted $C_3$-$C_{20}$ heterocyclic, or substituted $C_3$-$C_{20}$ heterocyclic;
   wherein $R_5$ is amino, hydroxyl, thiol, oxo, phosphate, substituted $C_1$-$C_{10}$ alkyl, substituted or unsubstituted $C_2$-$C_{10}$ alkenyl, substituted or unsubstituted $C_2$-$C_{10}$ alkynyl, substituted or unsubstituted $C_1$-$C_{10}$ alkoxy, substituted or unsubstituted $C_1$-$C_{10}$ alkylamino, substituted or unsubstituted $C_1$-$C_{10}$ alkylthio, unsubstituted aryl, substituted aryl, unsubstituted heteroaryl, substituted heteroaryl, unsubstituted alkoxy, substituted alkoxy, unsubstituted aroxy, substituted aroxy, unsubstituted alkylthio, substituted alkylthio, unsubstituted arylthio, substituted arylthio, unsubstituted carbonyl, substituted carbonyl, unsubstituted carboxyl, substituted carboxyl, amino, substituted amino, amido, substituted amido, polyaryl, substituted polyaryl, $C_3$-$C_{20}$ cyclic, substituted $C_3$-$C_{20}$ cyclic, unsubstituted $C_3$-$C_{20}$ heterocyclic, or substituted $C_3$-$C_{20}$ heterocyclic, wherein when $R_5$ is substituted $C_1$-$C_{10}$ alkyl, $R_5$ includes a secondary amine group; and
   wherein $R_3$ is amino, hydroxyl, thiol, oxo, phosphate, substituted $C_1$-$C_{10}$ alkyl, substituted or unsubstituted $C_2$-$C_{10}$ alkenyl, substituted or unsubstituted $C_2$-$C_{10}$ alkynyl, substituted or unsubstituted $C_1$-$C_{10}$ alkoxy, substituted or unsubstituted $C_1$-$C_{10}$ alkylamino, substituted or unsubstituted $C_1$-$C_{10}$ alkylthio, unsubstituted aryl, substituted aryl, unsubstituted heteroaryl, substituted heteroaryl, unsubstituted alkoxy, substituted alkoxy, unsubstituted aroxy, substituted aroxy, unsubstituted alkylthio, substituted alkylthio, unsubstituted arylthio, substituted arylthio, unsubstituted carbonyl, substituted carbonyl, unsubstituted carboxyl, substituted carboxyl, unsubstituted amino, substituted amino, unsubstituted amido, substituted amido, unsubstituted polyaryl, substituted polyaryl, unsubstituted $C_3$-$C_{20}$ cyclic, substituted $C_3$-$C_{20}$ cyclic, unsubstituted $C_3$-$C_{20}$ heterocyclic, or substituted $C_3$-$C_{20}$ heterocyclic.

2. The polymer of claim 1, wherein monomer subunits A, B, and C are in the ratio of x:y:z, respectively, wherein x and y are, independently, integers between 1 and 1000, inclusive, and wherein z is an integer between 0 and 1000, inclusive; and
wherein the polymer has n total monomer subunits, wherein n is an integer between 2 and 2000, inclusive.

3. The polymer of claim 1, wherein at least one A is a first zwitterionic monomer and at least one A is a second zwitterionic monomer.

4. The polymer of claim 3, wherein the first and second zwitterionic monomers are present in the polymer in a ratio of v:w, respectively, wherein v and w are, independently, integers between 1 and 1000, inclusive.

5. The polymer of claim 3, wherein at least one A is a third zwitterionic monomer.

6. The polymer of claim 5, wherein the first and third zwitterionic monomers are present in the polymer in a ratio of t:u, respectively, wherein t and u are, independently, integers between 1 and 1000, inclusive.

7. The polymer of claim 3, wherein the first zwitterionic monomer comprises a carboxybetaine group, wherein the second zwitterionic monomer comprises a phosphoryl choline group.

8. The polymer of claim 7, wherein the carboxybetaine group is —$CH_2$—$CH_2$—$N^+((CH_3)_2)$—$CH_2$—$CH_2$—$C(O)$—$O^-$.

9. The polymer of claim 7, wherein the phosphoryl choline group is —$CH_2$—$CH_2$—O—$P^-(O_2)$—O—$CH_2$—$CH_2$—$N^+((CH_3)_3)$.

10. The polymer of claim 4, wherein v is 3 and w is 7.

11. The polymer of claim 1, wherein at least one C is a neutral hydrophilic monomer and at least one C is a hydrophobic monomer.

12. The polymer of claim 11, wherein the neutral hydrophilic monomer and the hydrophobic monomer are present in the polymer in a ratio of q:s, respectively, wherein q and s are, independently, integers between 1 and 1000, inclusive.

13. The polymer of claim 1, wherein the reactive side chain comprises a sulfhydryl group.

14. The polymer of claim 1, wherein the reactive side chain is d-C(O)—O—$CH_2$—$CH_2$—NH—C(O)—$CH_2$—$CH_2$—$CH_2$—$CH_2$—CH(SH)—$CH_2$—$CH_2$—SH.

15. The polymer of claim 1, wherein at least one B is a first monomer with a first reactive side chain and at least one B is a second monomer with a second reactive side chain.

16. The polymer of claim 15, wherein the first monomer with the first reactive side chain and the second monomer with the second reactive side chain are present in the polymer in a ratio of d:e, respectively, wherein d and e are, independently, integers between 1 and 1000, inclusive.

17. The polymer of claim 2, wherein x is between 1 and 10, inclusive, y is between 1 and 10, inclusive, and z is 0.

18. The polymer of claim 2, wherein x is 10, y is 1, and z is 0.

19. The polymer of claim 1, wherein, prior to polymerization to form the polymer, the one or more monomer subunits A, B, and C each comprised a methacrylate group or a methacrylamide group, wherein, during polymerization to form the polymer, the methacrylate and methacrylamide groups react to form the polymer backbone.

20. The polymer of claim 1, comprising a structure selected from the group consisting of:

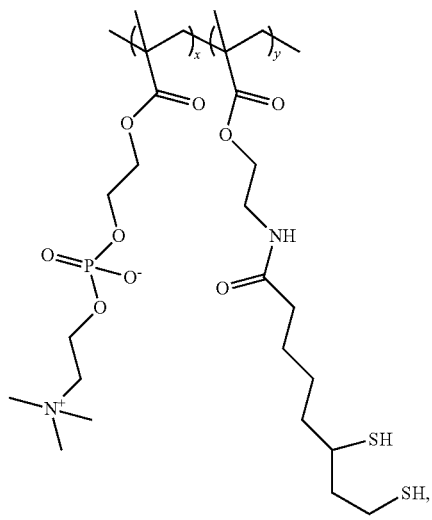

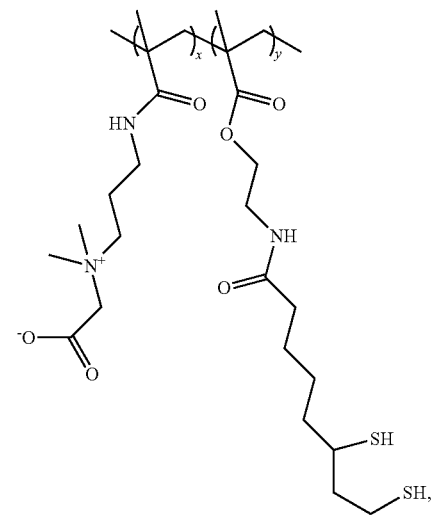

63
-continued
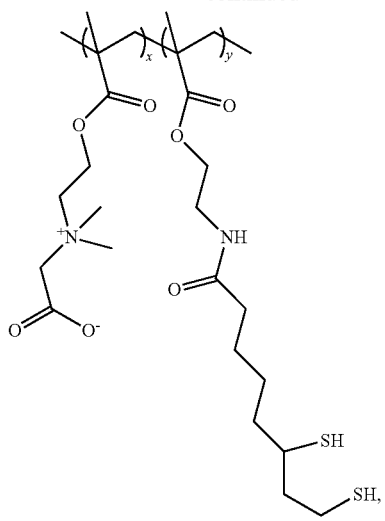
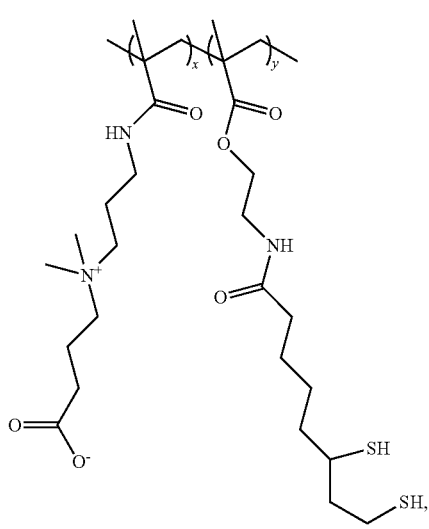
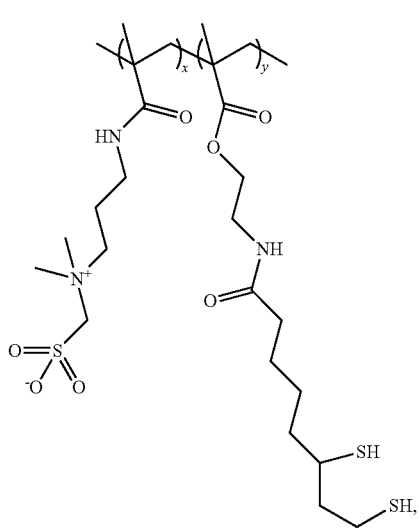
64
-continued
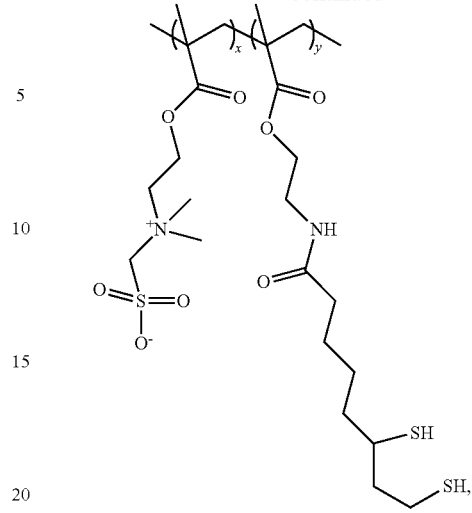
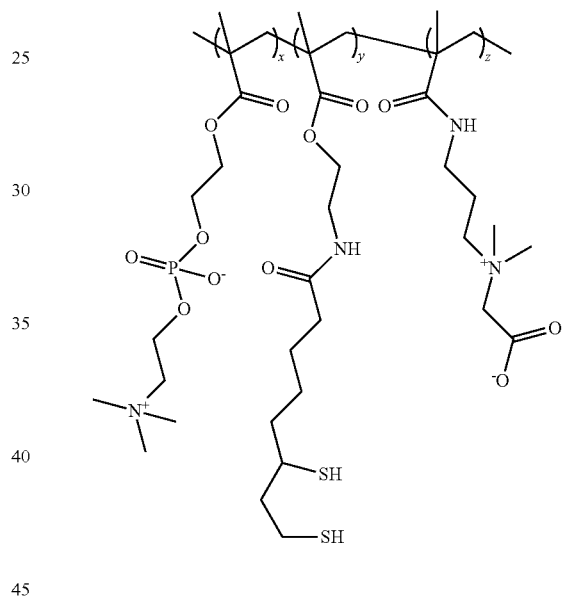
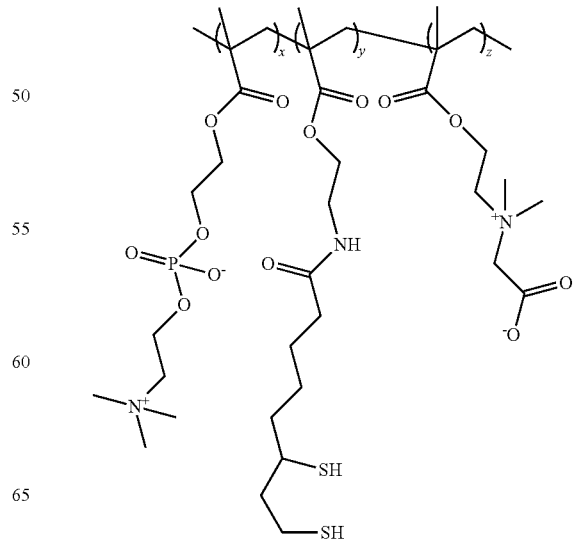

65
-continued
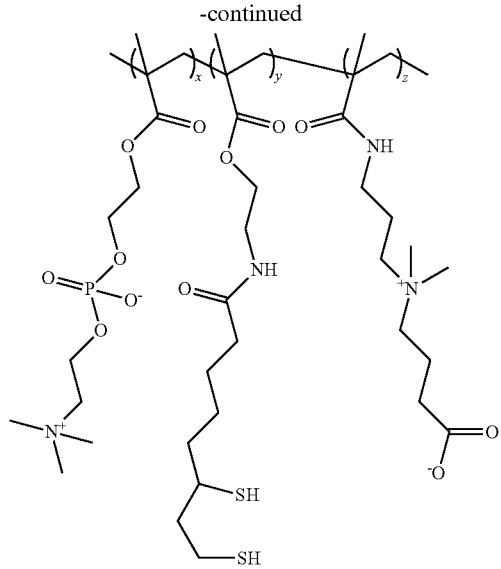
66
-continued
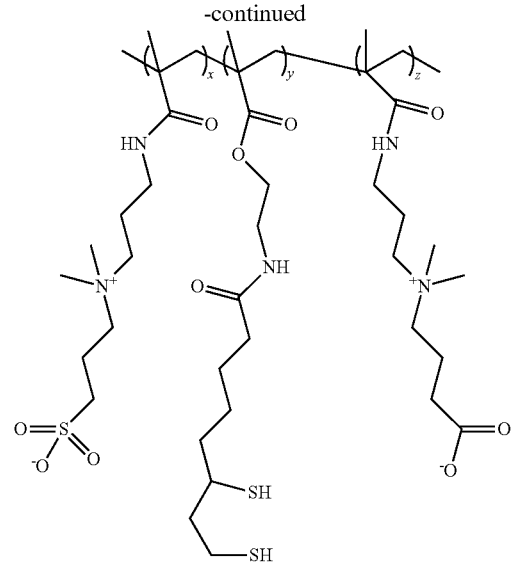
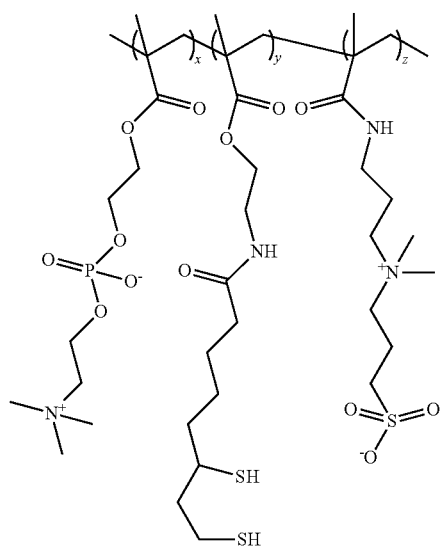
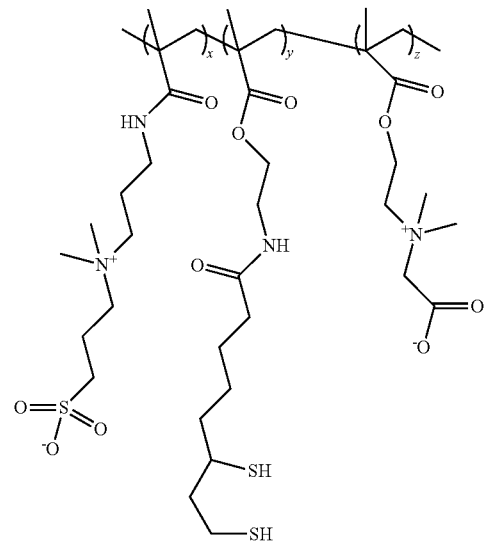
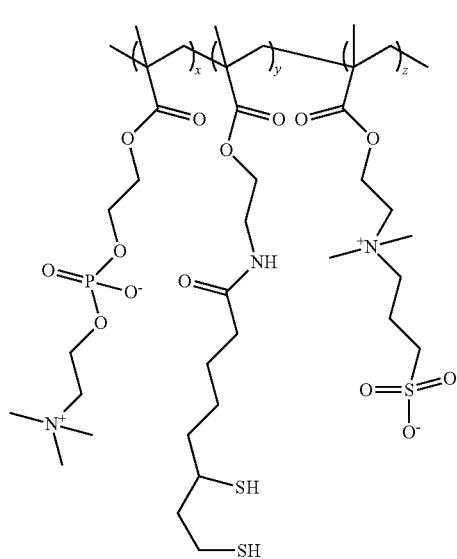
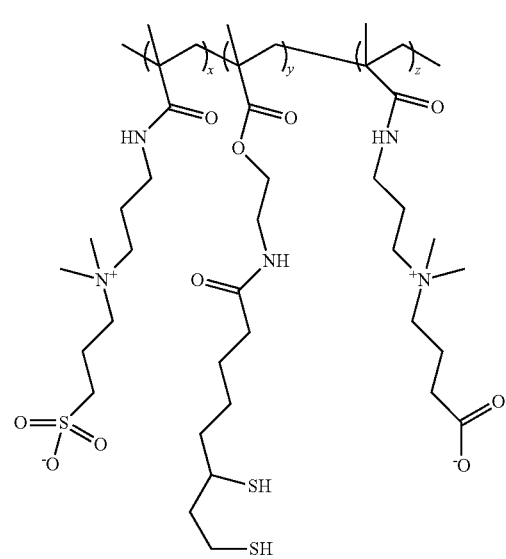

67
-continued
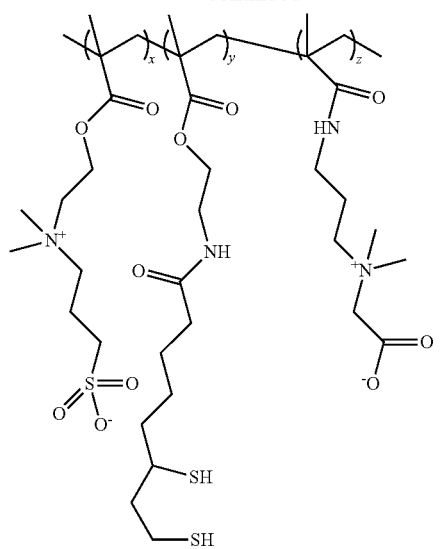
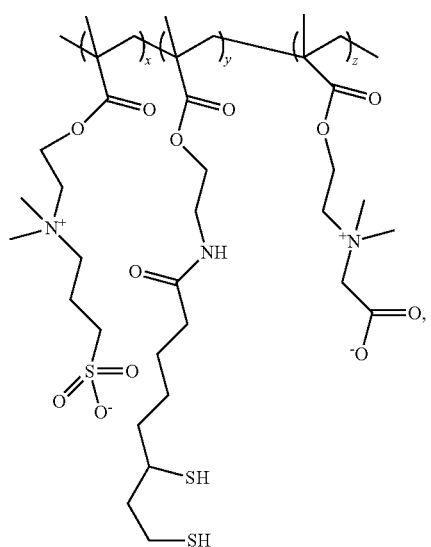
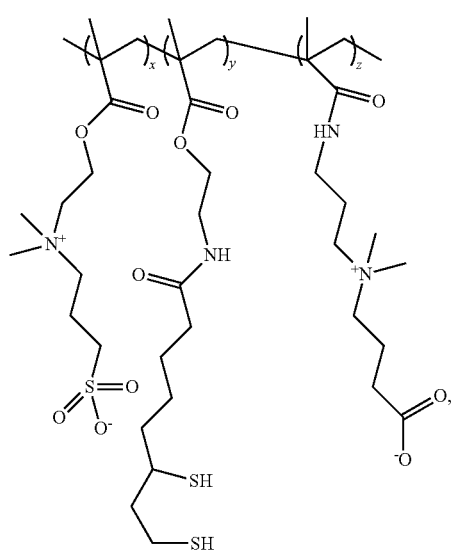
68
-continued
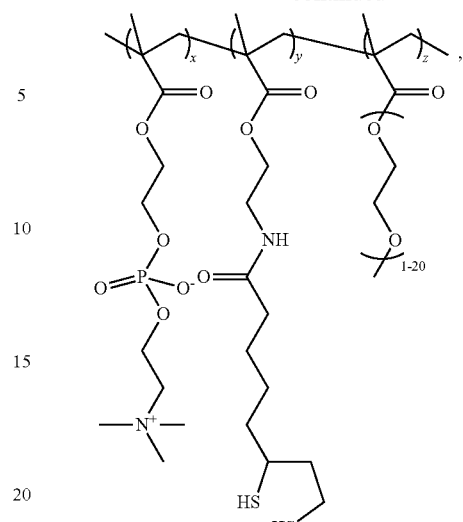
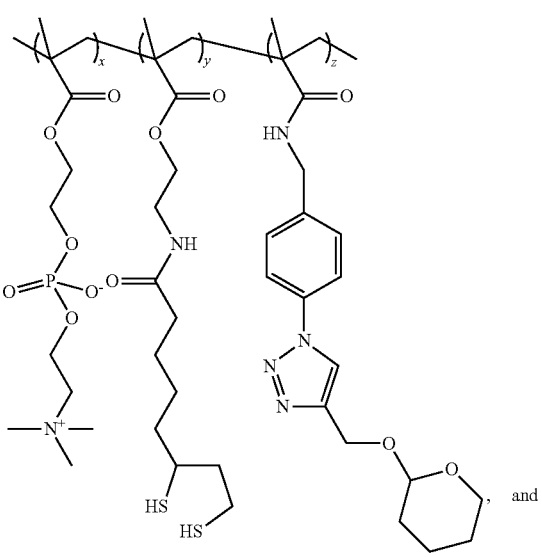
, and
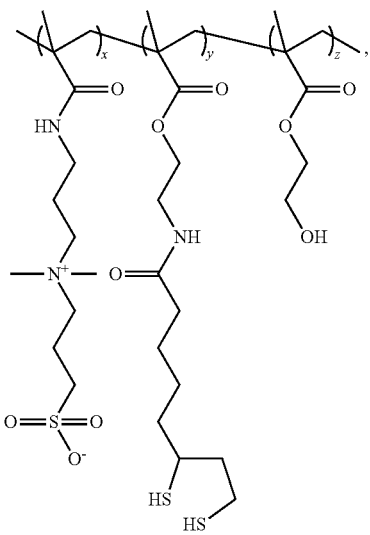
,
wherein, x and y are independently integers between 1 and 1000, inclusive; and z is between 0 and 1000, inclusive.

21. A biocompatible polymer comprising one or more monomer subunits A and B, wherein the polymer optionally further comprises one or more monomer subunits C;
- wherein each A is a zwitterionic monomer;
- wherein each B is a monomer with a reactive side chain;
- wherein each C is independently a hydrophobic monomer or a neutral hydrophilic monomer;
- wherein at least one A is a first zwitterionic monomer and at least one A is a second zwitterionic monomer, wherein the first zwitterionic monomer comprises a carboxybetaine group, and wherein the second zwitterionic monomer comprises a phosphoryl choline group;
- wherein the reactive side chain is Formula IV: d-$R_1$-Y;
- wherein:
  - d is the point of covalent attachment of the reactive side chain to the backbone of the polymer;
  - $R_1$ is unsubstituted alkyl, substituted alkyl, unsubstituted alkenyl, substituted alkenyl, unsubstituted alkynyl, substituted alkynyl, unsubstituted aryl, substituted aryl, unsubstituted heteroaryl, substituted heteroaryl, unsubstituted alkoxy, substituted alkoxy, unsubstituted aroxy, substituted aroxy, unsubstituted alkylthio, substituted alkylthio, unsubstituted arylthio, substituted arylthio, unsubstituted carbonyl, substituted carbonyl, unsubstituted carboxyl, substituted carboxyl, unsubstituted amino, substituted amino, unsubstituted amido, substituted amido, unsubstituted sulfonyl, substituted sulfonyl, unsubstituted sulfamoyl, substituted sulfamoyl, unsubstituted phosphonyl, substituted phosphonyl, unsubstituted polyaryl, substituted polyaryl, unsubstituted $C_3$-$C_{20}$ cyclic, substituted $C_3$-$C_{20}$ cyclic, unsubstituted $C_3$-$C_{20}$ heterocyclic, substituted $C_3$-$C_{20}$ heterocyclic, amino acid, poly(ethylene glycol), poly(lactic-co-glycolic acid), peptide, or polypeptide group; and
  - Y is propane-1,3-dithiol, 1,2-dithiolan-3-yl, 1,2-dithiol-3-ylidene, hydrogen, —SH, maleimide, aziridine, —$N_3$, —CN, acryloyl, acrylamide, —C(O)O$R_2$, —C(O)$R_3$, vinyl sulfone, —OH, cyanate, thiocyanate, isocyanate, isothiocyanate, alkoxysilane, vinyl silane, silicon hydride, -$NR_4R_5$, acetohydrazide, acyl azide, acyl halides, N-hydroxysuccinimide ester, sulfonyl chloride, glyoxal, epoxide, carbodiimides, aryl halides, or imido ester;
  - wherein $R_2$, $R_4$, and $R_5$, are, independently, hydrogen, amino, hydroxyl, thiol, oxo, phosphate, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, substituted or unsubstituted $C_{10}$ alkoxy, substituted or unsubstituted $C_1$-$C_{10}$ alkylamino, substituted or unsubstituted $C_1$-$C_{10}$ alkylthio, unsubstituted aryl, substituted aryl, unsubstituted heteroaryl, substituted heteroaryl, unsubstituted alkoxy, substituted alkoxy, unsubstituted aroxy, substituted aroxy, unsubstituted alkylthio, substituted alkylthio, unsubstituted arylthio, substituted arylthio, unsubstituted carbonyl, substituted carbonyl, unsubstituted carboxyl, substituted carboxyl, unsubstituted amino, substituted amino, unsubstituted amido, substituted amido, unsubstituted polyaryl, substituted polyaryl, $C_3$-$C_{20}$ cyclic, substituted $C_3$-$C_{20}$ cyclic, unsubstituted $C_3$-$C_{20}$ heterocyclic, or substituted $C_3$-$C_{20}$ heterocyclic; and
  - wherein $R_3$ is hydrogen, amino, hydroxyl, thiol, oxo, phosphate, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, substituted or unsubstituted $C_1$-$C_{10}$ alkoxy, substituted or unsubstituted $C_1$-$C_{10}$ alkylamino, substituted or unsubstituted $C_1$-$C_{10}$ alkylthio, unsubstituted aryl, substituted aryl, unsubstituted heteroaryl, substituted heteroaryl, unsubstituted alkoxy, substituted alkoxy, unsubstituted aroxy, substituted aroxy, unsubstituted alkylthio, substituted alkylthio, unsubstituted arylthio, substituted arylthio, unsubstituted carbonyl, substituted carbonyl, unsubstituted carboxyl, substituted carboxyl, unsubstituted amino, substituted amino, unsubstituted amido, substituted amido, unsubstituted polyaryl, substituted polyaryl, $C_3$-$C_{20}$ cyclic, substituted $C_3$-$C_{20}$ cyclic, unsubstituted $C_3$-$C_{20}$ heterocyclic, or substituted $C_3$-$C_{20}$ heterocyclic.

22. A hydrogel comprising the polymer of claim 1 cross-linked with a branched cross-linker, wherein the branched cross-linker comprises a plurality of branches, wherein two or more of the branches comprise a reactive group, wherein the reactive group reacts with the Y group on the reactive side chain of the polymer to crosslink the polymer.

23. The hydrogel of claim 22, wherein the Y group on the reactive side chain comprises a sulfhydryl group, and wherein the reactive group on the cross-linker comprises a maleimide group.

24. The hydrogel of claim 22, having a mean pore size between about 10 nm and about 20 μm, inclusive, as determined using cryo-scanning electron microscopy.

25. The hydrogel of claim 22 further comprising culture media, pharmaceutically acceptable excipients suitable for implantation into human, or a combination thereof.

26. A biomaterial or device comprising a coating formed from the polymer of claim 1.

27. The device of claim 26, wherein the device is selected from the group consisting of implantable medical products, implantable devices, catheters, vascular catheter ports, blood clot filters, urinary devices, shunts, cannulas, balloons, pacemakers, implantable defibrillators, orthopedic products, prostheses, aneurysm-filling coils and other coil devices, transmyocardial revascularization devices, percutaneous myocardial revascularization devices, fibers, hollow fibers, membranes, blood containers, titer plates, adsorber media, dialyzers, connecting pieces, sensors, valves, endoscopes, filters, pump chambers, scalpels, needles, and scissors.

28. The biomaterial of claim 26, wherein the biomaterial is formed from a polymer selected from the group consisting of polysaccharides, polystyrene, polyphosphazenes, poly (acrylic acids), poly(methacrylic acids), poly(alkylene oxides), poly(vinyl acetate), polyvinylpyrrolidone, poly(vinyl amines), poly(vinyl pyridine), poly(vinyl imidazole), poly(anhydrides), poly(hydroxy acids), polyesters, poly(ortho esters), poly(propylene fumarates), polyamides, polyamino acids, polyethers, polyacetals, polyhydroxyalkanoates, polyketals, polyesteramides, poly(dioxanones), polycarbonates, polyorthocarbonates, polycyanoacrylates, polyalkylene oxalates, polyalkylene succinates, poly(malic acid), poly(methyl vinyl ether), poly(ethylene imine), poly (maleic anhydride), and copolymers and blends thereof.

29. The device or biomaterial of claim 26, wherein the thickness of the coating is between about 10 nm and about 1 cm, inclusive.

30. The device or biomaterial of claim 26, wherein the coating has a mean pore size between about 1 nm and about 20 μm, inclusive.

31. A method of coating the surface of a biomaterial or device, the method comprising:

(i) contacting the biomaterial or device with a solution of the biocompatible polymer of claim 1; and
(ii) optionally contacting the solution with a cross-linker, wherein the cross-linker contains a reactive group.

32. The method of claim 31 further comprising treating the surface of the biomaterial or device with a material prior to contacting the biomaterial or device with the solution.

33. A method of treating or diagnosing a disease, disorder, or condition in a human or animal subject, the method comprising implanting or transplanting into the human or animal subject the hydrogel of claim 22.

34. The biocompatible polymer of claim 1, wherein $R_1$ in Formula IV is not -Aq-unsubstituted $C_1$-$C_5$ alkylene-Bq-unsubstituted $C_1$-$C_5$ alkylene-, wherein Aq is —OC(O)—, and Bq is —OC(O)—.

35. The biocompatible polymer of claim 1, not comprising the one or more monomer subunits C.

36. The biocompatible polymer of claim 21, not comprising the one or more monomer subunits C.

37. The biocompatible polymer of claim 20, having one or more of the following features:
x is between 10 and 200, inclusive;
y is between 2 and 20, inclusive; and
z is between 10 and 200, inclusive.

38. A biocompatible polymer comprising one or more monomer subunits A and B, wherein the polymer optionally further comprises one or more monomer subunits C;
wherein each A is a zwitterionic monomer;
wherein each B is a monomer with a reactive side chain, wherein the reactive side chain is Formula IV: d-$R_1$-Y comprising an amide bond and further comprising an ester, ether, acylhydrazine, carbamate, ketone, carbonate, sulfone, sulfoxide, thioether, azo, or aldimine;
wherein each C is independently a hydrophobic monomer or a neutral hydrophilic monomer;
wherein d is the point of covalent attachment of the reactive side chain to the backbone of the polymer;
wherein $R_1$ is -Aq-unsubstituted $C_1$-$C_{10}$ alkylene-Bq-unsubstituted $C_1$-$C_{10}$ alkylene-, -Aq-unsubstituted $C_1$-$C_{10}$ alkylene-Bq-substituted $C_1$-$C_{10}$ alkylene-, or -Aq-substituted $C_1$-$C_{10}$ alkylene-Bq-unsubstituted $C_1$-$C_{10}$ alkylene-, wherein Aq and Bq are independently —C(O)O—, —C(O)NH—, —OC(O)—, —NHC(O)—, —O—, —NH—NHC(O)—, —OC(O)NH—, —NHC(O)O—, —C(O)—, —OC(O)O—, —S(=$O_2$)$_2$—, —S(=O)—, —S—, —N=N—, or —N=CH—; and
wherein Y is propane-1,3-dithiol, 1,2-dithiolan-3-yl, 1,2-dithiol-3-ylidene, —SH, maleimide, aziridine, —$N_3$, —CN, acryloyl, acrylamide, —C(O)O$R_2$, —C(O)$R_3$, vinyl sulfone, —OH, cyanate, thiocyanate, isocyanate, isothiocyanate, alkoxysilane, vinyl silane, silicon hydride, —N$R_4R_5$, acetohydrazide, acyl azide, acyl halides, N-hydroxysuccinimide ester, sulfonyl chloride, glyoxal, epoxide, carbodiimides, aryl halides, or imido ester;
wherein $R_2$, $R_4$, and $R_5$, are, independently, hydrogen, amino, hydroxyl, thiol, oxo, phosphate, or substituted or unsubstituted $C_1$-$C_{10}$ alkyl, substituted or unsubstituted $C_2$-$C_{10}$ alkenyl, substituted or unsubstituted $C_2$-$C_{10}$ alkynyl, substituted or unsubstituted $C_1$-$C_{10}$ alkoxy, substituted or unsubstituted $C_1$-$C_{10}$ alkylamino, substituted or unsubstituted alkylthio, unsubstituted aryl, substituted aryl, unsubstituted heteroaryl, substituted heteroaryl, unsubstituted alkoxy, substituted alkoxy, unsubstituted aroxy, substituted aroxy, unsubstituted alkylthio, substituted alkylthio, unsubstituted arylthio, substituted arylthio, unsubstituted carbonyl, substituted carbonyl, unsubstituted carboxyl, substituted carboxyl, unsubstituted amino, substituted amino, unsubstituted amido, substituted amido, unsubstituted polyaryl, substituted polyaryl, unsubstituted $C_3$-$C_{20}$ cyclic, substituted $C_3$-$C_{20}$ cyclic, unsubstituted $C_3$-$C_{20}$ heterocyclic, or substituted $C_3$-$C_{20}$ heterocyclic; and
wherein $R_3$ is hydrogen, amino, hydroxyl, thiol, oxo, phosphate, or substituted or unsubstituted $C_1$-$C_{10}$ alkyl, substituted or unsubstituted alkenyl, substituted or unsubstituted $C_2$-$C_{10}$ alkynyl, substituted or unsubstituted alkoxy, substituted or unsubstituted $C_1$-$C_{10}$ alkylamino, substituted or unsubstituted $C_1$-$C_{10}$ alkylthio, unsubstituted aryl, substituted aryl, unsubstituted heteroaryl, substituted heteroaryl, unsubstituted alkoxy, substituted alkoxy, unsubstituted aroxy, substituted aroxy, unsubstituted alkylthio, substituted alkylthio, unsubstituted arylthio, substituted arylthio, unsubstituted carbonyl, substituted carbonyl, unsubstituted carboxyl, substituted carboxyl, unsubstituted amino, substituted amino, unsubstituted amido, substituted amido, unsubstituted polyaryl, substituted polyaryl, $C_3$-$C_{20}$ cyclic, substituted $C_3$-$C_{20}$ cyclic, unsubstituted $C_3$-$C_{20}$ heterocyclic, or substituted $C_3$-$C_{20}$ heterocyclic.

39. The polymer of claim 38, wherein Aq and Bq are —C(O)O— and —NHC(O)—, respectively, or —NHC(O)— and —C(O)O—, respectively.

40. A biocompatible polymer comprising one or more monomer subunits A and B, wherein the polymer optionally further comprises one or more monomer subunits C;
wherein each A is a zwitterionic monomer;
wherein each B is a monomer with a reactive side chain, wherein the reactive side chain is Formula IV: d-$R_1$-Y comprising an amide bond;
wherein each C is independently a hydrophobic monomer or a neutral hydrophilic monomer;
wherein d is the point of covalent attachment of the reactive side chain to the backbone of the polymer;
wherein $R_1$ is -Aq-unsubstituted $C_1$-$C_{10}$ alkylene-Bq-unsubstituted $C_1$-$C_{10}$ alkylene-, -Aq-unsubstituted $C_1$-$C_{10}$ alkylene-Bq-substituted $C_1$-$C_{10}$ alkylene-, -Aq-substituted $C_1$-$C_{10}$ alkylene-Bq-unsubstituted $C_1$-$C_{10}$ alkylene-, or -Aq-substituted $C_1$-$C_{10}$ alkylene-Bq-substituted $C_1$-$C_{10}$ alkylene-, wherein either:
(1) Aq and Bq are independently —C(O)O—, —OC(O)—, —O—, —NH—NHC(O)—, —OC(O)NH—, —NHC(O)O—, —C(O)—, —OC(O)O—, —S(=$O_2$)$_2$—, —S(=O)—, —S—, —N=N—, or —N=CH—,
(2) Aq is —C(O)O—, —OC(O)—, —O—, —NH—NHC(O)—, —OC(O)NH—, —NHC(O)O—, —C(O)—, —OC(O)O—, —S(=$O_2$)$_2$—, —S(=O)—, —S—, —N=N—, or —N=CH— and Bq is —C(O)O—, —OC(O)—, —C(O)NH—, —NHC(O)—, —O—, —NH—NHC(O)—, —OC(O)NH—, —NHC(O)O—, —C(O)—, —OC(O)O—, —S(=$O_2$)$_2$—, —S(=O)—, —S—, —N=N—, or —N=CH—, or
(3) Aq is —C(O)O—, —OC(O)—, —C(O)NH—, —NHC(O)—, —O—, —NH—NHC(O)—, —OC(O)NH—, —NHC(O)O—, —C(O)—, —OC(O)O—, —S(=$O_2$)$_2$—, —S(=O)—, —S—, —N=N—, or —N=CH— and Bq is —C(O)O—, —OC(O)—, —O—, —NH—NHC(O)—, —OC(O)

—NH—, —NHC(O)O—, —C(O)—, —OC(O)O—, —S(=O$_2$)$_2$—, —S(=O)—, —S—, —N=N—, or —N=CH—;

wherein Y is propane-1,3-dithiol, 1,2-dithiolan-3-yl, 1,2-dithiol-3-ylidene, —SH, maleimide, aziridine, -N$_3$, —CN, acryloyl, acrylamide, —C(O)OR$_2$, —C(O)R$_3$, vinyl sulfone, —OH, cyanate, thiocyanate, isocyanate, isothiocyanate, alkoxysilane, vinyl silane, silicon hydride, —NR$_4$R$_5$, acetohydrazide, acyl azide, acyl halides, N-hydroxysuccinimide ester, sulfonyl chloride, glyoxal, epoxide, carbodiimides, aryl halides, or imido ester;

wherein R$_2$, R$_4$, and R$_5$, are, independently, hydrogen, amino, hydroxyl, thiol, oxo, phosphate, substituted or unsubstituted C$_1$-C$_{10}$ alkyl, substituted or unsubstituted C$_2$-C$_{10}$ alkenyl, substituted or unsubstituted C$_2$-C$_{10}$ alkynyl, substituted or unsubstituted C$_1$-C$_{10}$ alkoxy, substituted or unsubstituted C$_1$-C$_{10}$ alkylamino, substituted or unsubstituted C$_1$-C$_{10}$ alkylthio, unsubstituted aryl, substituted aryl, unsubstituted heteroaryl, substituted heteroaryl, unsubstituted alkoxy, substituted alkoxy, unsubstituted aroxy, substituted aroxy, unsubstituted alkylthio, substituted alkylthio, unsubstituted arylthio, substituted arylthio, unsubstituted carbonyl, substituted carbonyl, unsubstituted carboxyl, substituted carboxyl, unsubstituted amino, substituted amino, unsubstituted amido, substituted amido, unsubstituted polyaryl, substituted polyaryl, unsubstituted C$_3$-C$_{20}$ cyclic, substituted C$_3$-C$_{20}$ cyclic, unsubstituted C$_3$-C$_{20}$ heterocyclic, or substituted C$_3$-C$_{20}$ heterocyclic; and wherein R$_3$ is hydrogen, amino, hydroxyl, thiol, oxo, phosphate, substituted or unsubstituted C$_1$-C$_{10}$ alkyl, substituted or unsubstituted C$_2$-C$_{10}$ alkenyl, substituted or unsubstituted C$_2$-C$_{10}$ alkynyl, substituted or unsubstituted C$_1$-C$_{10}$ alkoxy, substituted or unsubstituted C$_1$-C$_{10}$ alkylamino, substituted or unsubstituted C$_1$-C$_{10}$ alkylthio, unsubstituted aryl, substituted aryl, unsubstituted heteroaryl, substituted heteroaryl, unsubstituted alkoxy, substituted alkoxy, unsubstituted aroxy, substituted aroxy, unsubstituted alkylthio, substituted alkylthio, unsubstituted arylthio, substituted arylthio, unsubstituted carbonyl, substituted carbonyl, unsubstituted carboxyl, substituted carboxyl, unsubstituted amino, substituted amino, unsubstituted amido, substituted amido, unsubstituted polyaryl, substituted polyaryl, C$_3$-C$_{20}$ cyclic, substituted C$_3$-C$_{20}$ cyclic, unsubstituted C$_3$-C$_{20}$ heterocyclic, or substituted C$_3$-C$_{20}$ heterocyclic.

41. A biocompatible polymer comprising one or more monomer subunits A and B, wherein the polymer optionally further comprises one or more monomer subunits C;
   wherein each A is a zwitterionic monomer;
   wherein each B is a monomer with a reactive side chain, wherein the reactive side chain is Formula IV: d-R$_1$-Y comprising an amide bond;
   wherein each C is independently a hydrophobic monomer or a neutral hydrophilic monomer;
      wherein d is the point of covalent attachment of the reactive side chain to the backbone of the polymer, and the reactive side chain is not attached to the backbone of the polymer via an amide bond;

wherein:
R$_1$ is unsubstituted alkyl, substituted alkyl, unsubstituted alkenyl, substituted alkenyl, unsubstituted alkynyl, substituted alkynyl, unsubstituted aryl, substituted aryl, unsubstituted heteroaryl, substituted heteroaryl, unsubstituted alkoxy, unsubstituted aroxy, substituted aroxy, unsubstituted alkylthio, substituted alkylthio, unsubstituted arylthio, substituted arylthio, unsubstituted carbonyl, unsubstituted carboxyl, unsubstituted amido, unsubstituted sulfonyl, substituted sulfonyl, unsubstituted sulfamoyl, substituted sulfamoyl, unsubstituted phosphonyl, substituted phosphonyl, unsubstituted polyaryl, substituted polyaryl, unsubstituted C$_3$-C$_{20}$ cyclic, substituted C$_3$-C$_{20}$ cyclic, unsubstituted C$_3$-C$_{20}$ heterocyclic, substituted C$_3$-C$_{20}$ heterocyclic, amino acid, poly(lactic-co-glycolic acid), peptide, or polypeptide group; and Y is propane-1,3-dithiol, 1,2-dithiolan-3-yl, 1,2-dithiol-3-ylidene, —SH, maleimide, aziridine, —N$_3$, —CN, acryloyl, acrylamide, —C(O)OR$_2$, —C(O)R$_3$, vinyl sulfone, cyanate, thiocyanate, isocyanate, isothiocyanate, alkoxysilane, vinyl silane, silicon hydride, —NR$_4$R$_5$, acetohydrazide, acyl azide, acyl halides, N-hydroxysuccinimide ester, sulfonyl chloride, glyoxal, epoxide, carbodiimides, aryl halides, or imido ester;
or
R$_1$ is unsubstituted alkyl, substituted alkyl, unsubstituted alkenyl, substituted alkenyl, unsubstituted alkynyl, substituted alkynyl, unsubstituted aryl, substituted aryl, heteroaryl, substituted heteroaryl, unsubstituted alkoxy, substituted alkoxy, aroxy, substituted aroxy, unsubstituted alkylthio, substituted alkylthio, unsubstituted arylthio, substituted arylthio, unsubstituted carbonyl, substituted carbonyl, unsubstituted carboxyl, substituted carboxyl, unsubstituted amino, substituted amino, unsubstituted amido, substituted amido, unsubstituted sulfonyl, substituted sulfonyl, unsubstituted sulfamoyl, substituted sulfamoyl, unsubstituted phosphonyl, substituted phosphonyl, unsubstituted polyaryl, substituted polyaryl, unsubstituted C$_3$-C$_{20}$ cyclic, substituted C$_3$-C$_{20}$ cyclic, unsubstituted C$_3$-C$_{20}$ heterocyclic, substituted C$_3$-C$_{20}$ heterocyclic, amino acid, poly(ethylene glycol), poly(lactic-co-glycolic acid), peptide, or polypeptide group; and Y is propane-1,3-dithiol, 1,2-dithiolan-3-yl, 1,2-dithiol-3-ylidene, —SH, maleimide, aziridine, -N$_3$, —CN, acrylamide, —C(O)OR$_2$, —C(O)R$_3$, vinyl sulfone, cyanate, thiocyanate, isocyanate, isothiocyanate, vinyl silane, silicon hydride, acetohydrazide, acyl azide, acyl halides, N-hydroxysuccinimide ester, sulfonyl chloride, glyoxal, carbodiimides, aryl halides, or imido ester;
wherein R$_2$ and R$_4$ are, independently, hydrogen, amino, hydroxyl, thiol, oxo, phosphate, substituted or unsubstituted C$_1$-C$_{10}$ alkyl, substituted or unsubstituted C$_2$-C$_{10}$ alkenyl, substituted or unsubstituted C$_2$-C$_{10}$ alkynyl, substituted or unsubstituted C$_1$-C$_{10}$ alkoxy, substituted or unsubstituted C$_1$-C$_{10}$ alkylamino, substituted or unsubstituted C$_1$-C$_{10}$ alkylthio, unsubstituted aryl, substituted aryl, unsubstituted heteroaryl, substituted heteroaryl, unsubstituted alkoxy, substituted alkoxy, unsubstituted aroxy, substituted aroxy, unsubstituted alkylthio, substituted alkylthio, unsubstituted arylthio, substituted arylthio, unsubstituted carbonyl, substituted carbonyl, unsubstituted carboxyl, substituted carboxyl, amino, substituted amino, amido, substituted amido, polyaryl, substituted polyaryl, $C_3$-$C_{20}$ cyclic, substituted $C_3$-$C_{20}$ cyclic, unsubstituted $C_3$-$C_{20}$ heterocyclic, or substituted $C_3$-$C_{20}$ heterocyclic;

wherein $R_5$ is amino, hydroxyl, thiol, oxo, phosphate, substituted $C_1$-$C_{10}$ alkyl, substituted or unsubstituted alkenyl, substituted or unsubstituted $C_2$-$C_{10}$ alkynyl, substituted or unsubstituted $C_1$-$C_{10}$ alkoxy, substituted or unsubstituted $C_1$-$C_{10}$ alkylamino, substituted or unsubstituted $C_1$-$C_{10}$ alkylthio, unsubstituted aryl, substituted aryl, unsubstituted heteroaryl, substituted heteroaryl, unsubstituted alkoxy, substituted alkoxy, unsubstituted aroxy, substituted aroxy, unsubstituted alkylthio, substituted alkylthio, unsubstituted arylthio, substituted arylthio, unsubstituted carbonyl, substituted carbonyl, unsubstituted carboxyl, substituted carboxyl, amino, substituted amino, amido, substituted amido, polyaryl, substituted polyaryl, $C_3$-$C_{20}$ cyclic, substituted $C_3$-$C_{20}$ cyclic, unsubstituted $C_3$-$C_{20}$ heterocyclic, or substituted $C_3$-$C_{20}$ heterocyclic, wherein when $R_5$ is substituted $C_1$-$C_{10}$ alkyl, $R_5$ includes a secondary amine group; and wherein $R_3$ is amino, hydroxyl, thiol, oxo, phosphate, substituted $C_1$-$C_{10}$ alkyl, substituted or unsubstituted $C_2$-$C_{10}$ alkenyl, substituted or unsubstituted $C_2$-$C_{10}$ alkynyl, substituted or unsubstituted $C_1$-$C_{10}$ alkoxy, substituted or unsubstituted $C_1$-$C_{10}$ alkylamino, substituted or unsubstituted $C_1$-$C_{10}$ alkylthio, unsubstituted aryl, substituted aryl, unsubstituted heteroaryl, substituted heteroaryl, unsubstituted alkoxy, substituted alkoxy, unsubstituted aroxy, substituted aroxy, unsubstituted alkylthio, substituted alkylthio, unsubstituted arylthio, substituted arylthio, unsubstituted carbonyl, substituted carbonyl, unsubstituted carboxyl, substituted carboxyl, unsubstituted amino, substituted amino, unsubstituted amido, substituted amido, unsubstituted polyaryl, substituted polyaryl, unsubstituted $C_3$-$C_{20}$ cyclic, substituted $C_3$-$C_{20}$ cyclic, unsubstituted $C_3$-$C_{20}$ heterocyclic, or substituted $C_3$-$C_{20}$ heterocyclic.

42. The polymer of claim 41, wherein monomer subunits A, B, and C are in the ratio of x:y:z, respectively, wherein x and y are, independently, integers between 1 and 1000, inclusive, and wherein z is an integer between 0 and 1000, inclusive; and wherein the polymer has n total monomer subunits, wherein n is an integer between 2 and 2000, inclusive.

43. The polymer of claim 41, wherein the reactive side chain is d-C(O)—O—$CH_2$—$CH_2$—NH—C(O)—$CH_2$—$CH_2$—$CH_2$—$CH_2$—CH(SH)—$CH_2$—$CH_2$—SH.

44. The polymer of claim 41, comprising a structure selected from the group consisting of:

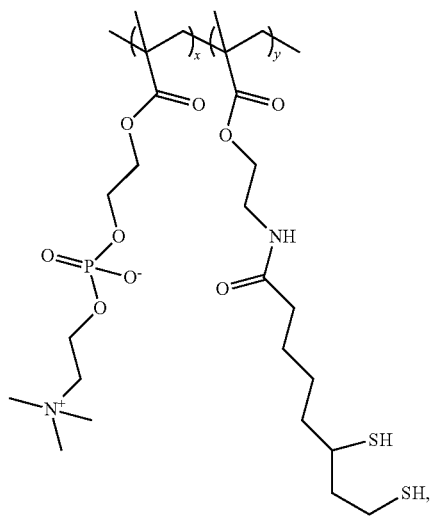

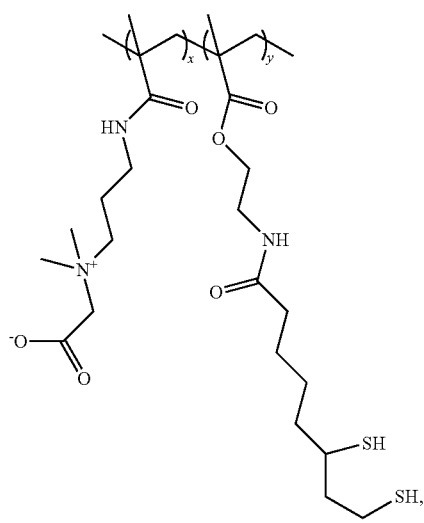

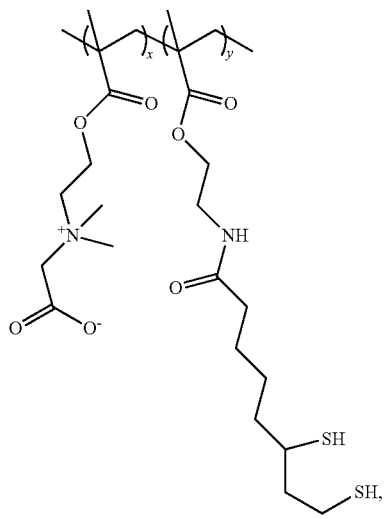

77
-continued
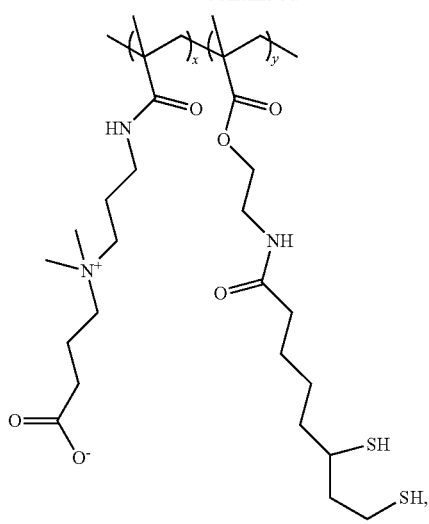
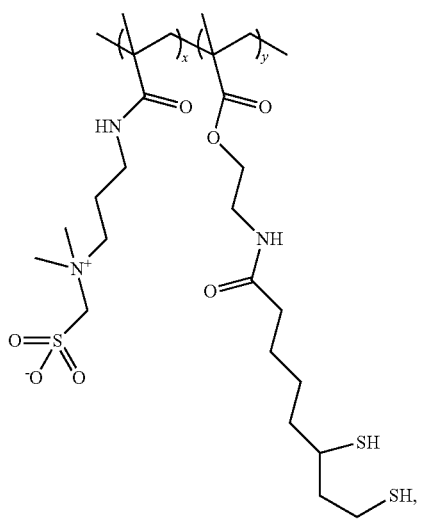
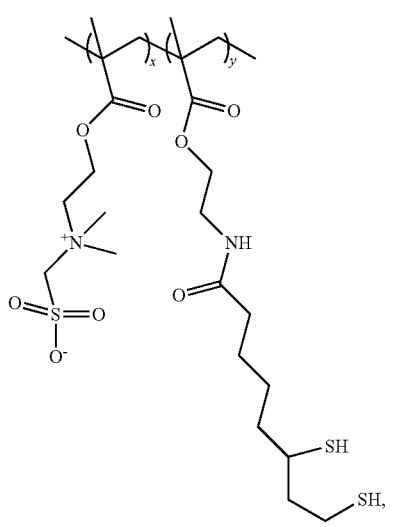
78
-continued
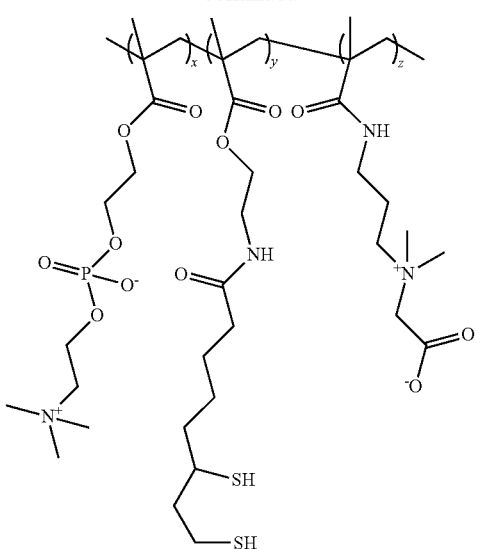
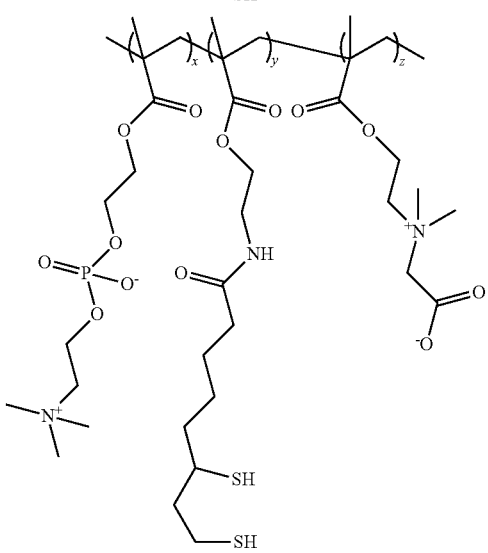
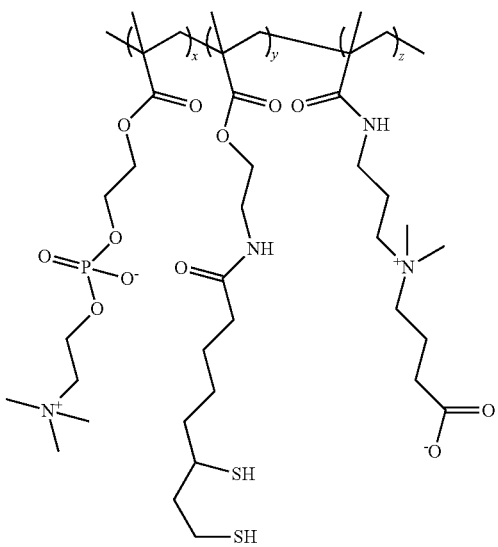

79
-continued
80
-continued
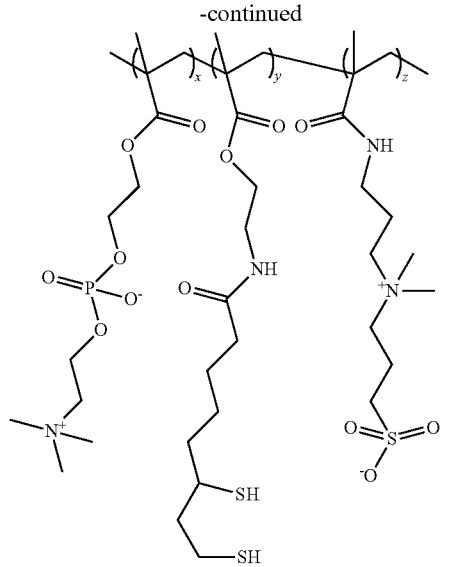
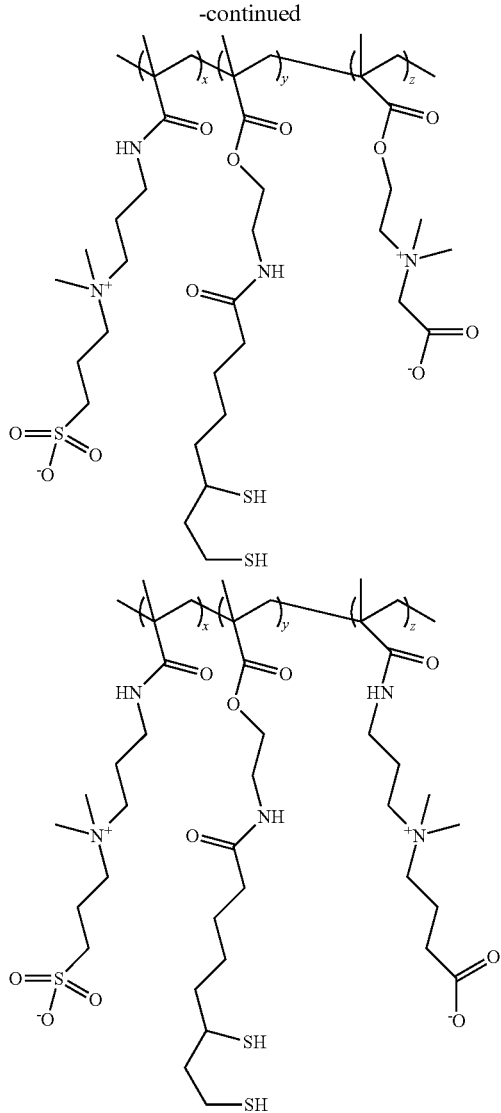
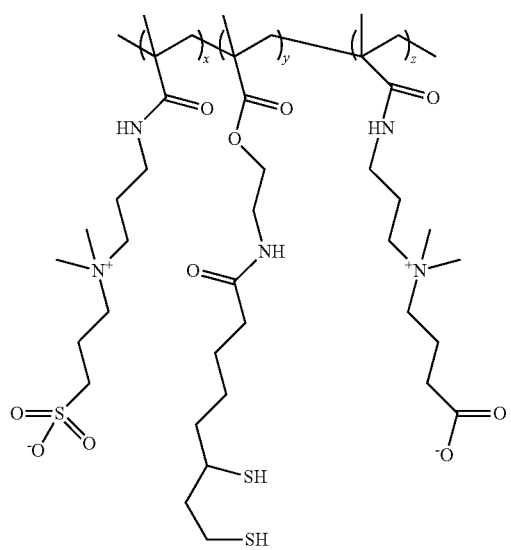
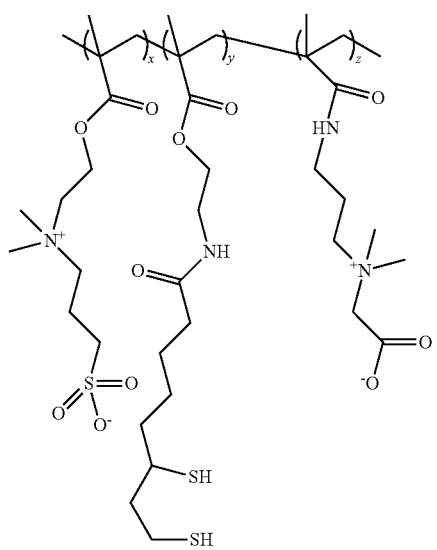

81
-continued
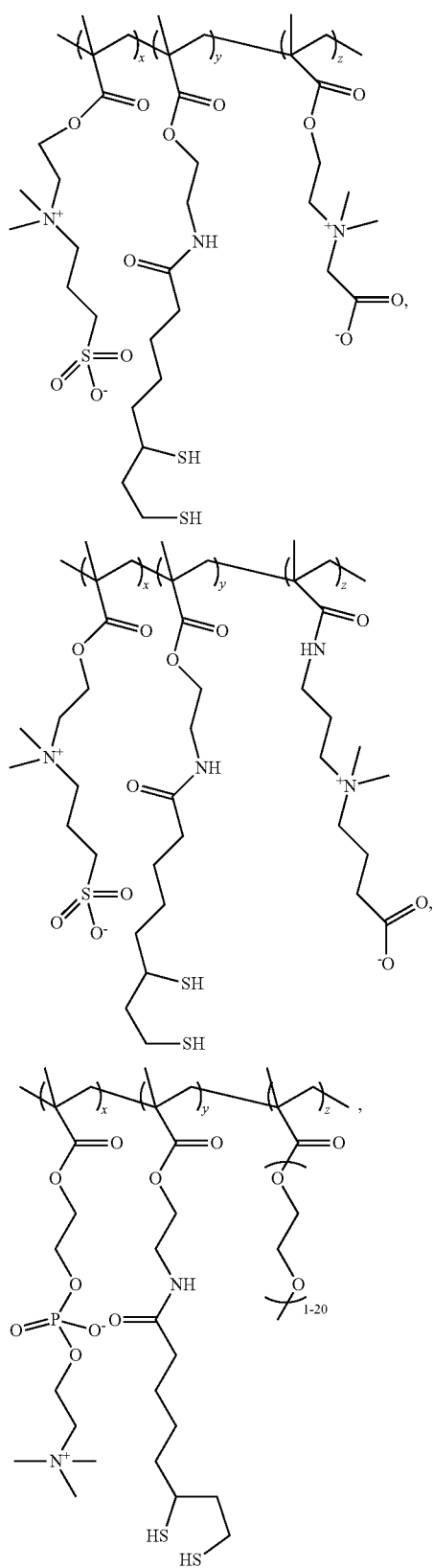
82
-continued
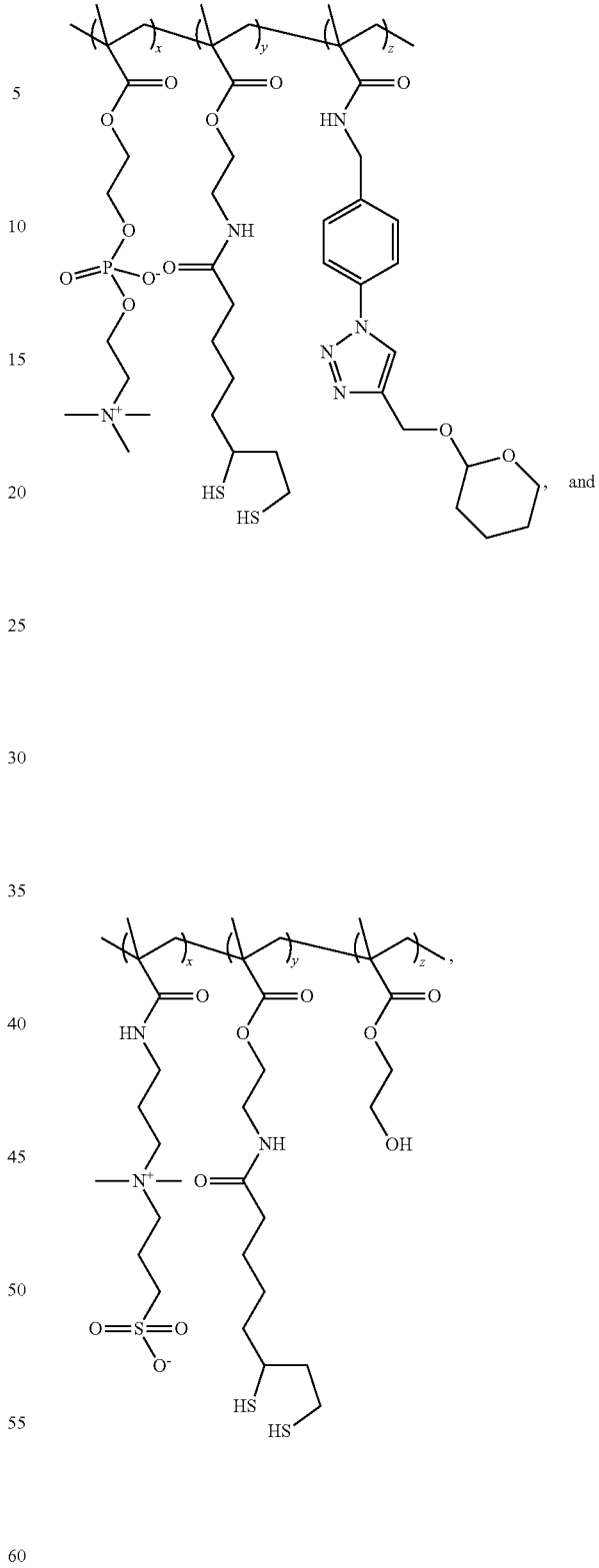
wherein x and y are independently integers between 1 and 1000, inclusive; and z is between 0 and 1000, inclusive.
* * * * *

UNITED STATES PATENT AND TRADEMARK OFFICE
CERTIFICATE OF CORRECTION

PATENT NO. : 10,730,983 B2  
APPLICATION NO. : 15/621391  
DATED : August 4, 2020  
INVENTOR(S) : Veiseh et al.

Page 1 of 1

It is certified that error appears in the above-identified patent and that said Letters Patent is hereby corrected as shown below:

In the Specification

In Column 1, Lines 12-18, delete:
"This invention was made with government support under Grant Nos. EB000244, EB000351, DE013023, CA151884, and P41EB015871-27 awarded by the National Institutes of Health; and Grant Nos. 3-2013-178 and W81XWH13-1-0215 awarded by the Department of Defense/Congressionally Directed Medical Research Programs. The government has certain rights in the invention."

And insert:
-- This invention was made with government support under CA151884, DE013023, EB000244, EB000351, and EB015871 awarded by the National Institutes of Health. The government has certain rights in the invention. --

Signed and Sealed this  
Twenty-fifth Day of November, 2025

John A. Squires  
*Director of the United States Patent and Trademark Office*